(12) United States Patent
Min et al.

(10) Patent No.: US 7,918,350 B2
(45) Date of Patent: *Apr. 5, 2011

(54) SEPARATION APPARATUS AND METHOD

(75) Inventors: Kyungyoon Min, Gurnee, IL (US);
Richard I. Brown, Northbrook, IL (US);
Alp Akonur, Evanston, IL (US); Julie Moriarty, Chatswood (AU)

(73) Assignee: Fenwal, Inc., Lake Zurich, IL (US)

( * ) Notice: Subject to any disclaimer, the term of this patent is extended or adjusted under 35 U.S.C. 154(b) by 23 days.

This patent is subject to a terminal disclaimer.

(21) Appl. No.: 12/399,545

(22) Filed: Mar. 6, 2009

(65) Prior Publication Data

US 2009/0218277 A1    Sep. 3, 2009

Related U.S. Application Data

(63) Continuation of application No. 11/927,033, filed on Oct. 29, 2007, now abandoned, which is a continuation of application No. 10/827,603, filed on Apr. 19, 2004, now Pat. No. 7,297,272, which is a continuation-in-part of application No. 10/279,765, filed on Oct. 24, 2002, now Pat. No. 6,849,039.

(60) Provisional application No. 60/533,820, filed on Dec. 31, 2003.

(51) Int. Cl.
*B04B 3/00* (2006.01)
*B04B 1/06* (2006.01)
*B04B 1/12* (2006.01)
*B04B 7/10* (2006.01)
*B01D 21/26* (2006.01)
*B01D 45/12* (2006.01)

(52) U.S. Cl. ............ 210/512.1; 210/782; 210/787; 210/789; 494/37; 494/43; 494/45; 494/67; 494/56

(58) Field of Classification Search ............ None
See application file for complete search history.

(56) References Cited

U.S. PATENT DOCUMENTS 1,647,292 A    11/1927    Hill (Continued)

FOREIGN PATENT DOCUMENTS

DE    197 06 997 A1    8/1998

(Continued)

OTHER PUBLICATIONS

PCT/US00/23696 International Search Report dated Jan. 9, 2001, Baxter International.

(Continued)

*Primary Examiner* — Krishnan S Menon
(74) *Attorney, Agent, or Firm* — Cook Alex Ltd.

(57) ABSTRACT

A separation apparatus and method are employed using a separation channel for rotation about an axis. Such channel includes radially spaced apart inner and outer side wall portions and an end wall portion. An inlet conveys fluid into the channel. A barrier is located in the channel intermediate of the inner and outer side wall portions. A first flow path communicates between upstream and downstream sides of the barrier. A collection region may be located downstream of the barrier for communication with the first flow path. An outer side wall section of the channel may be positioned radially outward of an upstream section thereof. The barrier may join the outer side wall portion along a substantial portion of an axial length of the channel. First and second exit flow paths may allow communication with the channel either upstream or downstream of the barrier or both.

17 Claims, 40 Drawing Sheets

U.S. PATENT DOCUMENTS

| | | |
|---|---|---|
| 3,666,170 A | 5/1972 | Cacciabue et al. |
| 3,785,549 A | 1/1974 | Latham, Jr. |
| 4,010,894 A | 3/1977 | Kellogg et al. |
| 4,091,989 A | 5/1978 | Schlutz |
| 4,094,461 A | 6/1978 | Kellogg et al. |
| 4,109,854 A | 8/1978 | Brown |
| 4,120,448 A | 10/1978 | Cullis |
| 4,132,349 A | 1/1979 | Khoja et al. |
| 4,146,172 A | 3/1979 | Cullis et al. |
| 4,164,318 A | 8/1979 | Boggs |
| 4,189,382 A | 2/1980 | Zine, Jr. |
| 4,278,202 A | 7/1981 | Westberg |
| 4,303,193 A | 12/1981 | Latham, Jr. |
| 4,330,080 A | 5/1982 | Mathieu |
| 4,342,420 A | 8/1982 | Rosemeier et al. |
| 4,389,206 A | 6/1983 | Bacehowski et al. |
| 4,402,680 A | 9/1983 | Schoendorfer |
| 4,447,221 A | 5/1984 | Mulzet |
| 4,640,785 A | 2/1987 | Carroll et al. |
| 4,647,279 A | 3/1987 | Mulzet et al. |
| 4,708,712 A | 11/1987 | Mulzet |
| 4,713,176 A | 12/1987 | Schoendorfer et al. |
| 4,734,089 A | 3/1988 | Cullis |
| 4,776,964 A | 10/1988 | Schoendorfer et al. |
| 4,798,577 A | 1/1989 | Brenneman et al. |
| 4,816,168 A | 3/1989 | Carrol et al. |
| 4,818,418 A | 4/1989 | Saunders |
| 4,834,890 A | 5/1989 | Brown et al. |
| 4,867,887 A | 9/1989 | Smith |
| 4,871,462 A | 10/1989 | Fischel et al. |
| 4,895,666 A | 1/1990 | Franzen et al. |
| 4,911,833 A | 3/1990 | Schoendorfer et al. |
| 4,944,883 A | 7/1990 | Schoendorfer et al. |
| 4,954,264 A | 9/1990 | Smith |
| 4,957,637 A | 9/1990 | Cornell |
| 4,957,638 A | 9/1990 | Smith |
| 4,981,585 A | 1/1991 | Kelley et al. |
| 4,985,153 A | 1/1991 | Kuroda et al. |
| 5,061,381 A | 10/1991 | Burd |
| 5,071,570 A | 12/1991 | Shiraki et al. |
| 5,078,671 A | 1/1992 | Dennehey et al. |
| 5,100,564 A | 3/1992 | Pall et al. |
| 5,124,434 A | 6/1992 | O'Brien |
| 5,173,193 A | 12/1992 | Schembri |
| 5,186,844 A | 2/1993 | Burd et al. |
| 5,217,627 A | 6/1993 | Pall et al. |
| 5,258,126 A | 11/1993 | Pall et al. |
| 5,281,342 A | 1/1994 | Biesel et al. |
| 5,308,309 A | 5/1994 | Morris |
| 5,316,540 A | 5/1994 | McMannis et al. |
| 5,350,514 A | 9/1994 | Witthaus et al. |
| 5,362,291 A | 11/1994 | Williamson, IV |
| 5,370,802 A | 12/1994 | Brown |
| 5,386,734 A | 2/1995 | Pusinelli |
| 5,387,174 A | 2/1995 | Rochat |
| 5,387,187 A | 2/1995 | Fell et al. |
| 5,454,958 A | 10/1995 | Fiehler |
| 5,456,845 A | 10/1995 | Nishimura et al. |
| 5,462,416 A | 10/1995 | Dennehey et al. |
| 5,464,536 A | 11/1995 | Rogers |
| 5,494,578 A | 2/1996 | Brown et al. |
| 5,494,592 A | 2/1996 | Latham, Jr. et al. |
| 5,506,333 A | 4/1996 | O'Brien et al. |
| 5,529,567 A | 6/1996 | Toth et al. |
| 5,545,339 A | 8/1996 | Bormann et al. |
| 5,547,591 A | 8/1996 | Hagihara et al. |
| 5,549,834 A | 8/1996 | Brown |
| 5,556,557 A | 9/1996 | O'Brien et al. |
| 5,571,068 A | 11/1996 | Bacehowski et al. |
| 5,581,687 A | 12/1996 | Lyle et al. |
| 5,585,007 A | 12/1996 | Antanvich et al. |
| 5,603,845 A | 2/1997 | Holm |
| 5,607,579 A | 3/1997 | Latham, Jr. et al. |
| 5,616,254 A | 4/1997 | Pall et al. |
| 5,628,915 A | 5/1997 | Brown et al. |
| 5,632,905 A | 5/1997 | Haynes |
| 5,643,193 A | 7/1997 | Papillon et al. |
| 5,651,766 A | 7/1997 | Kingsley et al. |
| 5,656,163 A | 8/1997 | Brown |
| 5,658,231 A | 8/1997 | Schmitt et al. |
| 5,663,051 A | 9/1997 | Vlasselaer |
| 5,702,357 A | 12/1997 | Bainbridge et al. |
| 5,704,888 A | 1/1998 | Hlavinka et al. |
| 5,704,889 A | 1/1998 | Hlavinka et al. |
| 5,707,876 A | 1/1998 | Levine |
| 5,720,716 A | 2/1998 | Blakeslee et al. |
| 5,722,926 A | 3/1998 | Hlavinka et al. |
| 5,722,946 A | 3/1998 | Mudloff et al. |
| 5,730,883 A | 3/1998 | Brown |
| 5,738,796 A | 4/1998 | Bormann et al. |
| 5,750,025 A | 5/1998 | Holmes et al. |
| 5,750,039 A | 5/1998 | Brown et al. |
| 5,769,811 A | 6/1998 | Stacey et al. |
| 5,788,662 A | 8/1998 | Antanavich et al. |
| 5,792,038 A | 8/1998 | Hlavinka |
| 5,807,492 A | 9/1998 | Brown et al. |
| 5,833,866 A | 11/1998 | Brown |
| 5,837,150 A | 11/1998 | Langley et al. |
| 5,840,502 A | 11/1998 | Van Vlasselaer |
| 5,853,382 A | 12/1998 | Kingsley et al. |
| 5,855,773 A | 1/1999 | Lasota |
| 5,858,251 A | 1/1999 | Borchardt |
| 5,858,253 A | 1/1999 | Holm |
| 5,876,321 A | 3/1999 | Hlavinka et al. |
| 5,879,280 A | 3/1999 | Hlavinka et al. |
| 5,882,289 A | 3/1999 | Sakota et al. |
| 5,904,645 A | 5/1999 | Hlavinka |
| 5,906,319 A | 5/1999 | Crowl |
| 5,906,570 A | 5/1999 | Langley et al. |
| 5,906,598 A | 5/1999 | Giesler et al. |
| 5,913,768 A | 6/1999 | Langley et al. |
| 5,939,319 A | 8/1999 | Hlavinka et al. |
| 5,951,877 A | 9/1999 | Langley et al. |
| 5,961,842 A | 10/1999 | Min et al. |
| 5,964,690 A | 10/1999 | Wright et al. |
| 5,980,757 A | 11/1999 | Brown et al. |
| 5,980,760 A | 11/1999 | Min et al. |
| 5,989,177 A | 11/1999 | West et al. |
| 6,027,655 A | 2/2000 | Holm |
| 6,027,657 A | 2/2000 | Min et al. |
| 6,051,146 A | 4/2000 | Green et al. |
| 6,053,856 A | 4/2000 | Hlavinka |
| 6,063,297 A | 5/2000 | Antanavich et al. |
| 6,071,422 A | 6/2000 | Hlavinka |
| 6,099,491 A | 8/2000 | Headley et al. |
| 6,102,883 A | 8/2000 | Kingsley et al. |
| 6,200,287 B1 | 3/2001 | Keller et al. |
| 6,284,142 B1 | 9/2001 | Muller |
| 6,296,602 B1 | 10/2001 | Headley |
| 6,315,707 B1 | 11/2001 | Smith et al. |
| 6,322,488 B1 | 11/2001 | Westberg et al. |
| 6,334,842 B1 | 1/2002 | Hlavinka et al. |
| 6,354,986 B1 | 3/2002 | Hlavinka et al. |
| 6,361,518 B1 | 3/2002 | Brierton et al. |
| 6,361,700 B2 | 3/2002 | Gates et al. |
| 6,379,322 B1 | 4/2002 | Kingsley et al. |
| 6,387,263 B1 | 5/2002 | Bhaskar et al. |
| 6,398,972 B1 | 6/2002 | Blasetti et al. |
| 6,475,175 B1 | 11/2002 | Rivera et al. |
| 6,497,674 B1 | 12/2002 | Steele et al. |
| 6,511,411 B1 | 1/2003 | Brown |
| 6,524,231 B1 | 2/2003 | Westberg et al. |
| 6,537,445 B2 | 3/2003 | Muller |
| 6,558,307 B2 | 5/2003 | Headley |
| 6,596,180 B2 | 7/2003 | Baugh et al. |
| 6,605,223 B2 | 8/2003 | Jorgensen et al. |
| 6,613,009 B1 | 9/2003 | Bainbridge et al. |
| 6,632,191 B1 | 10/2003 | Headley et al. |
| 6,641,552 B1 | 11/2003 | Kingsley et al. |
| 6,649,072 B2 | 11/2003 | Brandt et al. |
| 6,652,476 B2 | 11/2003 | Langley et al. |
| 6,705,983 B1 | 3/2004 | Rochat |
| 6,709,377 B1 | 3/2004 | Rochat |
| 6,730,055 B2 | 5/2004 | Bainbridge et al. |
| 6,736,768 B2 | 5/2004 | Felt et al. |
| 6,752,777 B1 | 6/2004 | Takegi et al. |
| 6,849,039 B2 | 2/2005 | Min et al. |

| | | |
|---|---|---|
| 7,166,231 B2 | 1/2007 | Westberg et al. |
| 7,297,272 B2 | 11/2007 | Min et al. |
| 2001/0048892 A1 | 12/2001 | Bainbridge et al. |
| 2001/0051569 A1 | 12/2001 | Headley |
| 2002/0020680 A1 | 2/2002 | Jorgensen |
| 2002/0033370 A1 | 3/2002 | Bainbridge et al. |
| 2002/0058575 A1 | 5/2002 | Hlavinka et al. |
| 2002/0068674 A1 | 6/2002 | Hlavinka et al. |
| 2002/0068675 A1 | 6/2002 | Felt et al. |
| 2002/0104808 A1 | 8/2002 | Blasetti et al. |
| 2002/0128584 A1 | 9/2002 | Brown et al. |
| 2002/0142909 A1 | 10/2002 | Sakota |
| 2002/0177799 A1 | 11/2002 | Rivera et al. |
| 2003/0052065 A1 | 3/2003 | Rosiello |
| 2003/0066807 A1 | 4/2003 | Suzuki |
| 2003/0102272 A1 | 6/2003 | Brown |
| 2003/0155312 A1 | 8/2003 | Ivansons et al. |
| 2003/0181305 A1 | 9/2003 | Briggs et al. |
| 2003/0191005 A1 | 10/2003 | Coelho et al. |
| 2003/0195455 A1 | 10/2003 | Bainbridge et al. |
| 2003/0199803 A1 | 10/2003 | Robinson et al. |
| 2003/0205538 A1 | 11/2003 | Dorian et al. |
| 2003/0211927 A1 | 11/2003 | Cantu et al. |
| 2003/0222029 A1 | 12/2003 | Muller |
| 2003/0233064 A1 | 12/2003 | Arm et al. |
| 2004/0026341 A1 | 2/2004 | Hogberg et al. |
| 2004/0079707 A1 | 4/2004 | Smith et al. |
| 2004/0082459 A1 | 4/2004 | Min et al. |
| 2004/0104182 A1 | 6/2004 | Holmes et al. |
| 2004/0147865 A1 | 7/2004 | Cianci et al. |
| 2006/0032817 A1 | 2/2006 | Westberg et al. |
| 2008/0087601 A1 | 4/2008 | Min et al. |
| 2008/0087614 A1 | 4/2008 | Min et al. |

FOREIGN PATENT DOCUMENTS

| | | |
|---|---|---|
| EP | 363 119 A2 | 4/1990 |
| EP | 1 043 072 A1 | 10/2000 |
| WO | WO 89/00084 | 1/1989 |
| WO | WO 98/04938 | 2/1998 |
| WO | WO 98/22165 | 5/1998 |
| WO | WO/98/50163 | 11/1998 |

OTHER PUBLICATIONS

PCT/US2004/042330 International Search Report dated May 17, 2005, Baxter International.
Supplemental European Search Report for European Patent Application No. 03774903.3, dated Feb. 19, 2010.

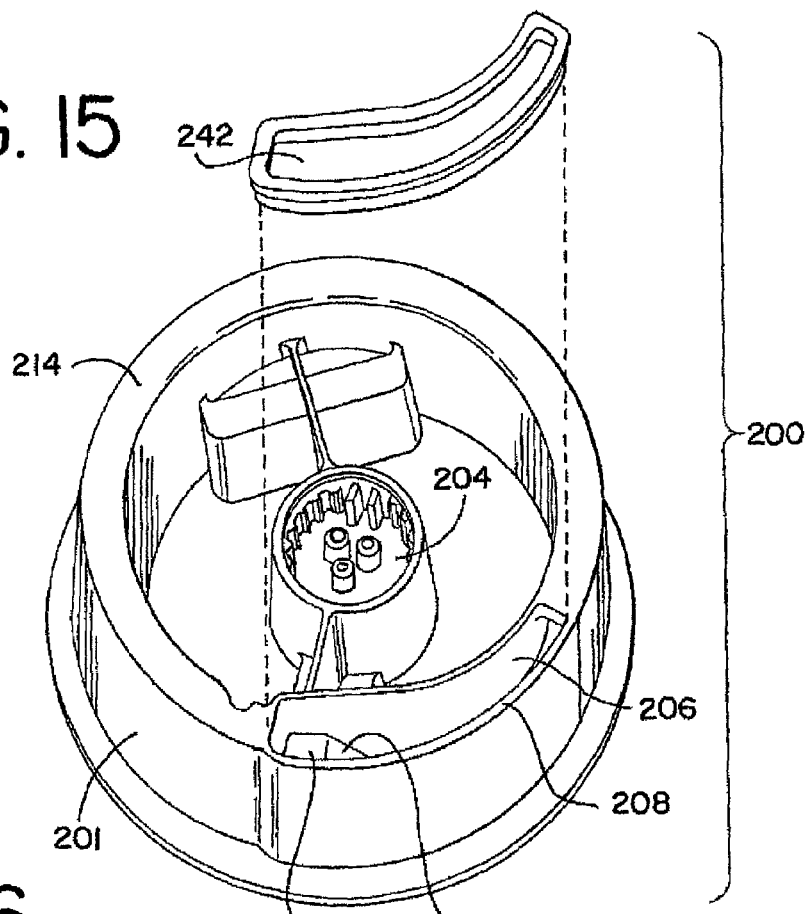
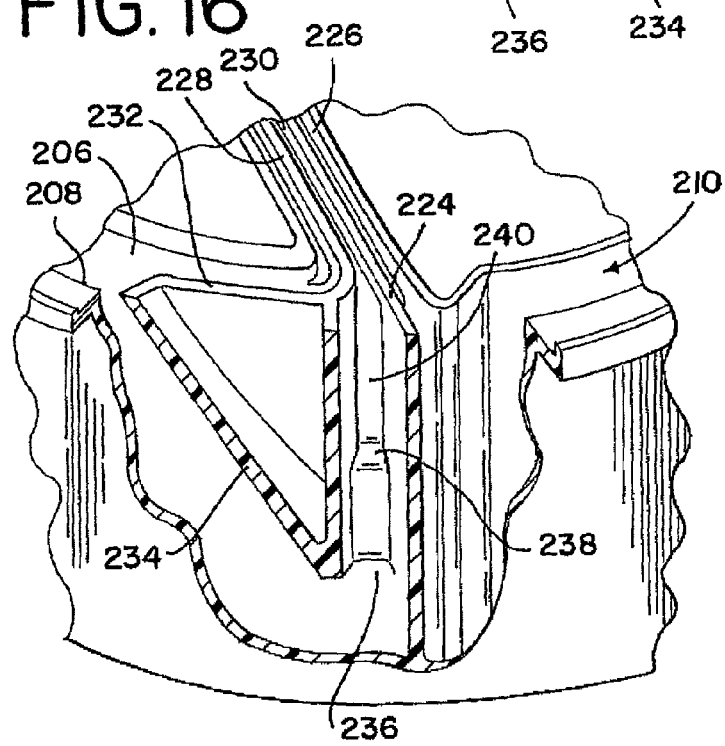

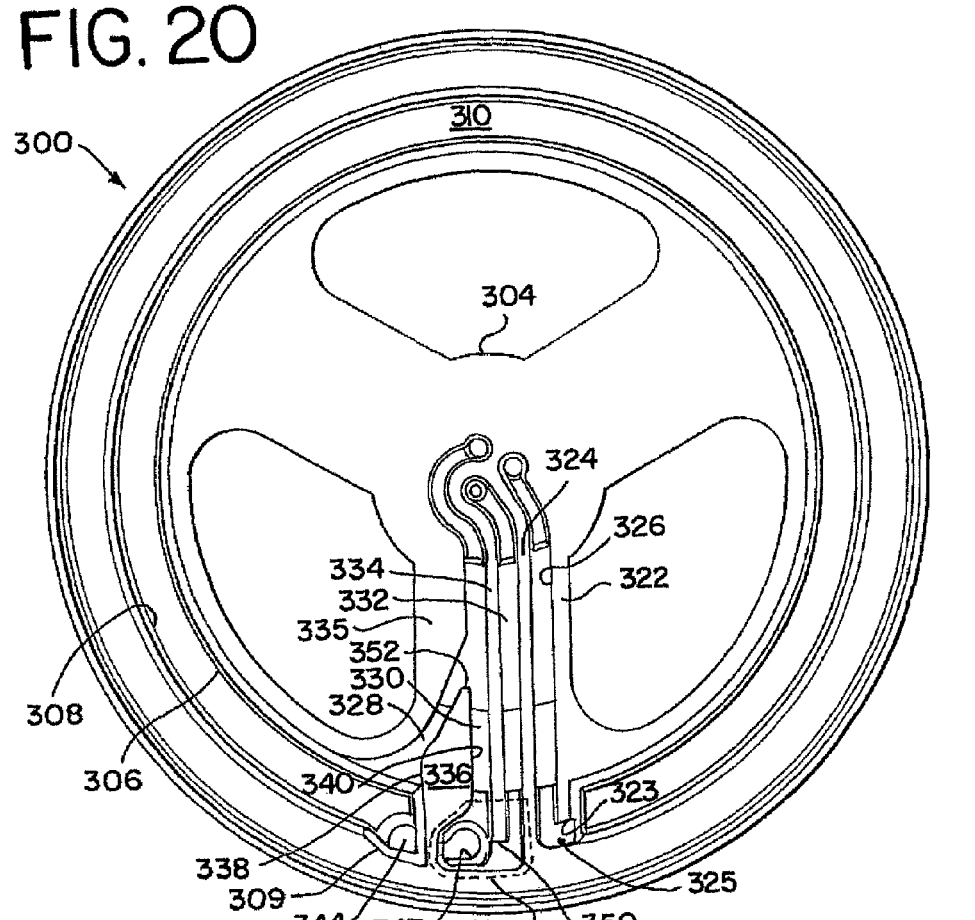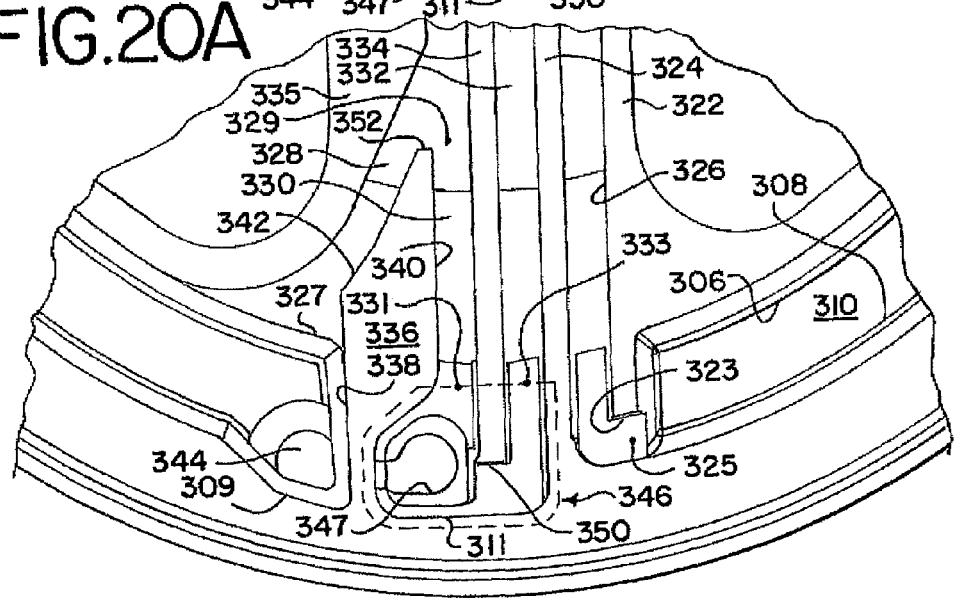

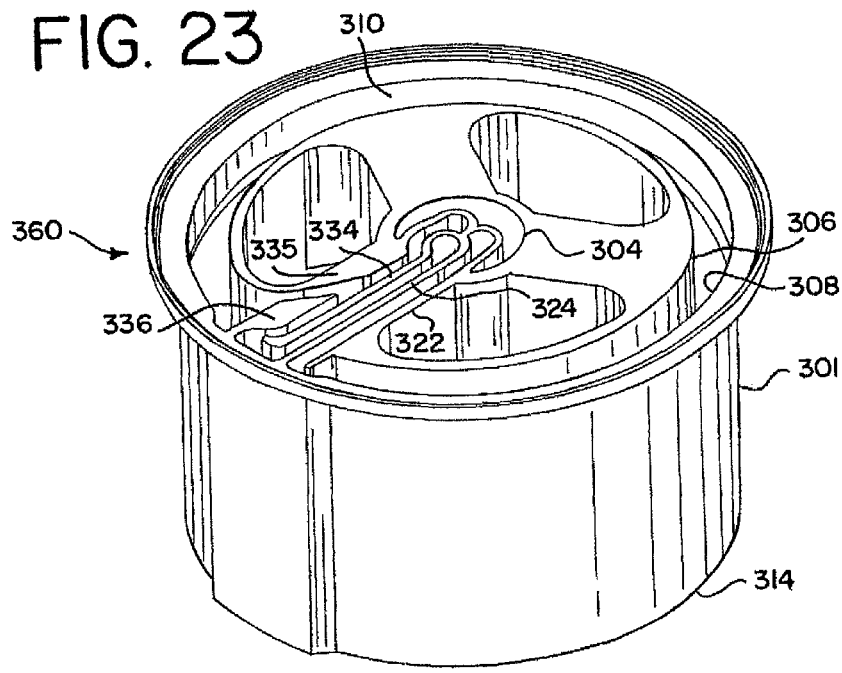
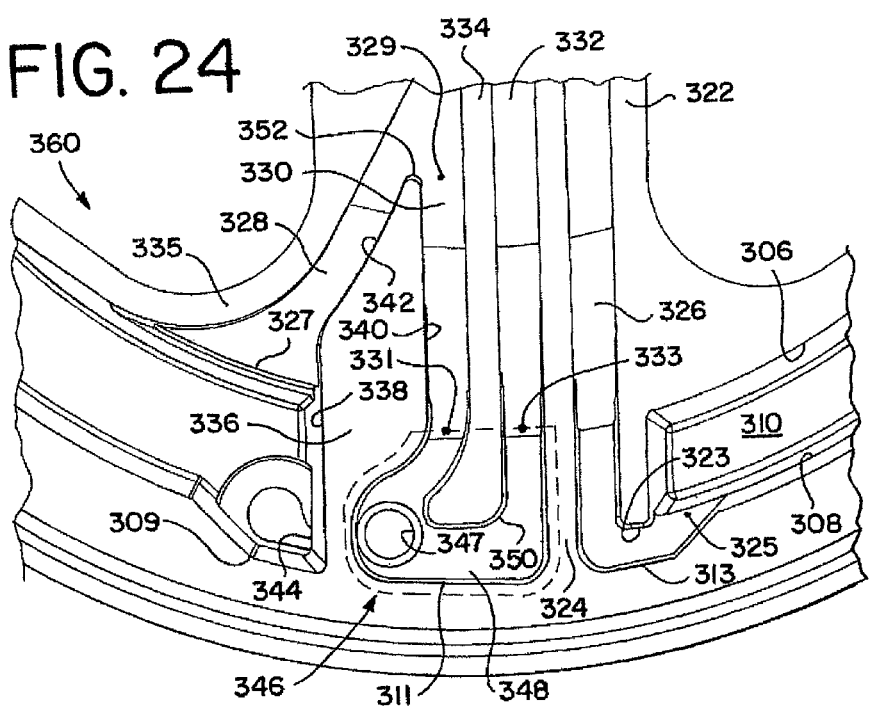

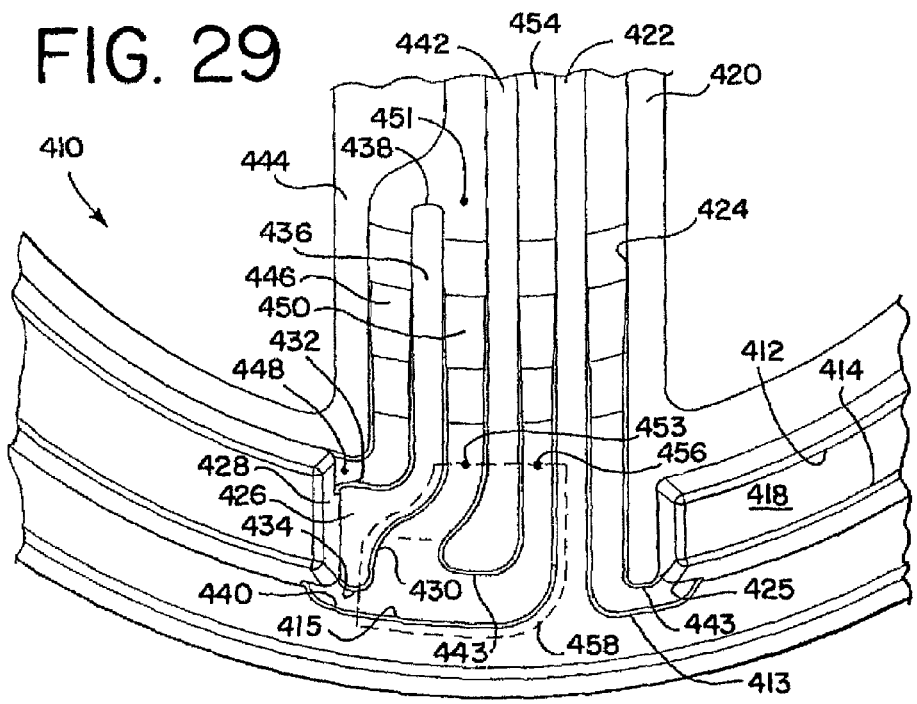
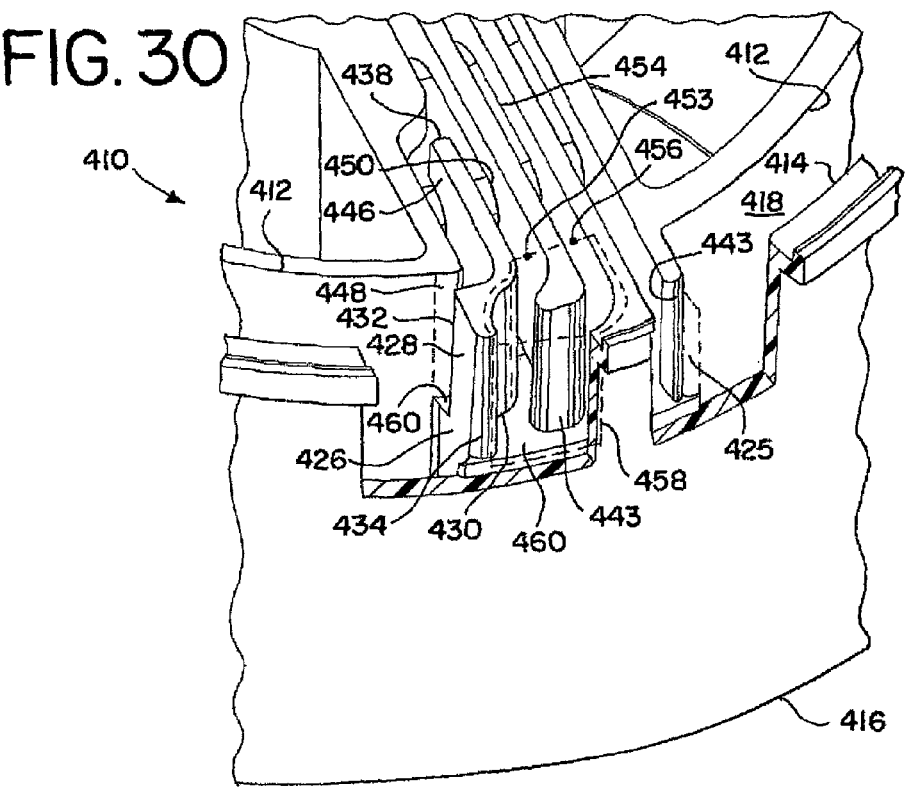

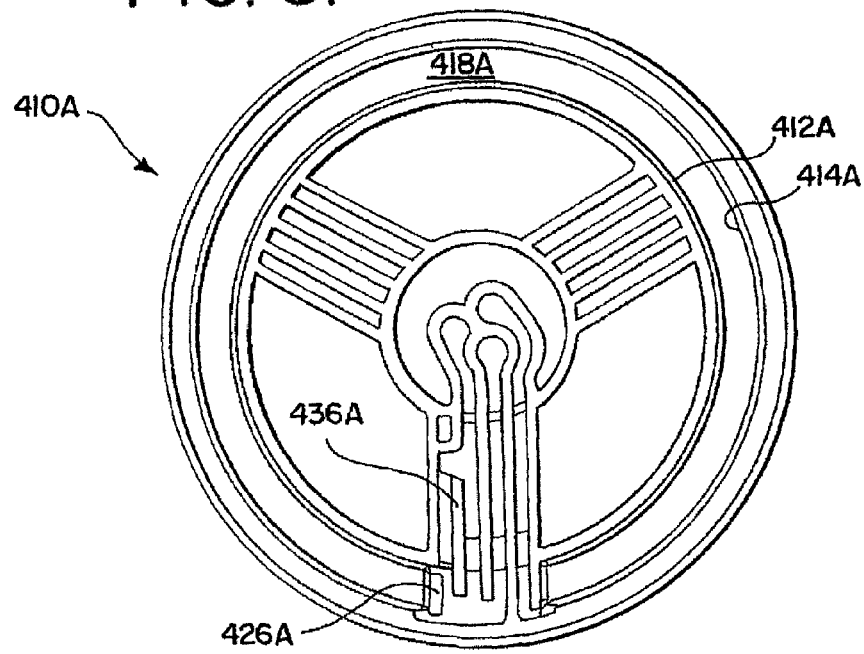
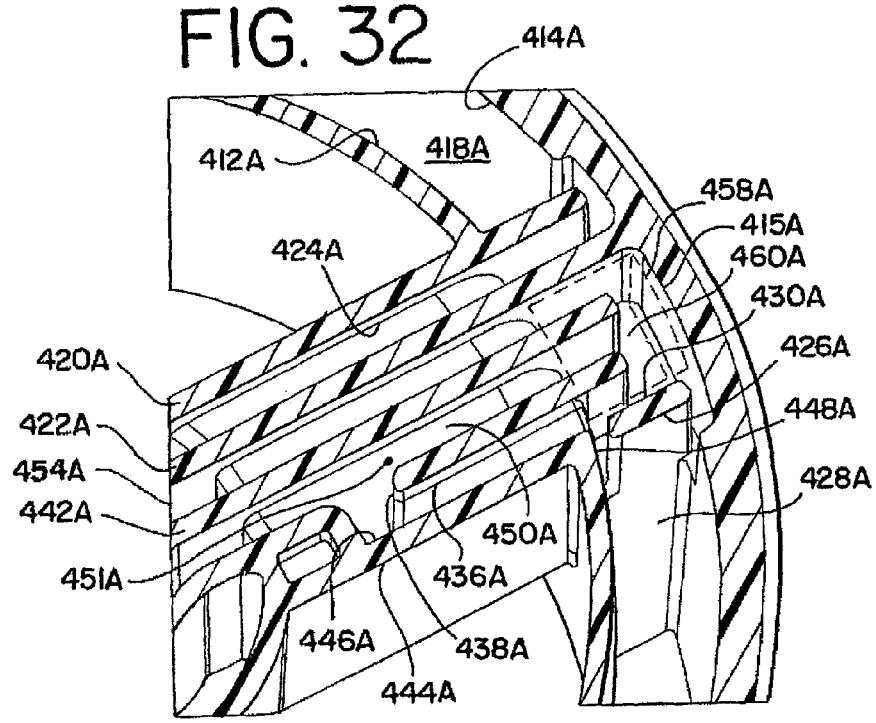

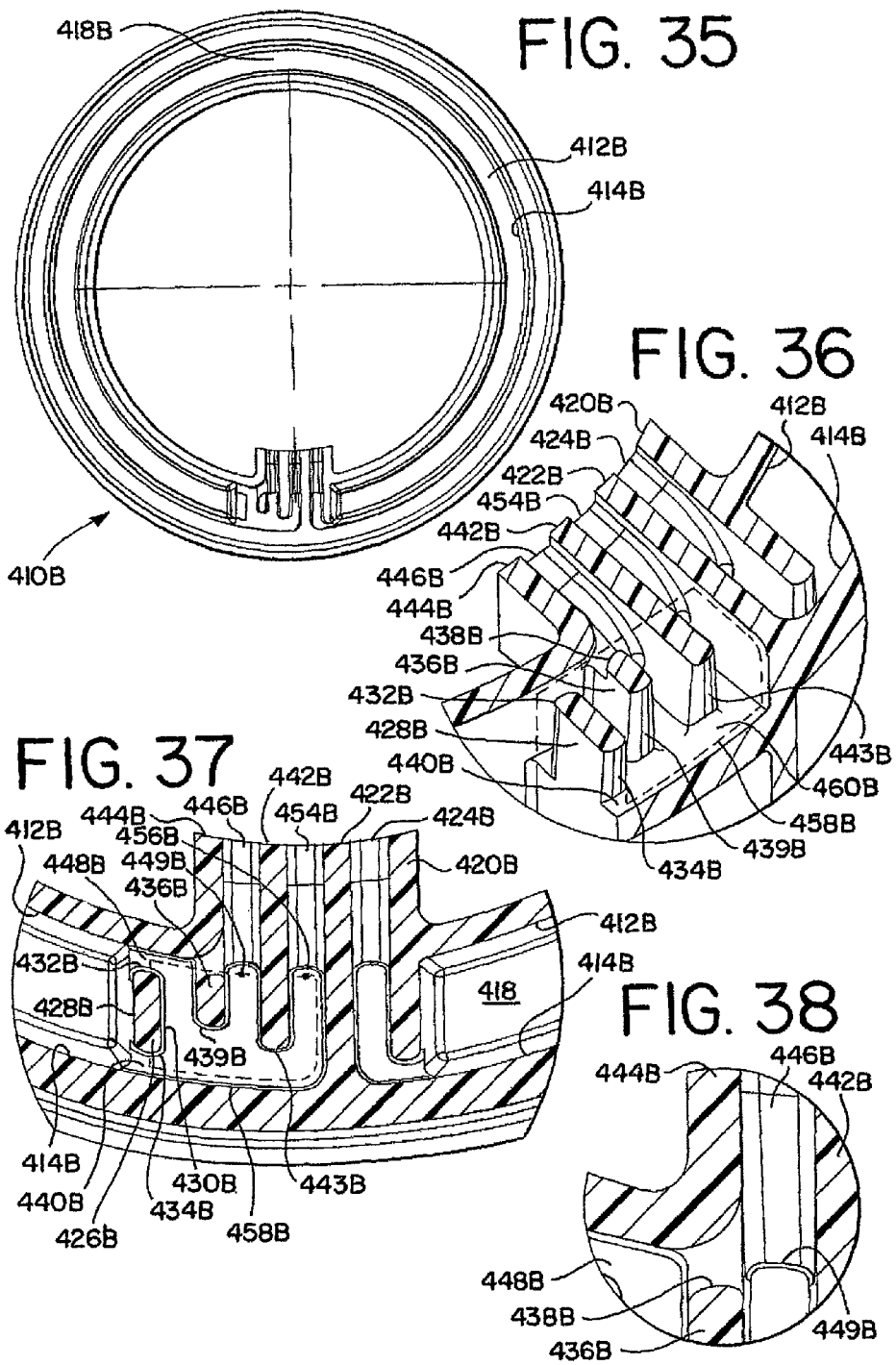

SEPARATION APPARATUS AND METHOD

RELATED APPLICATIONS

This application is a continuation of application Ser. No. 11/927,033, filed on Oct. 29, 2007 now abandoned, which is a continuation of application Ser. No. 10/827,603, filed on Apr. 19, 2004, now U.S. Pat. No. 7,297,272, which is a continuation-in-part of application Ser. No. 10/279,765 filed Oct. 24, 2002, now U.S. Pat. No. 6,849,039 and entitled "Blood Processing Systems and Methods for Collecting Plasma Free or Essentially Free of Cellular Blood Components," and claims the benefit of U.S. Provisional Application Ser. No. 60/533,820, filed Dec. 31, 2003, which applications are incorporated by reference herein.

BACKGROUND

The present invention relates in general to apparatus and methods for separating biological fluids, such as blood or blood components or other fluids, into one or more components.

The separation of biological fluid such as whole blood and blood components into its constituent components for various applications is well known. Many commercially available separation systems are based on principles of centrifugation, which separates the fluid components according to density. Various devices and systems are known that employ centrifugal separation of blood or blood components including the CS-3000®, Amicus®, ALYX®, separators marketed by Baxter Healthcare Corporation of Deerfield, Ill., the Spectura®, and Trima® separators by Gambro BCT of Lakewood, Colo., the AS104 from Fresenius Homecare of Redmond, Wash., and the V-50 and other models from Haemonetics Corporation of Braintree, Mass. Various centrifuge devices are also disclosed in U.S. Pat. No. 6,325,775, Published PCT Application Nos. PCT/US02/31317; PCT/US02/31319; PCT/US03/33311 and PCT/US03/07944, and U.S. Published Patent Applications 20020094927 and 20020077241. Each of these patent and patent applications are hereby incorporated by reference herein.

Although centrifugal blood separator devices are thus well known, efforts continue to develop devices that are smaller, lighter, more portable, versatile and/or efficient in the separation and collection of one or more different components of blood or other biological fluids.

SUMMARY OF THE INVENTION

The present invention includes apparatus and methods for separation of a biological fluid, such as whole blood, and optional collection of at least one of the fluid components.

In accordance with one embodiment of the present invention, a separation channel is provided for rotation about an axis. The separation channel includes radially spaced apart inner and outer side wall portions and an end wall portion. The channel has an axial length relative to the axis. An inlet is provided to convey fluid into the channel and a barrier is located in the channel intermediate of the inner and outer side wall portions. The barrier includes both upstream and downstream sides and includes a first flow path which communicates between the upstream and downstream sides. The separation channel further includes a collection region which is located downstream of the barrier and in fluid communication with the first flow path. The collection region is defined at least in part by an end wall portion which is axially spaced from the end wall portion of the channel. Additionally, first and second openings communicate with the collection region so as to allow flow of one or more fluid components, such as blood components, from the collection region.

In another embodiment of the invention, a section of an outer side wall portion of the channel is located in the vicinity of a barrier and is positioned radially outward of the outer side wall portion that is upstream of such section.

In a further embodiment of the separation channel, a barrier extends to an outer side wall portion and joins the outer side wall portion along a substantial portion of the axial length of the channel. A first flow path allows fluid communication between the upstream and downstream sides of the barrier.

In yet a further embodiment of the separation channel, a barrier may extend to a radial position which is inward of the radial location of an inner side wall portion.

An additional embodiment of the separation channel includes a first flow path which communicates between the upstream and downstream sides of a barrier and further includes first and second exit flow paths. The first exit flow path communicates with the channel upstream of the barrier while a second exit flow path communicates with the channel downstream of the barrier. The first and second flow paths join at a location radially inward of an inner wall portion of the channel.

In addition, another separation channel may provide that a plurality of exit openings from the channel are located downstream of a barrier. In this respect, the channel is free of an exit opening upstream of the barrier inasmuch as fluid components are not allowed to exit the channel at a location which is upstream of the barrier. A first fluid flow path allows communication between the upstream and downstream sides of the barrier but does not provide an exit flow path to outside of the channel.

In a still further embodiment of the separation channel, a barrier wall extends to a radially outer side wall portion of the channel. A first flow path communicates between the upstream and downstream sides of the barrier and is spaced from one of the opposed end wall portions of the channel. The separation channel further includes a second flow path which communicates between the upstream and downstream sides of the barrier, which second flow path is defined by a surface of the other end wall portion.

Although described later in terms of certain preferred embodiments, it should be understood that the separation channels of the present invention are not limited to the identical structures shown. For example, a separation channel may comprise a reusable platen, bowl or rotor into which a disposable flexible, rigid or semi-rigid liner is placed so that blood flows through the liner and does not contact the reusable portion. In such case, the configuration of the channel platen, bowl or rotor defines the shape of fluid flow path and the disposable liner assumes a corresponding shape during operation. Examples of such may be seen in the CS-3000®, Amicus® and Spectra® centrifugal separation systems. Alternatively, the separation channel may be entirely disposable. For example, the channel may be formed of rigid plastic having a pre-formed shape through which the blood or other biological fluid is processed. Of course, the channel could be entirely reusable, in which case it would need to be cleaned and possibly sterilized between uses—an inconvenient and time consuming procedure. It should be understood that the separation channel and methods described and claimed are intended to have a broad interpretation that includes all of the more specific structures, such as those mentioned above, in which it may find commercial application.

The separation channels or chambers described herein may be used for a variety of biological fluid separation and collection procedures. By way of example and not limitation, one of such separation methods comprises the steps of introducing a first fluid, such as whole blood, which comprises at least first and second components, e.g., blood components, having generally different density into a centrifugal field and allowing an interface to form between at least portions of the first and second components. The method includes removing a second fluid from one side of the interface and a third fluid from the other side of the interface, combining at least a portion of the second fluid with the first or third fluid and reintroducing the combined fluids into the centrifugal field, and removing at least one of the second or third fluid from the centrifugal field.

When the above method is applied to whole blood (first fluid), the second fluid may substantially comprise plasma and the third fluid may substantially comprise red cells. The combined second and first or third fluid may have a hematocrit which is approximately between 20 and 40 percent. The portion of the plasma which is removed from one side of the interface may include substantial numbers of platelets.

In accordance with another method of the present invention, the method includes introducing a first fluid, such as whole blood, which comprises first and second components having generally different density into a centrifugal field; allowing an interface to form between at least portions of the first and second fluid components; decreasing the force of the centrifugal field (such as by reducing the rotational field of separation chamber containing the fluid); and removing the first fluid component from the centrifugal field after the force of the centrifugal field is decreased.

Some or all of the above steps of this method may be repeated to enhance efficiency. For example, the step of removing the fluid component may be repeated so as to provide several collection cycles. The above method may have particular application in the collection of platelets from whole blood wherein the first fluid component comprises plasma which includes platelets.

A further method of the present invention provides for forming and reforming of the interface between the fluid components of different density. This method includes the steps of introducing a first fluid, such as whole blood which has at least first and second components of generally different density; allowing an interface to form between at least portions of the first and second components, such as between plasma and red cells of whole blood; sequentially and repeatedly removing fluid from the centrifugal field from one side of the interface and allowing the interface to reform.

When the method is applied to whole blood, the fluid which is removed from the centrifugal field comprises plasma and platelets. In particular, the fluid may comprise plasma which is rich in platelet concentration. The method may be performed so that the step of removing the fluid from one side of the interface is repeated at least two times.

The method may further include moving the interface radially inward so that the interface itself is in proximity with an aperture or opening, through which the plasma or platelets are removed. Where the step of removing is performed at least twice, it is contemplated that the interface may be returned to its initial location prior to moving it to proximity with the aperture.

An additional method of the present invention includes a method for processing whole blood, which may serve to reduce the amount of time that the donor or other human subject or blood source is connected to the blood separation device. The method includes connecting a blood source to a separation device; introducing blood into a centrifugal field created by the device; and allowing an interface to develop between at least two blood components. The method further includes: removing a first blood component from the centrifugal field from one side of the interface; removing a second blood component from the centrifugal field from the other side of the interface; storing at least one of the first and second blood components; returning, at least in part, the other of the first and second blood components to the blood source; and withdrawing additional blood from the blood source. After the additional blood has been drawn, the blood source is disconnected, and the steps of introducing the blood into the centrifugal field and removing the first and second blood components are repeated. The first and second blood components that have been removed from the centrifugal field may be stored for later use as desired.

BRIEF DESCRIPTION OF THE DRAWINGS

FIG. 15 is a bottom perspective view of the blood processing chamber shown in FIG. 14.

FIG. 16 is an enlarged side perspective view of an interior region in the blood processing chamber shown in FIG. 14, showing a barrier having a tapered surface that directs red blood cells from the separation zone in a path separate from plasma.

FIG. 20 is a top view of the interior of the chamber of FIG. 19.

FIG. 20A is an enlarged partial top view of a collection region of the chamber of FIG. 20.

FIG. 23 is a perspective view of the interior of a fourth embodiment of the chamber of a type shown in FIG. 7 with the top end wall portion shown removed, which chamber may be used to perform a fluid separation and collection procedure using the device shown in FIGS. 5 and 6.

FIG. 24 is a partial top view of the chamber of FIG. 23.

FIG. 29 is a partial top view of the chamber of FIG. 28.

FIG. 30 is a partial perspective view of the chamber of FIG. 28 with portions of the chamber being shown in section.

FIG. 31 is a top view of the interior of an eighth embodiment of the chamber of the type shown in FIG. 7, the interior of the chamber being configured to perform various fluid separation and collection procedures using the device shown in FIGS. 5 and 6.

FIG. 32 is an enlarged partial left perspective view of the chamber of FIG. 31.

FIG. 35 is a top view of the interior of a ninth embodiment of the chamber of the type shown in FIG. 7, which is configured to perform various fluid separation and collection procedures using the device shown in FIGS. 5 and 6.

FIG. 36 is an enlarged partial perspective view of the chamber of FIG. 35 with a portion of the outer side wall portion being shown removed.

FIG. 37 is an enlarged partial top view of the chamber of FIG. 35.

FIG. 38 is a further enlarged top view of a portion of the chamber shown in FIG. 37.

DESCRIPTION OF THE PREFERRED EMBODIMENTS

Figure 1:
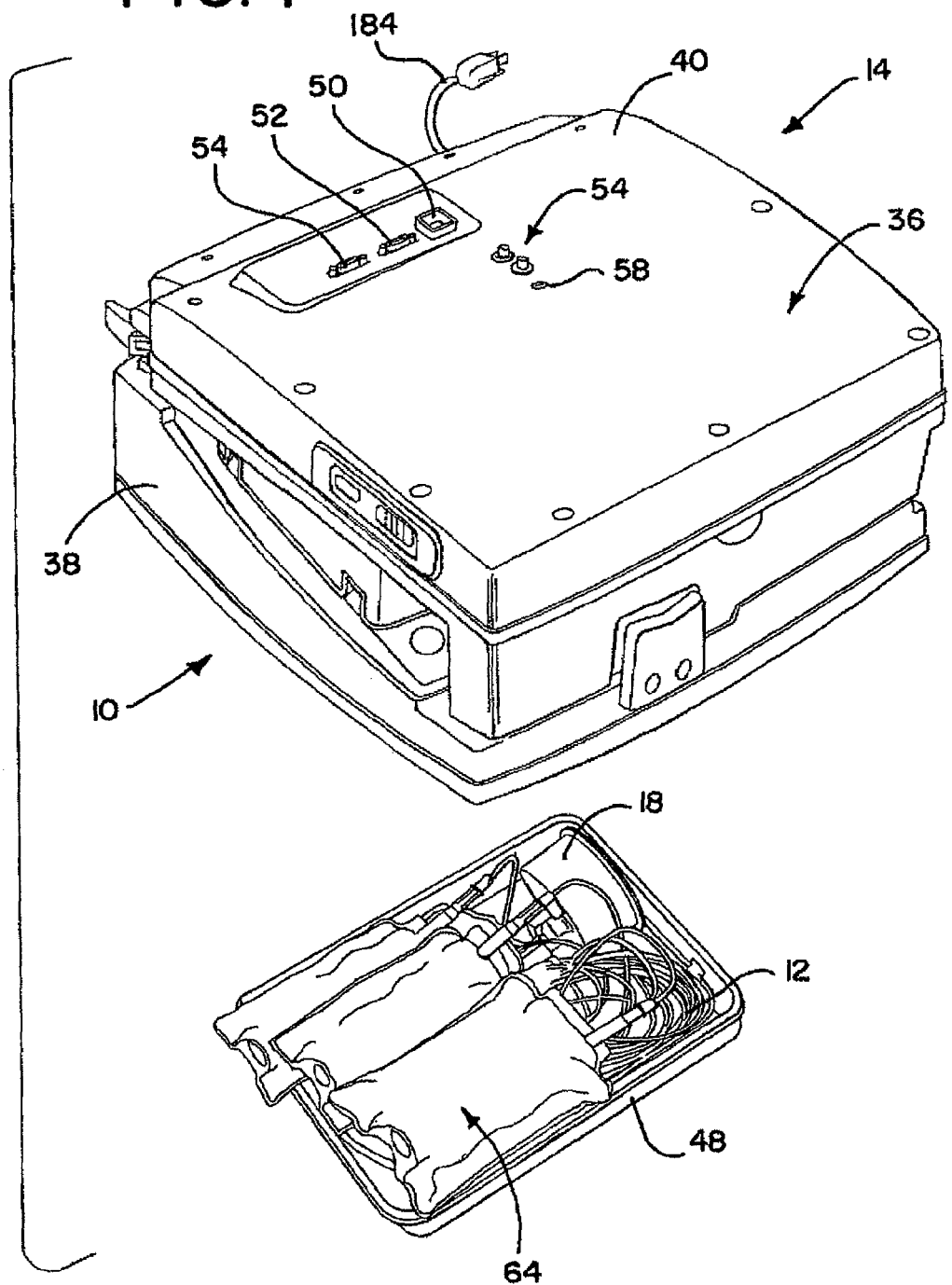
FIG. 1 is a perspective view of a fluid processing system, ideally suited for blood processing, comprising a blood processing device (shown in a closed condition for transport and storage) and a disposable liquid and blood flow set, which interacts with the blood processing device to cause separation and collection of one or more blood components (shown packaged in a tray for transport and storage before use).

FIG. 1 shows a liquid processing system 10 that embodies the features of the invention. The system 10 can be used for processing various fluids. The system 10 is particularly well suited for processing whole blood and other suspensions of biological cellular materials. Accordingly, the illustrated embodiment shows the system 10 used for this purpose.

I. System Overview

The system 10 includes two principal components. These are: (i) a blood processing device 14—shown in FIG. 1 in a closed condition for transport and storage, and in FIGS. 2 and 3 in an opened condition for operation; and (ii) a liquid and blood flow set 12, which interacts with the blood processing device 14 to cause separation and collection of one or more blood components—the set 12 being shown in FIGS. 1 and 4 packaged in a tray 48 for transport and storage before use, and in FIGS. 5 and 6 removed from the tray 48 and mounted on the blood processing device 14 for use. Although portions of the system 10 will be described further, details of the system are described in one or more of the above-identified patents or patent applications which have been incorporated by reference herein.

A. The Processing Device

The blood processing device 14 is intended to be a durable item capable of long term use. In the illustrated and preferred embodiment, the blood processing device 14 is mounted inside a portable housing or case 36. The case 36 presents a compact footprint, suited for set up and operation upon a table top or other relatively small surface. The case 36 is also intended to be transported easily to a collection site.

Figure 2:
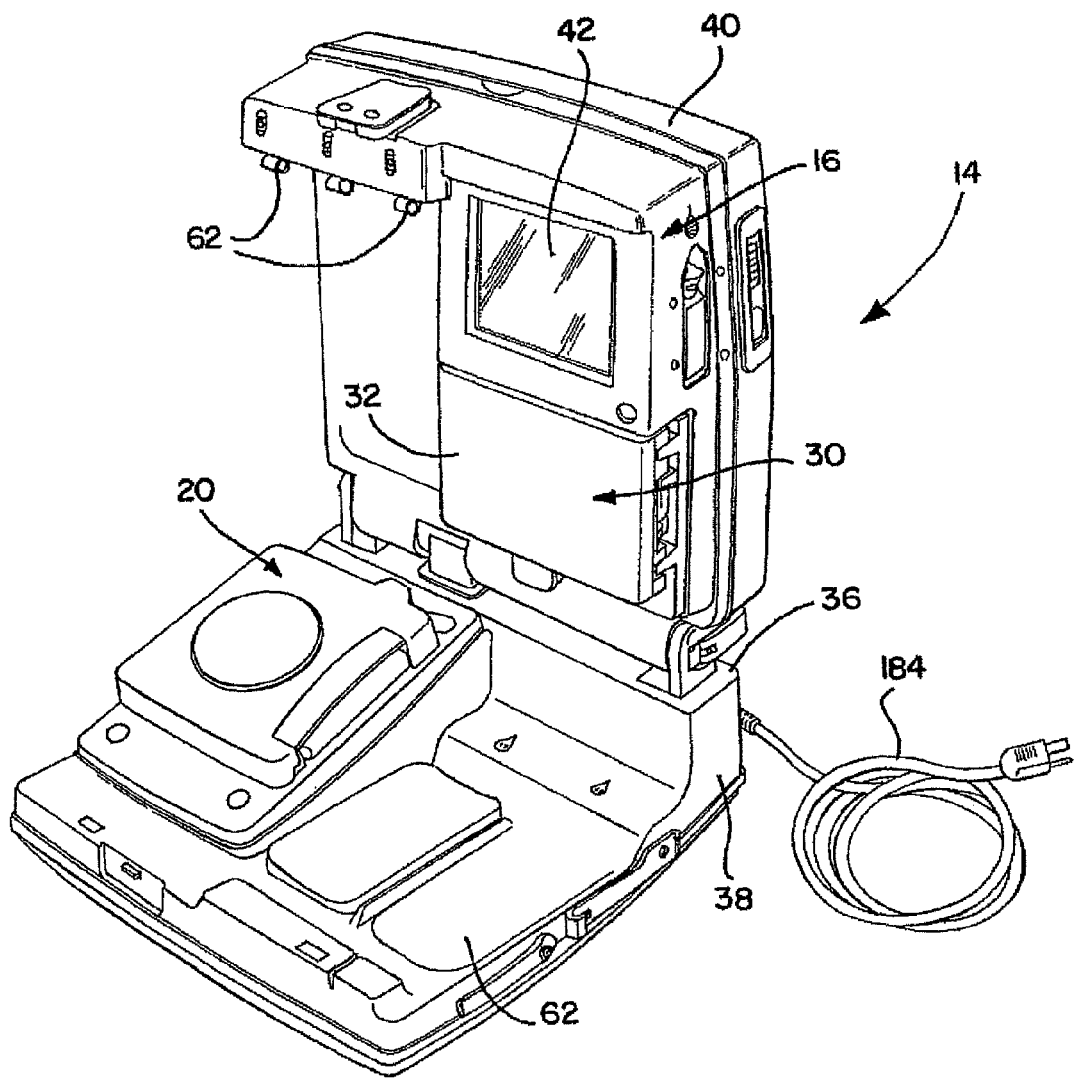
FIG. 2 is a perspective view of the blood processing device shown in FIG. 1, shown in an opened condition for operation.
Figure 3:
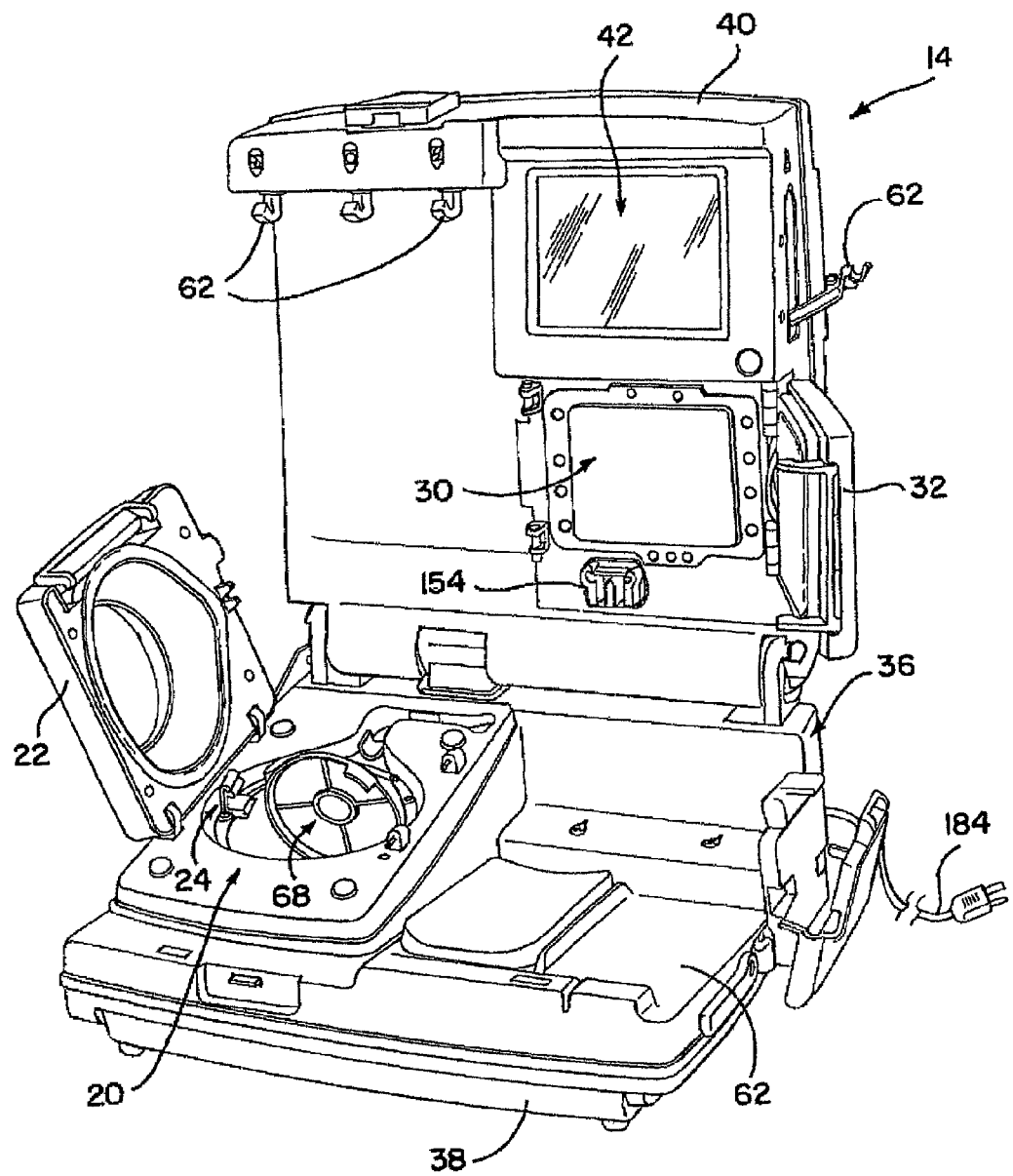
FIG. 3 is a perspective view of the blood processing device shown in FIG. 2, with the centrifugal station open to receive a blood processing chamber and the pump and valve station open to receive a fluid pressure-actuated cassette.
Figure 4:
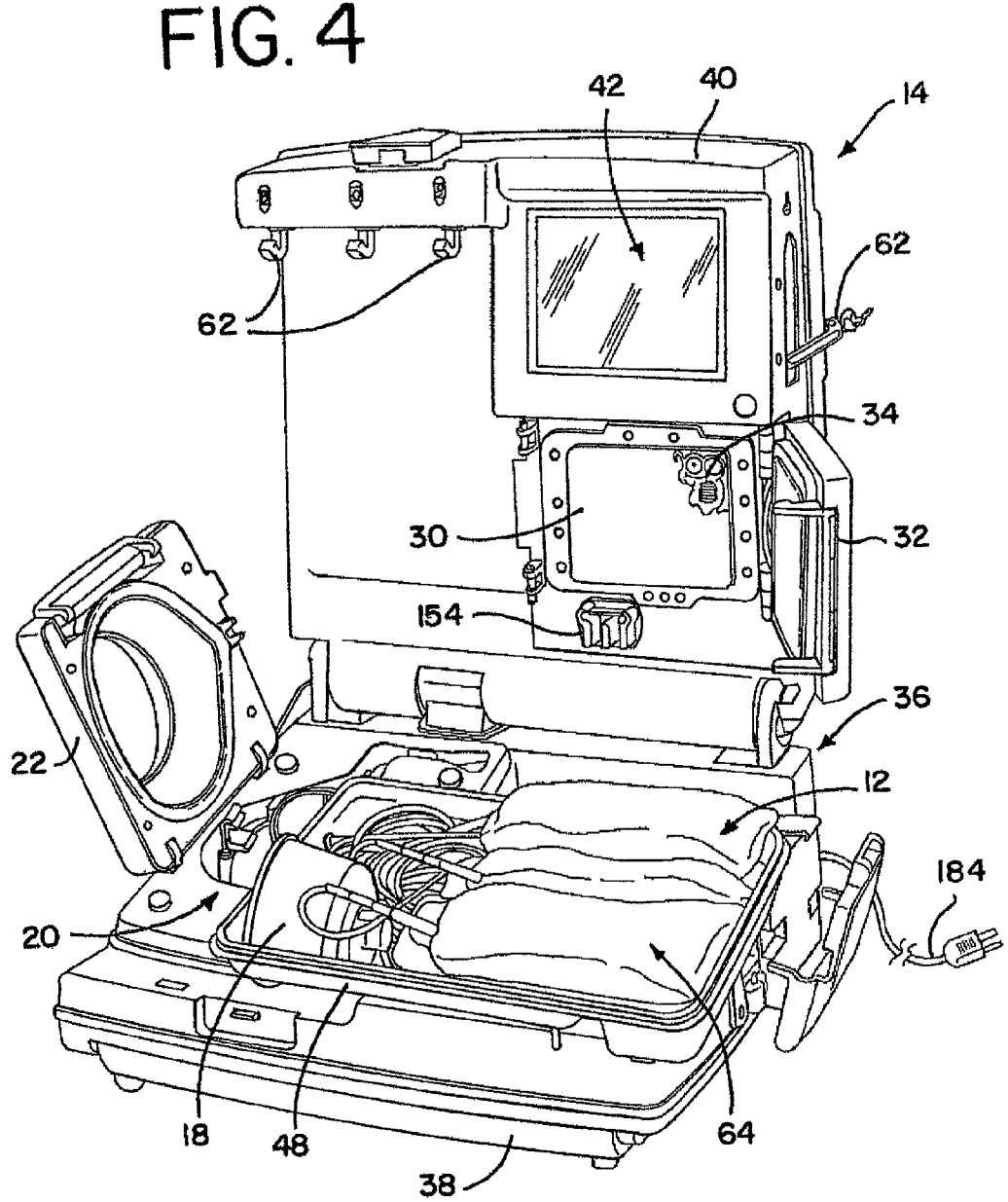
FIG. 4 is a perspective view of the blood processing device shown in FIG. 3, with the tray containing the disposable liquid and blood flow set positioned for loading the flow set on the device.

The case 36 includes a base 38 and a hinged lid 40, which closes for transport (as FIG. 1 shows) and which opens for use (as FIGS. 2 to 4 show). In use, the base 38 is intended to rest in a generally horizontal support surface. The case 36 can be formed into a desired configuration, e.g., by molding. The case 36 is preferably made from a lightweight, yet durable, plastic material.

A controller 16 is carried onboard the device 14. The controller 16 governs the interaction between the components of the device 14 and the components of the flow set 12 to perform a blood processing and collection procedure selected by the operator. In the illustrated embodiment, the controller 16 comprises a main processing unit (MPU), which can comprise, e.g., a Pentium® type microprocessor made by Intel Corporation, although other types of conventional microprocessors can be used. The MPU can be mounted inside the lid 40 of the case 36. A power supply with power cord 184 supplies electrical power to the MPU and other components of the device 14.

Preferably, the controller 16 also includes an interactive user interface 42, which allows the operator to view and comprehend information regarding the operation of the system 10. In the illustrated embodiment, the interface 42 is implemented on an interface screen carried in the lid 40, which displays information for viewing by the operator in alpha-numeric format and as graphical images.

Further details of the controller 16 can be found in Nayak et al, U.S. Pat. No. 6,261,065, which is incorporated herein by reference. Further details of the interface can be found in Lyle et al, U.S. Pat. No. 5,581,687, which is also incorporated herein by reference.

As FIG. 1 shown, the lid 40 can be used to support other input/outputs to couple other external devices to the controller 16 or other components of the device 14. For example, an Ethernet port 50, or an input 52 for a bar code reader or the like (for scanning information into the controller 16), or a diagnostic port 54, or a port 56 to be coupled to a pressure cuff 60 worn by a donor to enhance blood flow rates during blood processing (see, e.g., FIGS. 43-45 and 47-48), or a system transducer calibration port 58, can all be conveniently mounted for access on the exterior of the lid 40, or elsewhere on the case 36 of the device 14.

B. The Flow Set

Figure 5:
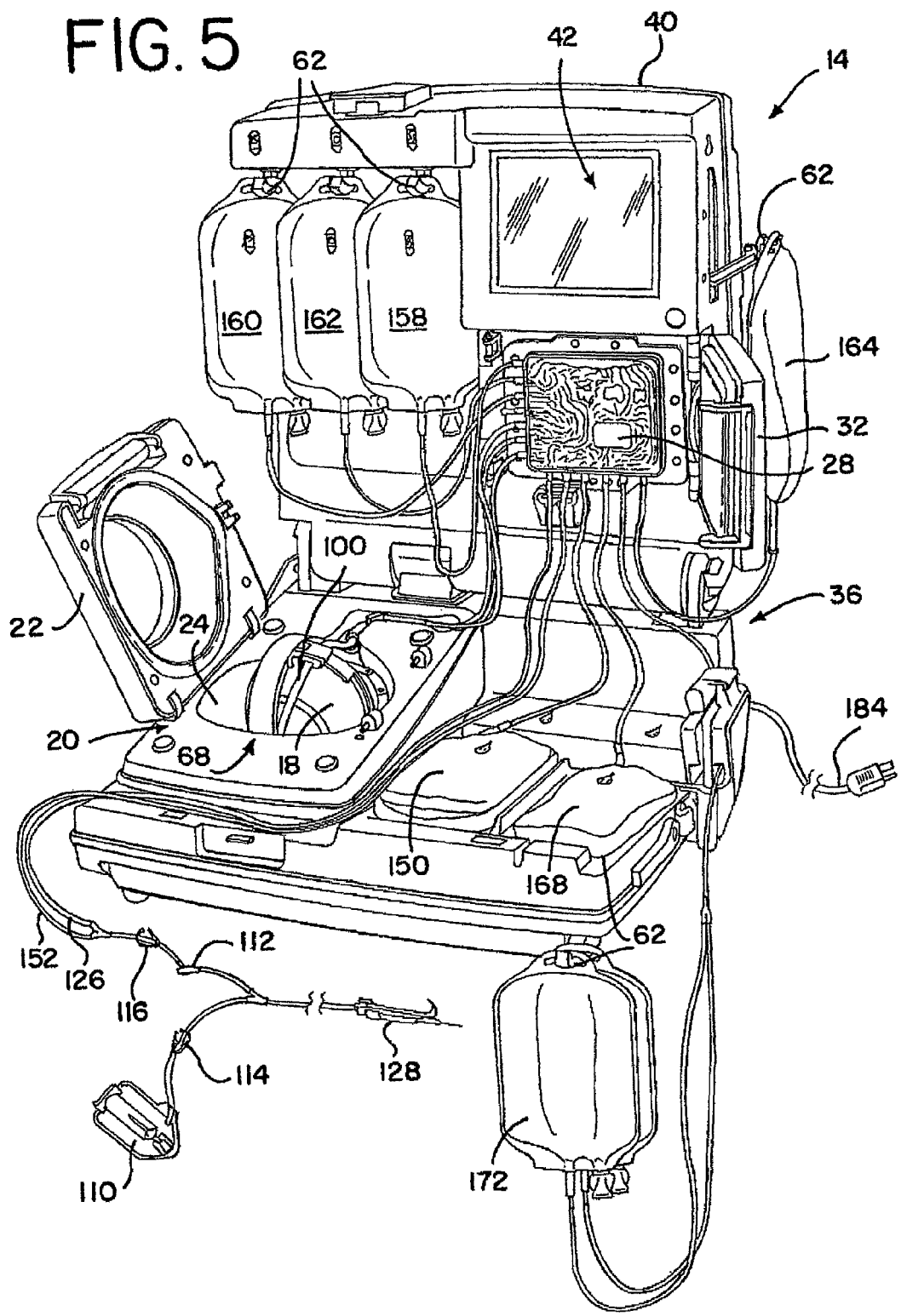
FIGS. 5 and 6 are, respectively, right and left side perspective views of the blood processing device shown in FIG. 2 after the liquid and blood flow set has been loaded onto the device for use.

The flow set 12, is intended to be sterile, single use, disposable item. Before beginning a given blood processing and collection procedure, the operator loads various components of the flow set 12 in association with the device 145 (as FIGS. 4 and 5 show). The controller 16 implements the procedure based upon preset protocols, taking into account other input form the operator. Upon completing the procedure, the operator removes the flow set 12 from association with the device 14. The portion of the set 12 holding the collected blood component or components are removed from the device 14 and retained for storage, transfusion, or further processing. The remainder of the set 12 is removed from the device 14 and discarded.

The flow set includes a blood processing chamber 18, a fluid actuated pump and valve cassette 28, and an array associated processing containers 64 and flow tubing coupled to the chamber 18 and the cassette 28. Several embodiments of the chamber 18 will be identified in greater detail below.

1. The Blood Processing Chamber

In the illustrated embodiment (see FIG. 5), the flow set 12 includes a blood processing chamber 18 designed for use in association with a centrifuge. The processing device 14 includes a centrifuge station 20 (see FIGS. 2 and 3, which receives the processing chamber 18 for use (see FIG. 5).

Figure 6:
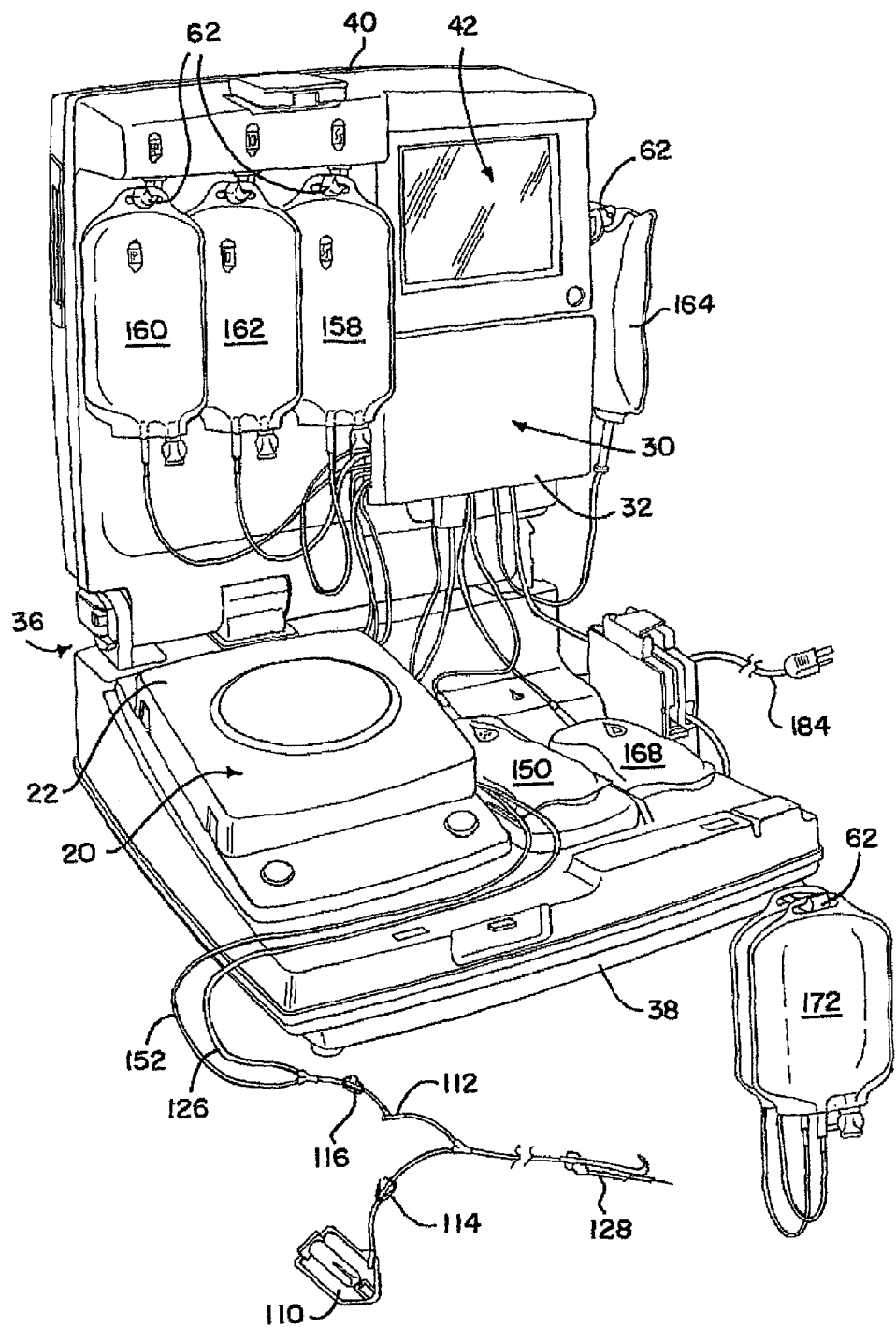

As FIGS. 2 and 3 show, the centrifuge station 20 comprises a compartment 24 formed in the base 38. The centrifuge station 20 includes a door 22. The door 22 opens (as FIGS. 3 and 5 show) to allow loading of the processing chamber 18 into the compartment 24. The door 22 closes (as FIGS. 2 and 6 show) to enclose the processing chamber 18 within the compartment 24 during operation.

The centrifuge station 20 rotates the processing chamber 18. When rotated, the processing chamber 18 centrifugally separates a fluid, preferably whole blood which is received from a donor into component parts, principally, red blood cells, plasma, and intermediate layer called the buffy coat, which is populated by platelets and leukocytes. As will be described later, the configuration of the chamber 18 can vary according to the intended blood separation objectives. Several embodiments of the chamber 18 will be described below.

2. The Fluid Pressure-Actuated Cassette

In the illustrated embodiment, the set 12 also includes a fluid pressure-actuated cassette 28 (see FIG. 5). The cassette 28 provides a centralized, programmable, integrated platform for all the pumping and valving functions required for a given blood processing procedure. In the illustrated embodiment, the fluid pressure comprises positive and negative pneumatic pressure, although other types of fluid pressure can be used.

As FIG. 5 shows, the cassette 28 is mounted for use in a pneumatic actuated pump and valve station 30, which is located in the lid of the 40 of the case 36. The pump and valve station 30 includes a door 32 that is hinged to move between an opened position, exposing the pump and valve station 30 (see FIG. 3) for loading and unloading the cassette 28, and a closed position, enclosing the cassette 28 within the pump and valve station 30 for use (shown in FIG. 6). The pump and valve station 30 includes a manifold assembly 34 (see FIG. 4)

located behind a valve face gasket when the cassette 28 is when mounted on the pump and valve station 30. The pneumatic pressures direct liquid flow through the cassette 28.

3. Blood Processing Containers and Tubing

Referred back to FIGS. 5 and 6, the flow set 16 also includes an array of tubes and containers in flow communication with the cassette 28 and the chamber 18. The arrangement of tubes and containers can vary according to the processing objectives. Representative blood processing procedures and the associated flow sets accommodating such procedures will be described later.

An umbilicus 100 forms a part of the flow set 16. When installed, the umbilicus 100 links the rotating processing chamber 18 with the cassette 28 without need for rotating seals. The umbilicus 100 can be made from rotational-stress-resistant plastic materials, such as Hytrel® copolyester elastomers (DuPont).

Figure 7:
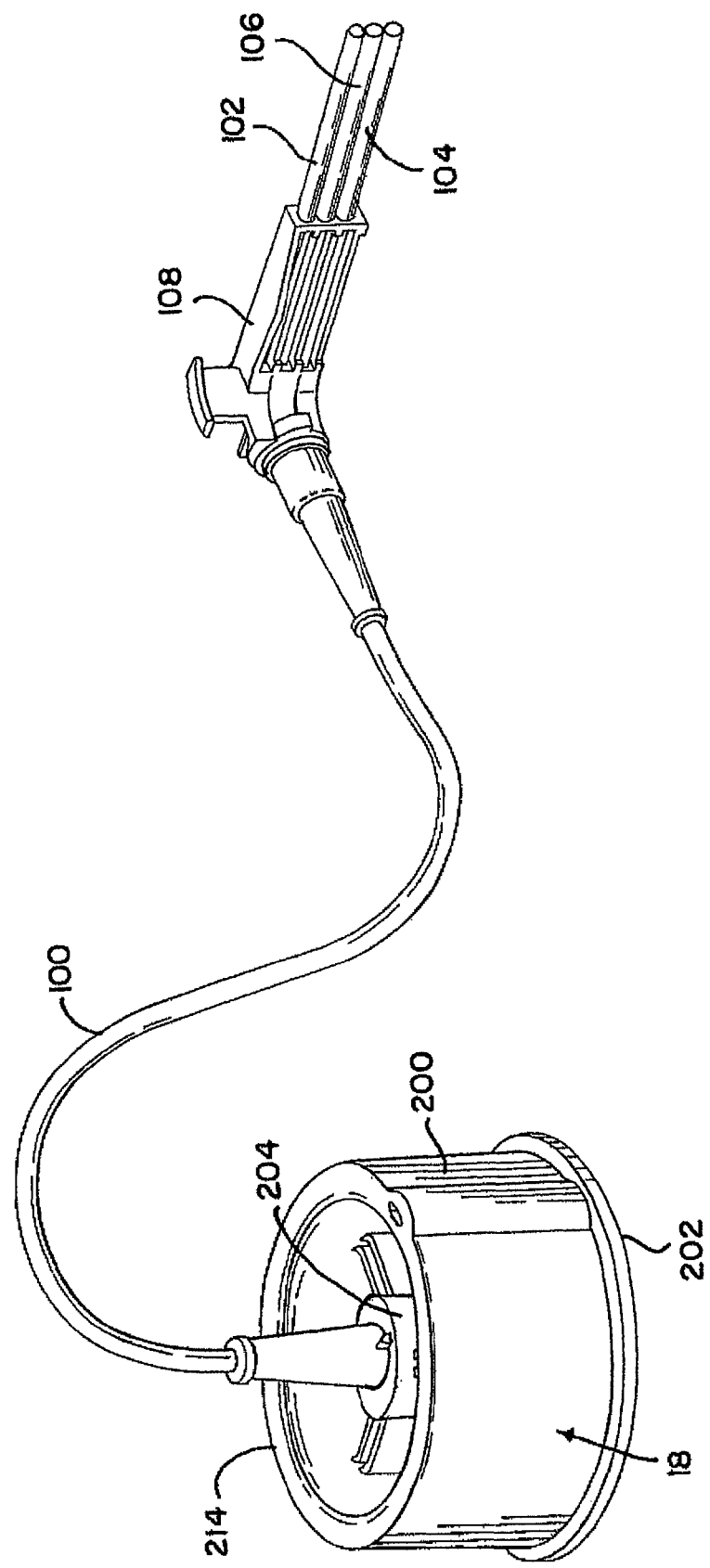
FIG. 7 is a perspective view of the blood processing chamber and attached umbilicus that forms a part of the liquid and blood flow set shown in FIGS. 5 and 6.

Referring now to FIG. 7, tubes 102, 104, and 106 extend from the proximal end of the umbilicus 100. The tube 102 conveys whole blood into the processing chamber 18 for separation. The tubes 104 and 106 convey, respectively, centrifugally separated red blood cells and plasma from the processing chamber 18. The plasma can either be rich or poor in platelets, depending upon the processing objectives.

As FIG. 7 shows, a fixture 108 gathers the tubes 102, 104, and 106 adjacent the umbilicus 100 in a compact, organized, side-by-side array outside the centrifuge station 20. The fixture 108 allows the tubes 102, 104 and 106 to be placed and removed as a group in association with an optical sensing station 46 (see FIGS. 9 and 10), which is located adjacent to the centrifuge station 20 outside the chamber 18.

The optical sensing station 46 optically monitors the presence or absence of targeted blood components (e.g., red blood cells and platelets) in blood conveyed by the tubes 104 and 106. The sensing station 46 provides outputs reflecting the presence or absence of such blood components. This output is conveyed to the controller 16. The controller 16 processes the output and generates signals to control processing events based, in part, upon the optically sensed events. Further details of the operation of the controller to control processing events based upon optical sensing have been described in one or more of the above-identified patent or applications, which have been incorporated herein by reference.

As shown (see FIGS. 5 and 6), the flow set 16 includes a phlebotomy needle 128, through which a door can be coupled to the system 10 for blood processing. In FIGS. 5 and 6, the flow set 16 also includes a blood sampling assembly 110. The blood sampling assembly 110 allows for the collection of one or more samples of the donor's blood at the commencement of a given blood processing procedure, through the phlebotomy needle 128. A conventional manual clamp 114 (e.g., a Roberts Clamp) is provided to control blood flow into the sampling assembly 110.

As also shown in FIGS. 5 and 6, the flow set 16 can include an in-line injection site 112. The injection site 112 allows a technician to introduce saline or another physiologic liquid or medication into the donor, if necessary, using the phlebotomy needle 128, and without requiring an additional needle stick. An additional in-line manual clam 116 is desirably included upstream of the blood sampling assembly 110 and the injection site 112. The flow set 16 may include an appropriate junction such as a T-site, Y-site, V-site or other connector arrangement.

The device further includes one or more weigh stations 62 and other forms of support for containers. The arrangement of these components on the device 14 can, or course, vary depending on the processing objectives. By way of example and not limitation, FIGS. 5 and 6 show collection containers 158, 160, 162 and 172 for in-process (or whole blood), plasma, red blood cells, and leuko-reduced red cells respectively. In FIGS. 5 and 6 other reservoirs or containers 150, 164 and 168 may contain various other fluids for use during the procedure such as, and not limited to anticoagulant, saline and a preservative or storage solution. As blood or liquids are received into and/or dispensed from the containers during processing, the weight stations 62 provide output reflecting weight changes over time. This output is conveyed to the controller 16. The controller 16 processes the incremental weight changes to derive fluid processing volumes. The controller generates signals to control processing events based, in part, upon the derived processing volumes.

C. The Centrifuge Station

The centrifuge station 20 (see FIG. 9) includes a centrifuge assembly 68. The centrifuge assembly 68 is constructed to receive and support the molded processing chamber 18 and umbilicus 100 for use.

Figure 9:
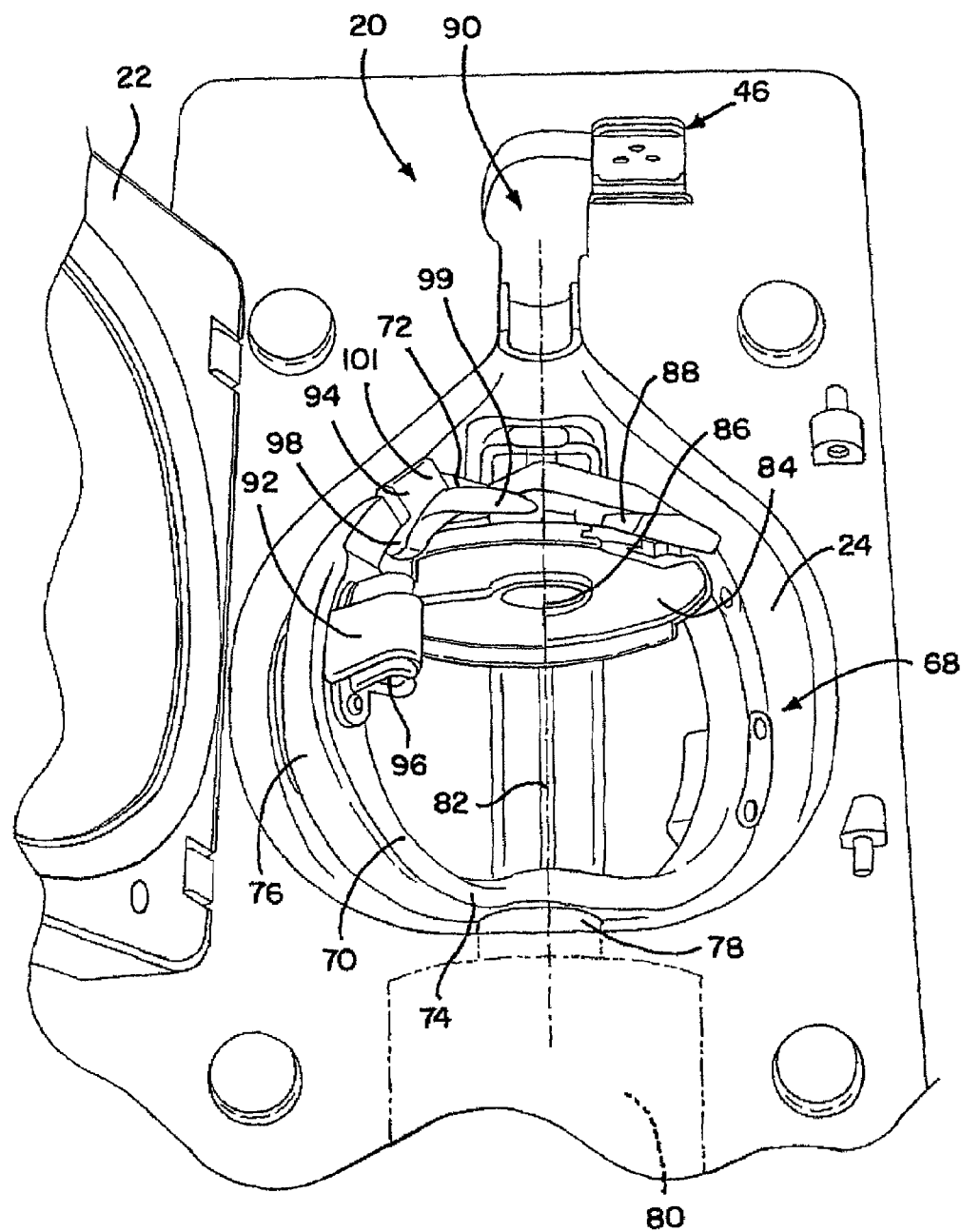
FIG. 9 is a perspective view of the interior of the centrifuge station of the device shown in FIGS. 5 and 6, with the station door opened to receive a blood processing chamber of a type shown in FIG. 7.

As illustrated in FIG. 9, the centrifuge assembly 68 includes a frame or yoke 70 having bottom, top, and side walls 72, 74, 76. The yoke 70 spins on a bearing element 78 (FIG. 9) attached to the bottom wall 72. An electric drive motor 80 is coupled to the bottom wall 72 of the yoke 70, to rotate the yoke 70 about an axis 82. In the illustrated embodiment, the axis 82 is essentially horizontal (see FIG. 3), although other angular orientations can be used. The motor 80 is capable of rotating the yoke 70 in either clockwise or counterclockwise directions, depending upon commands issued by the controller 16.

A carrier or rotor plate 84 spins within the yoke 70 about its own bearing element 86, which is attached to the top wall 74 of the yoke 70. The rotor plate 84 spins about an axis that is generally aligned with the axis of rotation 82 of the yoke 70.

Figure 10:
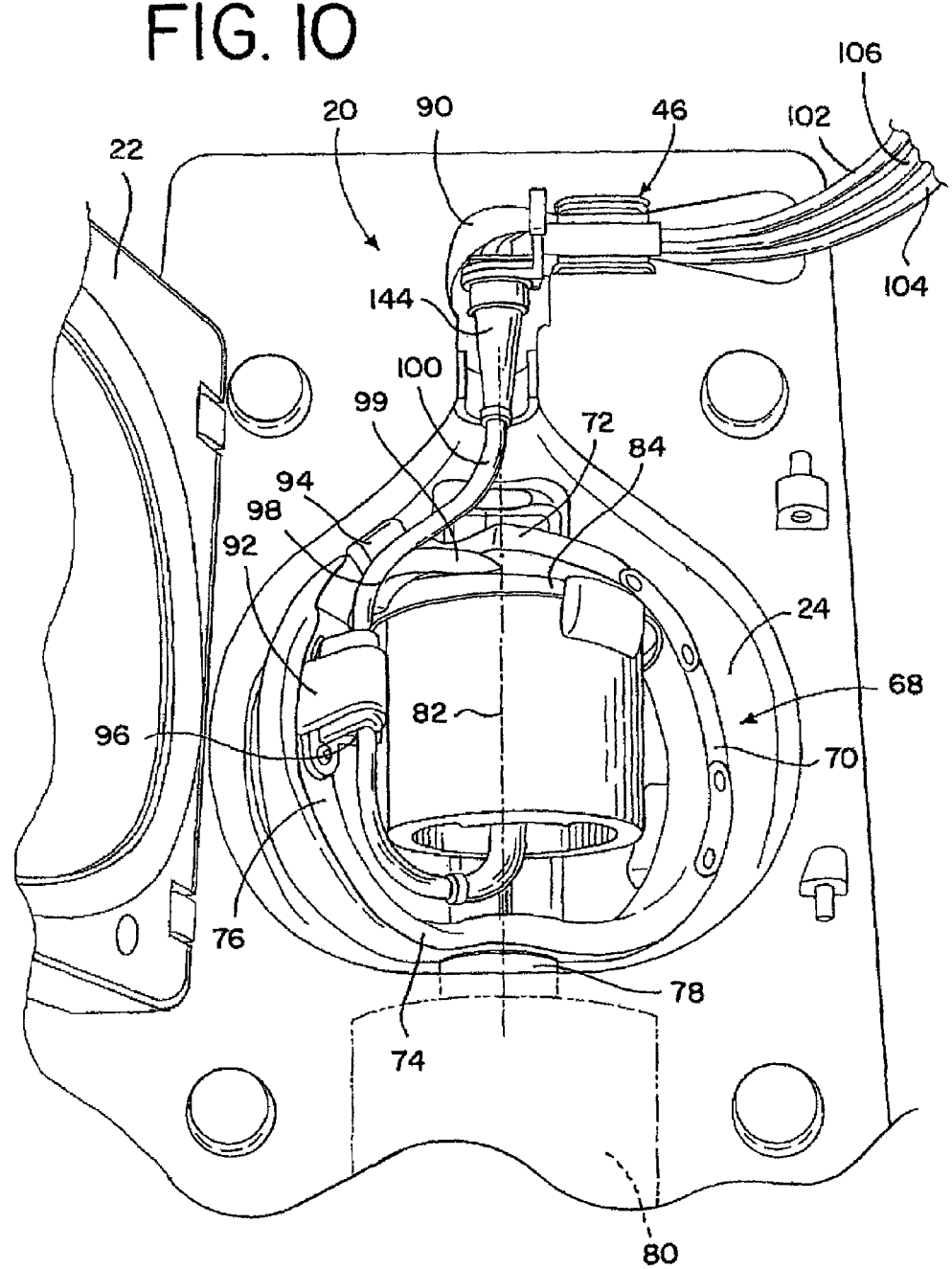
FIG. 10 is a perspective view of the interior of the centrifuge station shown in FIG. 9 after a blood processing chamber of a type shown in FIG. 7 has been loaded for use.

As FIG. 7 shows, the top of the processing chamber 18 includes an annular lip 220, to which the lid component 202 is secured. As FIG. 10 show, the rotor plate 84 includes a latching assembly 88 that removably grips the lip 220, the secure the processing chamber 18 on the rotor plate 84 for rotation. Details of the latching assembly 88 can be found in one or more of the above-identified patents or patent applications which have been incorporated herein by reference.

As FIG. 10 shows, a sheath 144 on the near end of the umbilicus 100 fits into a preformed, recessed pocket 90 in the centrifuge station 20. The pocket 90 holds the near end of the umbilicus 100 in a non-rotating stationary position aligned with the mutually aligned rotational axes 82 of the yoke 70 and rotor plate 84. The tubes 102, 104, and 106 are placed and removed as a group in association with the sensing station 46, which is also located within the pocket 90, as FIG. 10 shows.

Umbilicus drive or support members 92 and 94 and channels 96 and 98 (see FIGS. 9 and 10) receive portions of the umbilicus 100. The relative rotation of the yoke 70 at a one omega rotational speed and the rotor plate 84 at a two omega rotational speed, keeps the umbilicus 100 untwisted, avoiding the need for rotating seals. Further details of this arrangement are disclosed in Brown et al. U.S. Pat. No. 4,120,449, which is incorporated herein by reference and in one or more of the above-identified patents or patent applications which have been incorporated by reference herein.

D. Interface Control by Optical Sensing

Figure 11:
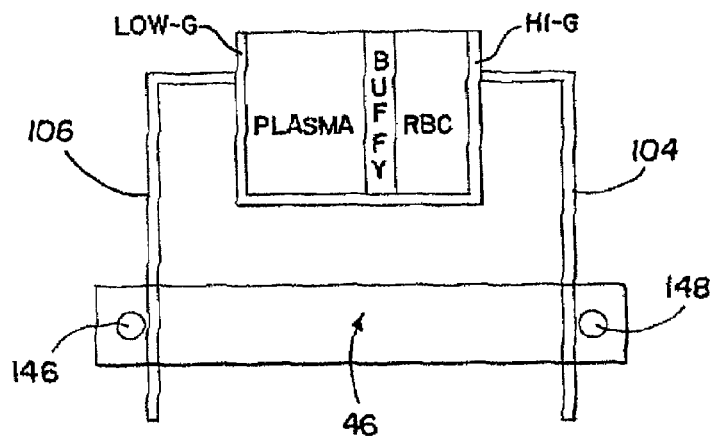
FIG. 11 is a diagrammatic view of the interior of the blood processing chamber of a type shown in FIG. 7, showing the separation of whole blood into a red blood cell layer, a plasma layer, and an intermediate buffy coat layer, with the position of the layers shown during normal conditions.

In any of the above-described blood processing procedures, the centrifugal forces present within the processing chamber 18 separate whole blood into a region of packed red blood cells and a region of plasma (as diagrammatically shown in FIG. 11). The centrifugal forces cause the region of packed red blood cells to congregate along the outside of radially outer or high-G wall of the chamber, while the region of plasma is transported to the radially inner or low-G wall of the chamber.

An intermediate region forms an interface between the red blood cell region and the plasma region. Intermediate density cellular blood species like platelets and leukocytes populate the interface, arranged according to density, with the platelets closer to the plasma layer than the leukocytes. The interface is also called the "buffy coat," because of its cloud color, compared to the straw color of the plasma region and the red color of the red blood cell region.

It may be desirable to monitor the location of the buffy coat, either to keep the buffy coat materials out the plasma or out of the red blood cells, depending on the procedure, or to collect the cellular contents of the buffy coat. For that purpose, the system includes the optical sensing station 46, which houses two optical sensing assemblies is, also diagrammatically shown in FIGS. 11, 12 and 13.

The first sensing assembly 146 in the station 46 optically monitors the passage of blood components through the plasma collection tube 106. The second sensing assembly 148 in the station 46 optically monitors the passage of blood components through the red blood cell collection tube 104.

The tubes 104 and 106 are made from plastic (e.g. polyvinylchloride) material that is transparent to the optical energy used for sensing, at least in the region where the tubes 104 and 106 are to be placed into association with the sensing station 46. The fixture 108 holds the tubes 104 and 106 in viewing alignment with is respective sensing assembly 148 and 146. The fixture 108 also holds the tube 102, which conveys whole blood into the centrifuge station 20, even though no associated sensor is provided. The fixture 108 serves to gather and hold all tubes 102, 104, and 106 that are coupled to the umbilicus 100 in a compact and easily handled bundle.

The first sensing assembly 146 is capable of detecting the presence of optically targeted cellular species or components in the plasma collection tube 106. The components that are optically targeted for detection vary depending upon the procedure.

Figure 12:
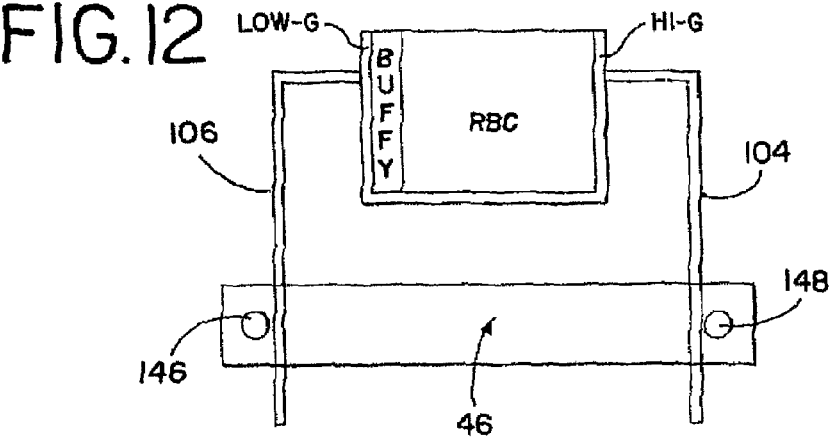
FIG. 12 is a diagrammatic view of the interior of the blood processing chamber of a type shown in FIG. 7, with the buffy coat layer having moved very close to the low-G wall, creating an over spill condition that sweeps buffy coat components into the plasma being collected.

The presence of platelets in the plasma, as detected by the first sensing assembly 146, indicates that the interface is close enough to the low-G wall of the processing chamber to allow all or some of these components to be swept into the plasma collection line (see FIG. 12). This condition will also be called an "over spill."

The second sensing assembly 148 is capable of detecting the hematocrit of the red blood cells in the red blood cell collection tube 104. The decrease of red blood hematocrit below a set minimum level during processing indicates that the interface is close enough to the high-G wall of the processing chamber to allow all or some of the components in the interface and perhaps plasma on the other side of the interface to enter the red blood cell collection tube 104 (see FIG. 13). This condition will also be called an "under spill."

II. Embodiments of the Blood Processing Chamber

Several embodiments of the chamber are described herein. These chambers may be used with the flow set 12 in association with the device 14 and controller 16 to conduct various collection procedures.

A. First Embodiment of the Blood Processing Chamber

Figure 8:
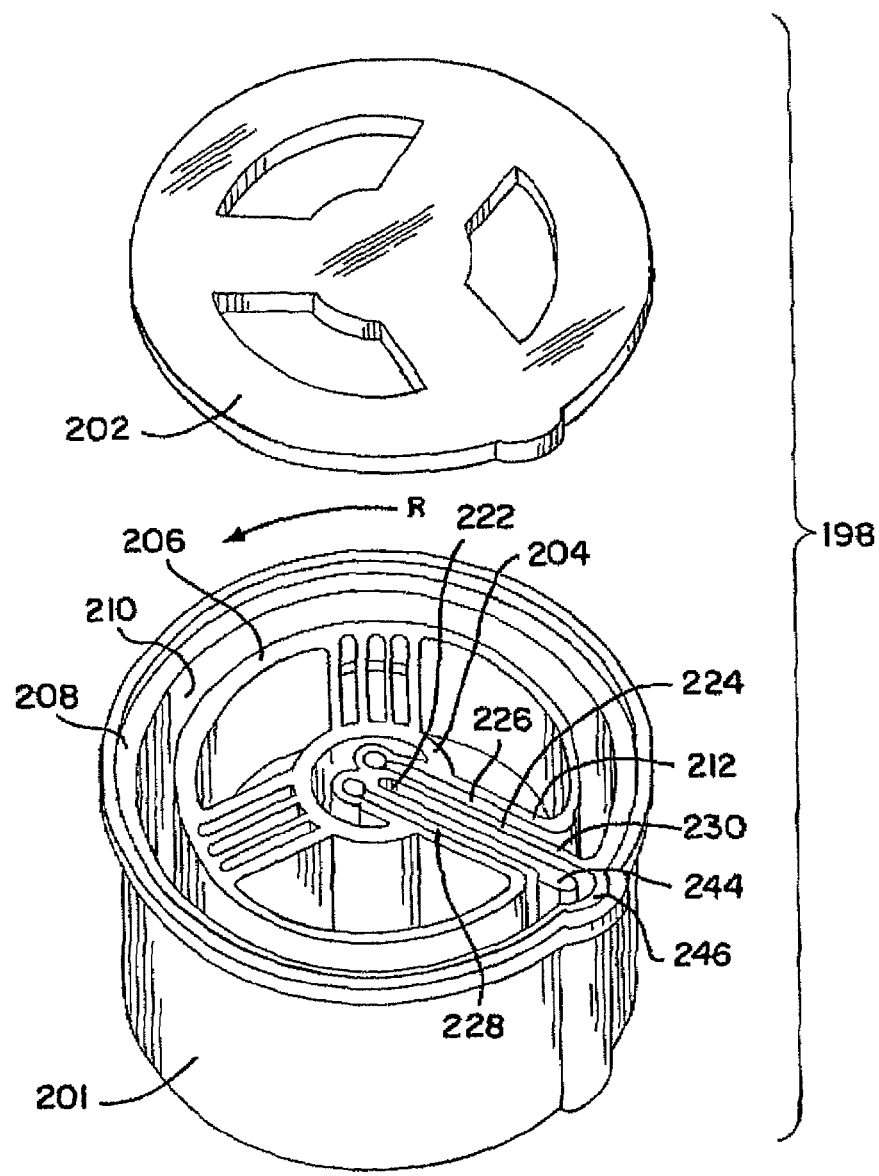
FIG. 8 is a perspective view of the interior of a first embodiment of the blood processing chamber of a type shown in FIG. 7, which may perform a red blood cell separation and collection procedure or other procedures using the device shown in FIGS. 5 and 6.

FIG. 8 shows an embodiment of the centrifugal processing chamber 198, which can be used in association with the system 10 shown in FIG. 1 to perform a double unit red blood cell collection procedure as well as other procedures. The processing chamber 198 is fabricated in two separately molded pieces; namely, the base 201 and the lid 202. The hub 204 is surrounded radially by inside and outside annular walls 206 and 208 that define a circumferential blood separation channel 210. A molded annular wall 214 (see FIG. 7) closes the bottom of the channel 210. The lid 202 is secured to the top of the chamber 200, e.g., by use of a cylindrical sonic welding horn.

The inside annular wall 206 is open between one pair of stiffening walls which form an open interior region 222 in the hub 204. Blood and fluids are introduced from the umbilicus 100 into and out of the separation channel 210 through this region 222. A molded interior wall 224 formed inside the region 222 extends entirely across the channel 210, joining the outside annular wall 208. The wall 224 forms a terminus in the separation channel 210, which interrupts flow circumferentially along the channel 210 during separation.

Additional molded interior walls divide the region 222 into three passages 226, 228, and 230. The passages 226, 228, and 230 extend from the hub 204 and communicate with the channel 210 on opposite sides of the terminus wall 224. Blood and other fluids are directed from the hub 204 into and out of the channel 210 through these passages 226, 228, and 230.

As the processing chamber 198 shown in FIG. 8 is rotated (arrow R in FIG. 8), the umbilicus 100 conveys whole blood into the channel 210 through passage 226. The whole blood flows in the channel 210 in the same direction as rotation (which is counterclockwise in FIG. 8). Alternatively, the chamber 198 can be rotated in a direction opposite to the circumferential flow of the whole blood, i.e., clockwise, although a whole blood flow in the same direction as rotation is believed to be desirable for blood separation efficiencies.

The whole blood separates as a result of centrifugal forces in the manner shown in FIG. 11. Red blood cells are driven toward the radially outer high-G wall 208, while lighter plasma constituent is displace toward the radially under low-G wall 206.

As FIG. 8 shows, a dam 244 projects into the channel 210 toward the high-G wall 208. The dam or barrier 244 prevents passage of plasma, while allowing passage of red blood cells into a channel 246 recessed in the high-G wall 208. The channel 246 directs the red blood cells into the umbilicus 100 through the radial passage 230. The plasma constituent is conveyed from the channel 210 through the radial passage 228 into umbilicus 100.

Because the red blood cell exit channel 246 extends outside the high-g wall 208, being spaced further from the rotational axis than the high-g wall, the red blood cell exit channel 246 allows the positioning of the interface between the red blood cells and the buffy coat very close to the high-g wall 208 during blood processing, without spilling the buffy coat into the red blood cell collection passage 230 (creating an spill under condition). The recessed exit channel 246 thereby permits red blood cells yields to be maximized (in a red blood cell collection procedure) or an essentially platelet-free plasma to be collected (in a plasma collection procedure).

B. Second Embodiment of the Blood Processing Chamber

Figure 14:
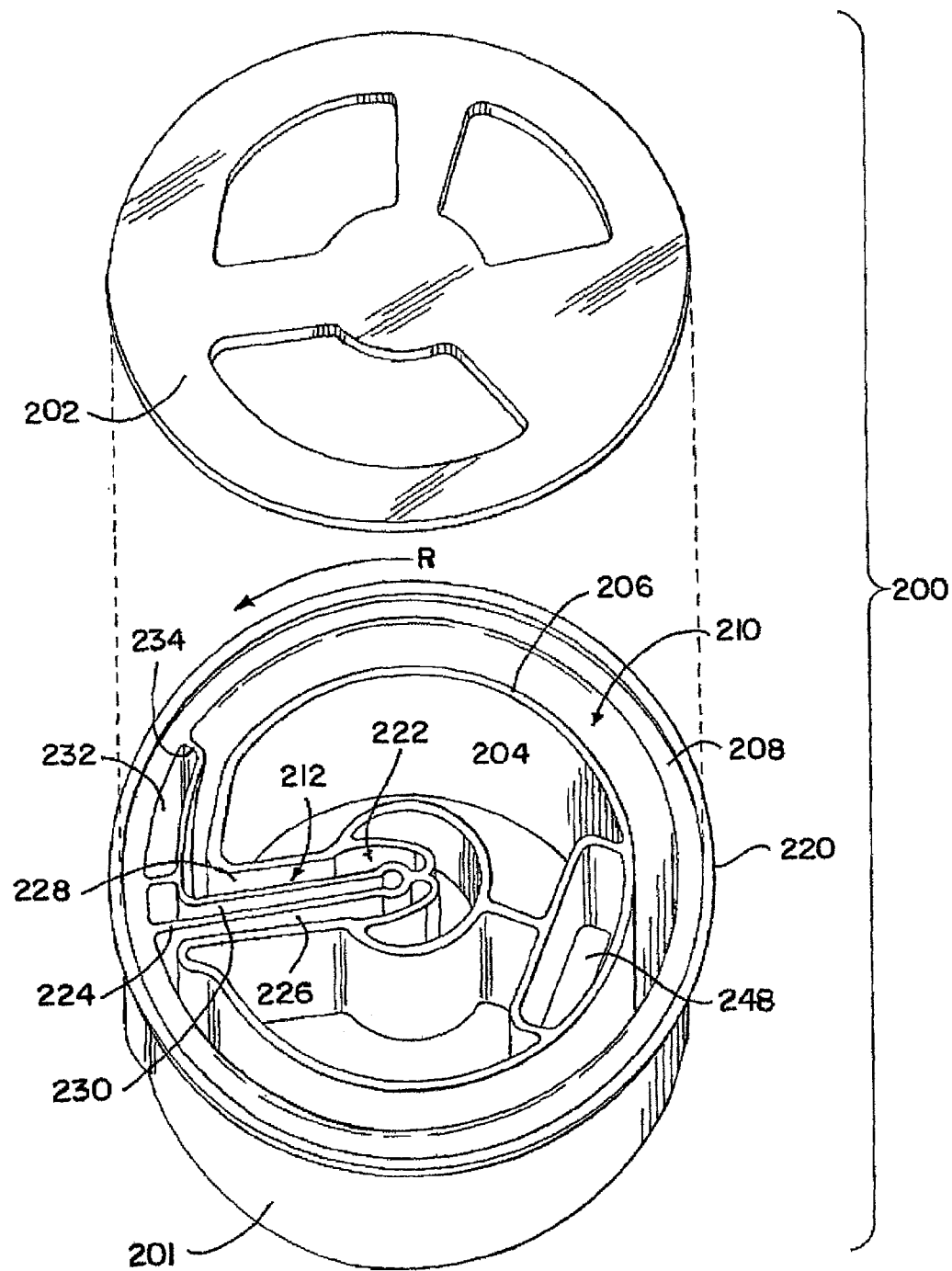
FIG. 14 is a top perspective view of the interior of a second embodiment of the blood processing chamber of the type shown in FIG. 7, the interior of the chamber which may perform a plasma separation and collection procedure or other procedures using the device shown in FIGS. 5 and 6.

FIG. 14 shows an embodiment of the centrifugal processing chamber 200, which can be used in association with the system 10 shown FIG. 1 such as to perform a plasma collection procedure, yielding plasma that is free or essentially free of platelets, red blood cells, and leukocytes. The chamber 200 shown in FIG. 14 can also be used to perform a combined plasma/red blood cell collection procedure, which collects plasma and concentrated red cells separately, as well as other procedures such as platelet collection, which collects a concentrated platelet and plasma mixture.

As previously described with respect to embodiment of a chamber shown in FIG. 8 (with like parts being assigned like reference numerals), the processing chamber 200 is desirably fabricated as separately molded base component 201 and a lid component 202, although other configurations may be employed for this and the other processing chamber embodiments as discussed above in the summary of the invention, without departing from the broader aspects of the present invention. The molded hub 204 is surrounded radially by inside and outside side wall portions 206 and 208 that define a generally circumferential blood separation channel 210. A molded wall 214 (see FIG. 15) forms an end wall portion of the channel 210. The lid component 202 forms another end wall portion of the channel 210 and may also be comprised of an insert 242. While both opposed end wall portions are shown to be generally flat (i.e., normal to the rotational axis) and the side wall portions 206 and 208 are shown as generally cylindrical, it should be appreciated that the boundaries can be tapered, rounded, V-shape, and the like. When assembled, the lid component 202 is secured to the top of the chamber 200, e.g., by use of a cylindrical sonic welding horn.

In the chamber 200 shown in FIG. 14, the inner side wall portion 206 is open between one pair of stiffening walls. The opposing stiffening walls from an open interior region 222 in the hub 204, which communicates with the channel 210. Blood and fluids are introduced from the umbilicus 100 into and out of the separation channel 210 through this region 222.

In the embodiment shown in FIG. 14, a molded interior wall 224 is formed inside the region 222 that extends entirely across the channel 210, joining the outer side wall portion 208. The wall 224 forms terminus in the separation channel 210, which interrupts flow circumferentially along the channel 210 during separation.

Additional molded interior walls divide the region 222 into three passages 226, 228 and 230. The passages 226, 228 and 230 extend from the hub 204 and communicate with the channel 210 opposite sides of the terminus wall 224. Blood and other fluids are directed from the hub 204 into and out of the channel 210 through these passages 226, 228 and 230.

As the processing chamber 200 is rotated (arrow R in FIG. 14), an umbilicus 100 (not shown) conveys whole blood to the passage 226 which leads to channel 210. The whole blood flows in the channel 210 in the same direction as rotation (which is counterclockwise in FIG. 14). Alternatively, the chamber 200 can be rotated in a direction opposite to the circumferential flow of whole blood, i.e., clockwise, although whole blood flow is the same direction as rotation is believed desirable for optimal blood separation.

The whole blood separates within the chamber 200 as a result of centrifugal forces in the manner showing in FIG. 11. Red blood cells are driven toward the outer side wall portion or high-G wall 208, while lighter plasma constituent is displaced toward the low-G wall 206. The buffy coat layer resides between the inner and outer side wall portions 206 and 208.

Circumferentially spaced adjacent the terminus wall 224 nearly 360-degrees from the whole blood inlet passage 226 are the plasma collection passage 228 and the red blood cell collection passage 230. In an upstream flow direction from these collection passages 228 and 230, a barrier 232 projects into the channel 210 from the high-G wall 208. The barrier 232 forms a constriction in the separation channel 210 along the inner side wall portion or low-G wall 206. In the circumferential flow direction of the blood, the constriction leads to the plasma collection passage 228.

Figure 17:
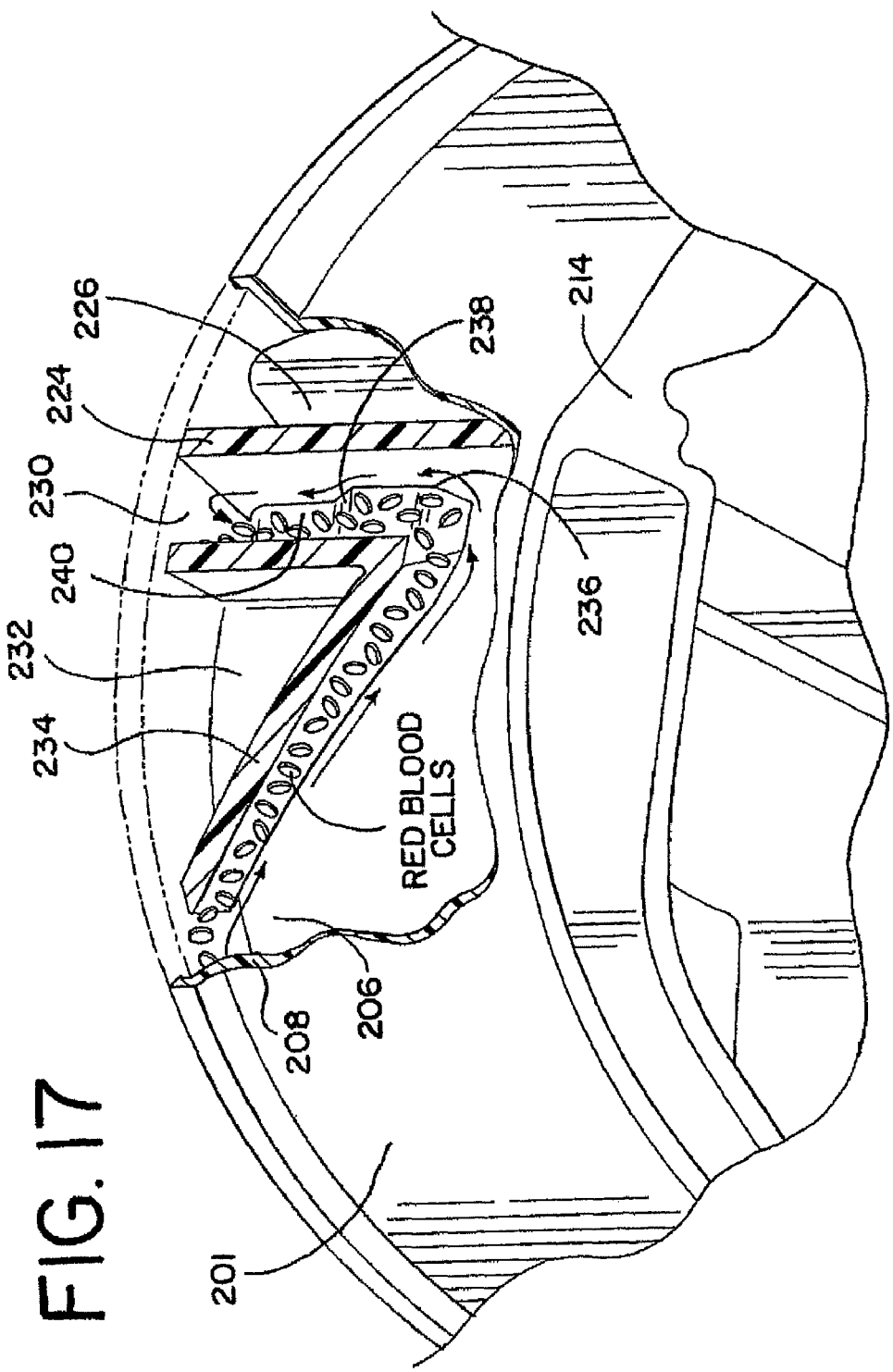
FIG. 17 is an enlarged bottom perspective view of the region shown in FIG. 16, showing the path that red blood cells take as they are directed from the separation zone by the barrier.

As FIGS. 16 and 17 show, a leading edge 234 of the barrier 232 is tapered toward an annular boundary of the channel 210 (which, in the illustrated embodiment, is the annular wall 214) in the direction toward the terminus wall 224. The tapered edge 234 of the barrier 232 leads to an opening 236, which faces the annular boundary of the separation channel 210. The opening 236 faces but is spaced axially away from the annular boundary closely adjacent to the high-G wall 208. The opening 236 communicates with the red blood cell collection passage 230.

A ledge 238 extends an axial distance within the opening 236 radially from the low-G wall 206. The ledge 238 constricts the radial dimension of the opening 236 along the radially outer or high-G wall 208. Due to the ledge 238, only red blood cells and other higher density components adjacent to the high-G wall 208 communicate with the opening 236. The ledge 238 keeps plasma, which is not adjacent the high-G wall 208, away from communication with the opening 236. Due to the radial restricted opening 236 along the high-G wall 208, the plasma has nowhere to flow except toward the plasma collection passage 228. The plasma exiting the separation channel 210 is thereby free or essentially free of the higher density materials, which exit the separation channel 210 through the restricted high-G opening 236.

The ledge 238 joins an axial surface 240, which is generally aligned with the low-G wall 206. The axial surface 240 extends axially along the axis of rotation to the red blood cell collection passage 230. By virtue of the barrier 232, the ledge 238, and other interior walls, the red blood cell collection passage 230 is isolated from the plasma collection passage 228 (as FIG. 18 shows).

Figure 18:
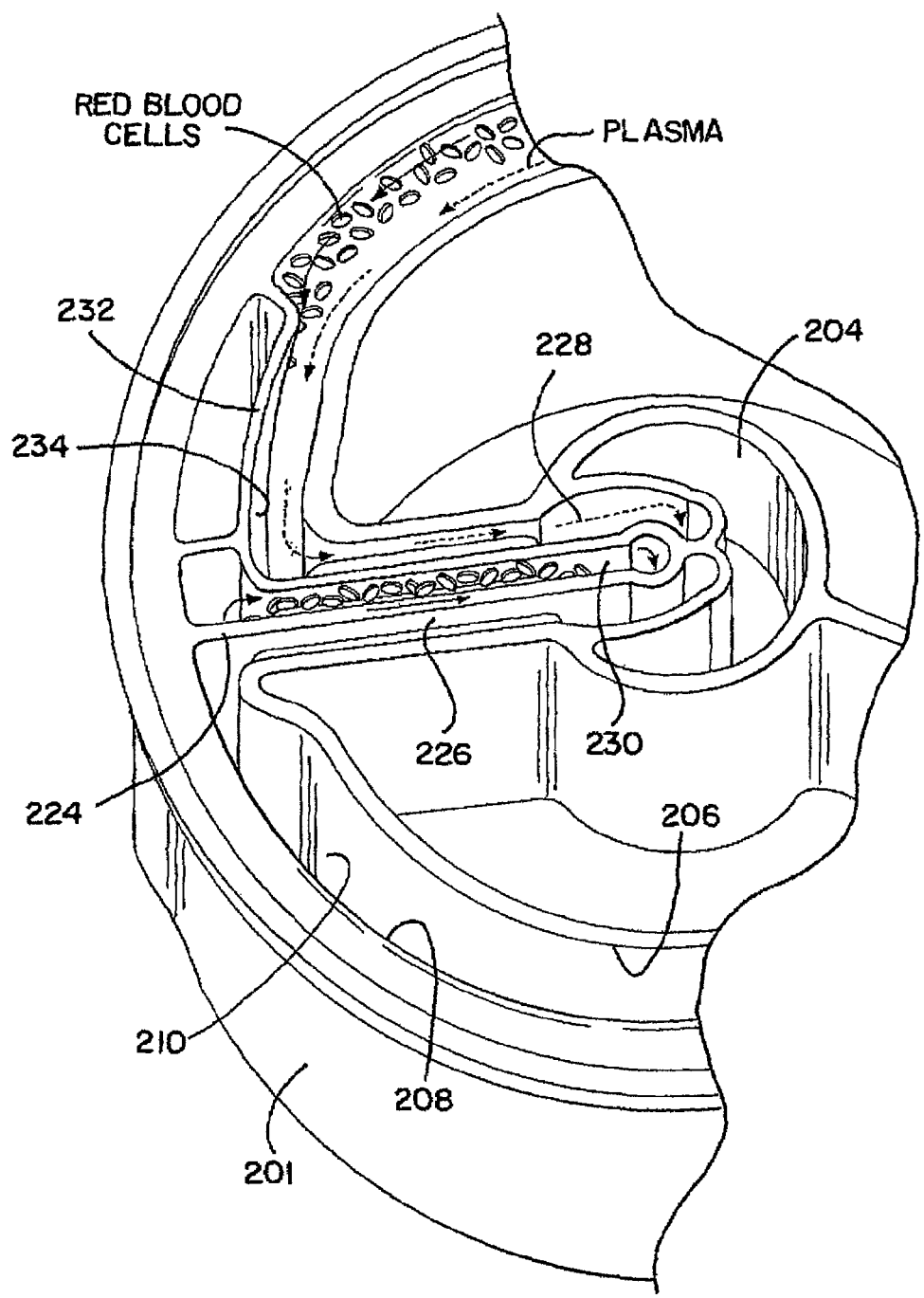
FIG. 18 is an enlarged top perspective view of the region shown in FIG. 16, showing the separate paths that red blood cells and plasma take as they are directed from the separation zone by the barrier.
Figure 19:
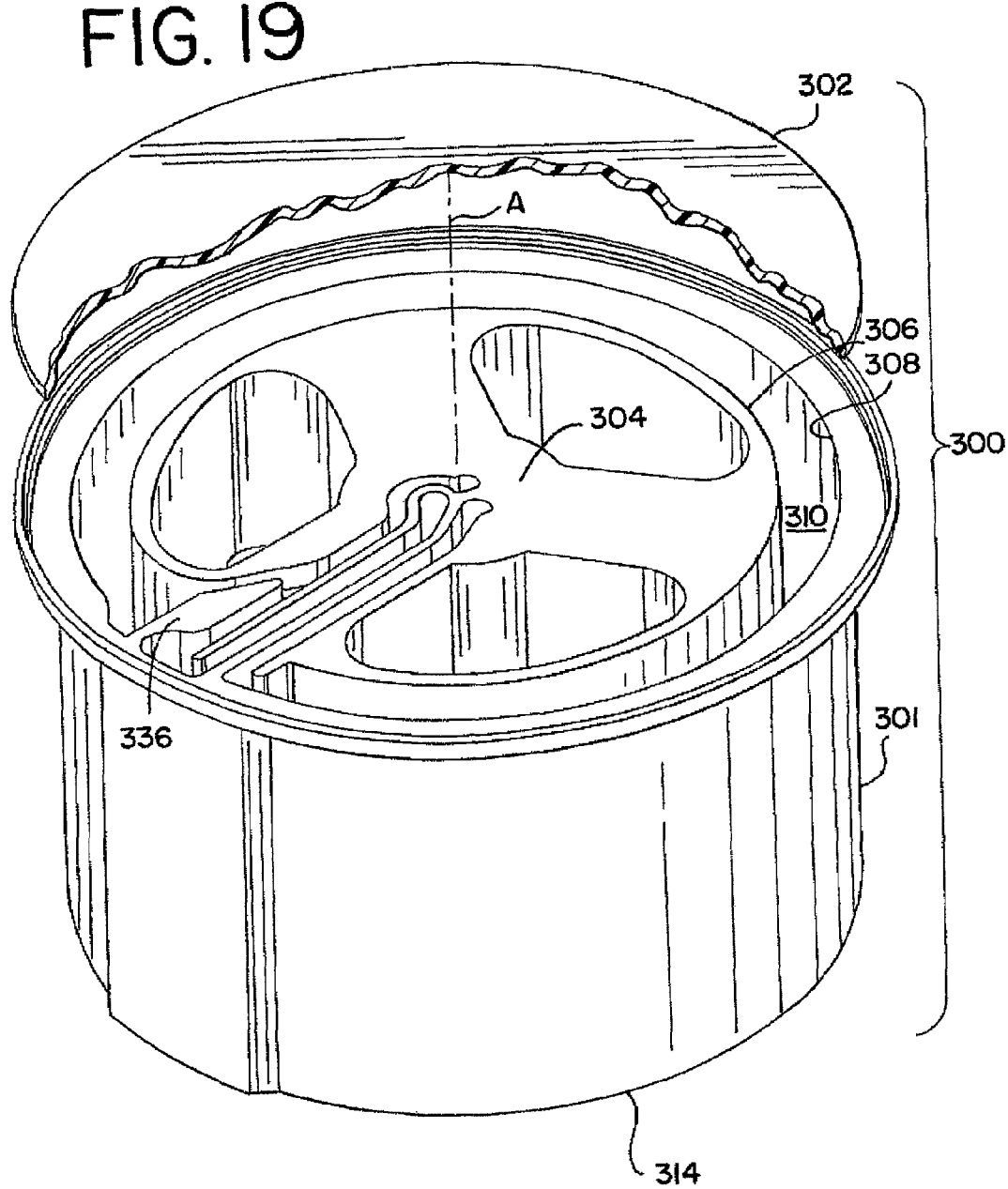
FIG. 19 is a perspective view of the interior of a third embodiment of the chamber of a type shown in FIG. 7, the interior of the chamber which may be used to perform a fluid separation and collection procedure using the device shown in FIGS. 5 and 6, with a partial view of one of the opposed end wall portions being shown spaced from the remaining portion of the chamber.
Figure 21:
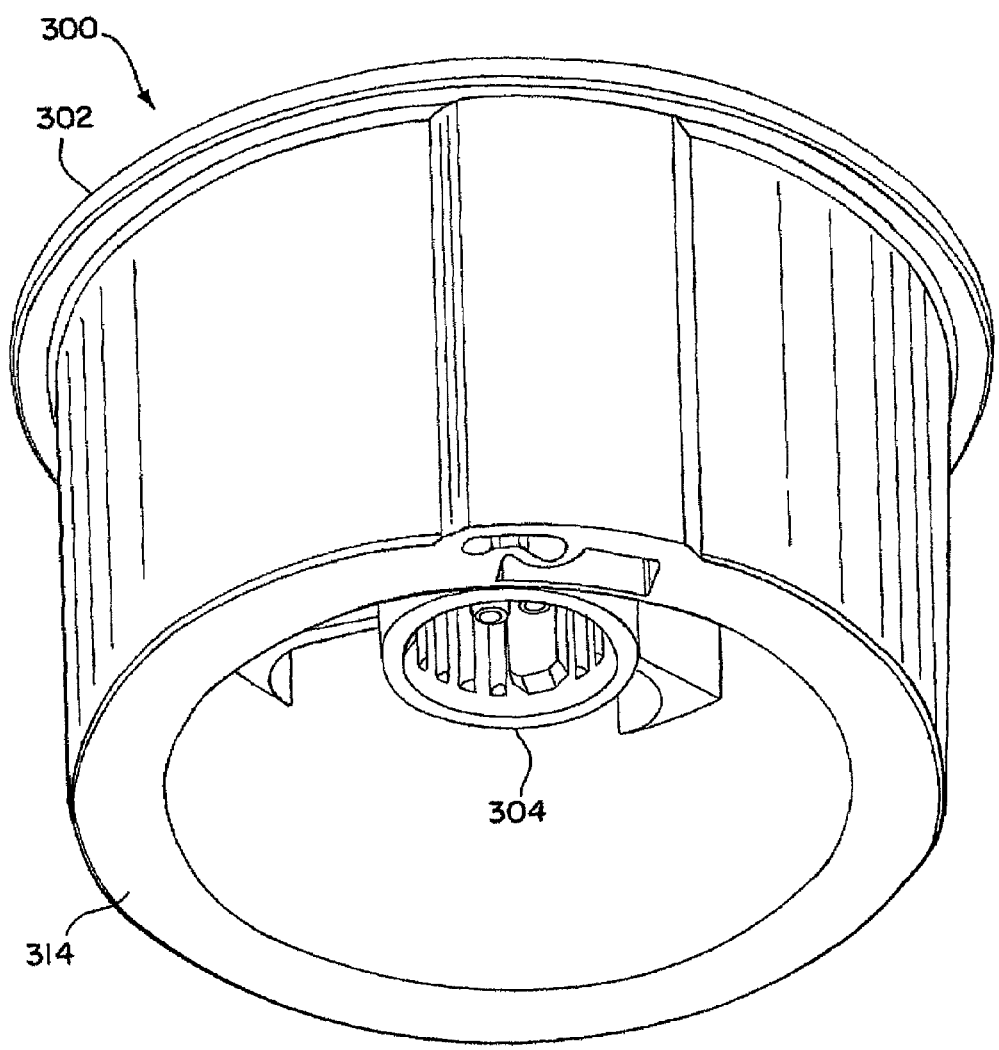
FIG. 21 is a bottom perspective view of the chamber of FIG. 19.

As FIG. 18 also best shows, plasma residing along the low-G wall 206 is circumferentially directed by the barrier 232 and ledge 238 to the plasma collection passage 228 and into the umbilicus 100. The higher density fluid, contain red blood cells and may also contain the buffy coat components (platelets and leukocytes) depending on the procedure employed. Such higher density fluid resides closer to the high-G wall 208 and is directed axially along the tapered edge 234 of the barrier 232 toward an annular boundary and the restricted high-G opening 236. From the high-G opening 236, the red blood cells and buffy coat components comprising the higher density fluid are directed over the radial ledge 238 toward the low-G wall 206, and axially into the red blood cell collection passage 230 and into the umbilicus 100.

C. Third Embodiment of the Blood Processing Chamber

In FIGS. 19-22, the processing chamber is generally indicated at 300. The chamber 300 may be used in association with the system 10 shown in FIG. 1 to perform various collection procedures for various biological fluids, including, but not exclusively, for blood. The chamber 300 may be used to perform a platelet or platelet rich plasma (PRP) collection procedure—which collects a concentrated platelet and plasma mixture—, a combined red blood cell and plasma collection procedure—which collects plasma and concentrated red cells separately—, and a combined red blood cell and platelet collection procedure—which procedure collects concentrated red blood cells and concentrated platelets separately—, as well as other procedures.

The chamber 300 includes a separately molded base component 301 having a hub 304 that is disposed along an axis A of the chamber. The base 301 of the chamber 300 includes radially spaced inner (low-g) and outer (high-g) side wall portions 306 and 308, respectively. The side walls are consistently referred to in this description as the radially inner (or low-g) wall and the radially outer (or high-g) wall. The inner and outer side wall portions 306 and 308 and opposed end wall portions 302 and 314 generally define a circumferential (which is not limited to circular) blood separation channel 310. A first end wall portion 314 forms one axial boundary or bottom to the channel 310 and a second end wall portion or lid 302 (partially shown in FIG. 19) generally forms the other axial boundary or top of the channel 310.

Although the inner and outer wall portions 306 and 308 are shown as substantially circumferential, i.e., as generally vertical walls having a generally uniform radius relative to a common axis A, other orientations, shapes, axes and radii are also possible. Also, while the top and bottom end wall portions are shown to be generally planar, it is also possible that these end wall portions could have other shapes such as curved, arcuate and the like. The shape and orientation of the channel also may depend on whether the channel is formed of flexible, semi-rigid, or rigid structures. It should also be appreciated that the designation of the end wall portions as "top" or "bottom" are not meant to limit these structures. Such terms are meant to be arbitrary and are merely used to distinguish one end wall from the other end wall in the relationship shown in the drawings in order to facilitate understanding of these structures.

Figure 22:
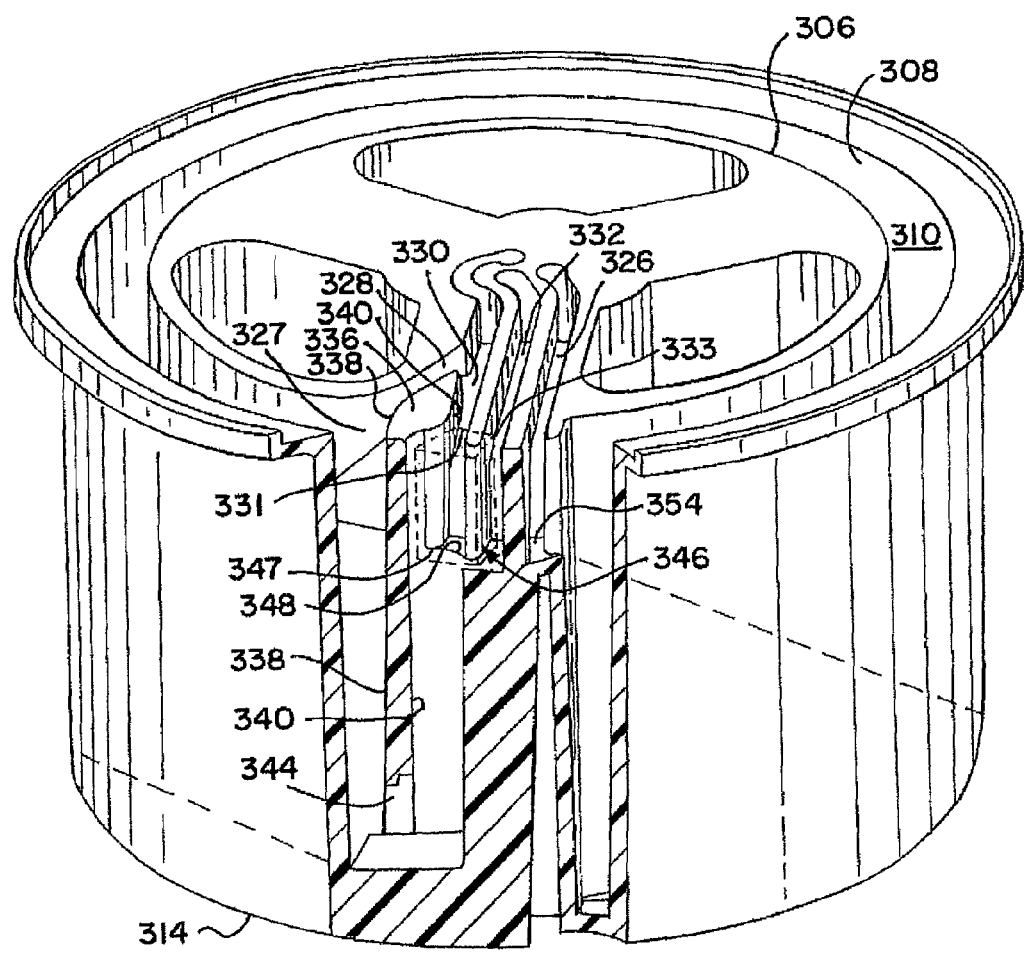
FIG. 22 is a perspective view of the chamber of FIG. 19 with a portion of the chamber shown in section.

As shown in FIGS. 20 and 20A, the upstream end of the channel 310 includes a pair of opposing interior radial walls 322 and 324. The interior radial wall 324 joins the outer side wall portion 308 and generally separates the channel 310 between its upstream and downstream ends. The interior walls 322 and 324 extend radially outward from the hub 304 to define an inlet passageway 326 for a fluid, preferably whole blood, to enter the chamber 300. The inlet passageway 326 is generally defined at or near the top of the chamber 300, as shown in FIG. 22, and preferably is formed in part by a surface of the top end wall portion 302. The inlet 326 includes an opening 325 which is preferably disposed at a radial location which is adjacent the outer or high-g side wall portion 308 and which opening 325 is defined by a surface thereof. A step or edge 323 of the interior radial wall 322 is disposed radially intermediate the inner and outer side wall portions 306 and 308 and also preferably defines a surface of the opening 325 through which fluid is directed into the channel 310.

At the downstream end of the channel 310, first, second and third exit flow paths 328, 330 and 332 may define outlet paths for one or more fluid components from the channel 310. A dam or barrier 336 is also located at the downstream end of the channel 310 and will be described in further detail below.

In FIG. 20A, the first exit flow path 328 is defined between the barrier 328 and an interior radial wall 335 which extends radially outward from the hub 304. Radially inward of the barrier 328, from a junction 352, the first flow path is defined between two interior radial walls 334 and 335. The first exit flow path 328 includes an opening 327 through which fluid enters from the channel 310. Such opening 327 is preferably located upstream of the barrier 336 at a radial location which is approximate to the radial location of the inner side wall portion 306.

When the channel 310 is operating under normal conditions—i.e., not under spill or over spill conditions—fluid in the first flow path 328 preferably flows either radially inward of the junction 352 (and outside of the chamber 300) or, alternatively, travels radial outward at the junction 352 into the second exit flow path 330. By "normal conditions", it is meant that the blood components in the channel 310 are separated into plasma, buffy coat and red blood cells and are preferably disposed in the relative radial locations, as shown in FIG. 11. Normal conditions may also include where the blood components in the channel 310 are separated into platelet rich plasma and red blood cells and the interface between the plasma and red blood cells is disposed radially intermediate the inner (low-g) and outer (high-g) wall, similar to the radial location of the interface shown in FIG. 11.

In FIG. 20A, the second exit flow path 330 is defined generally downstream of the first exit flow path 328 and, between the barrier 336 and the interior radial wall 334. The second exit flow path 330 may allow fluid communication downstream of the barrier 336 between the first and third exit flow paths 328 and 332. The second exit flow path 330 includes a first opening 329 which is preferably adjacent the junction 352 to fluidly communicate with the first exit flow 328 path although other locations are also possible. A second opening 331 of the second exit flow path 330 is preferably radially outward of the first opening 329.

Under normal conditions, the direction of the fluid flow (e.g. plasma flow) in the second exit flow path 330 is generally such that fluid flows radial inward of the junction 352 towards the opening 331. The extent of the radial path traversed by the plasma in the second exit flow path 330 will depend on the radial location of the interface between the plasma and red blood cells. Preferably, plasma flows into the second exit flow path 330 from the first exit flow path 328 to fill the second exit flow path 330 radially inward of the interface but does not flow radially outward of the interface. Under normal conditions, the plasma from the first exit flow path 328 will predominantly flow out of the chamber 300 with some plasma flowing into the second exit flow path 330 to fill the area radially inward of the interface.

Although the preferred flow pattern of the first and second exit flow paths 328 and 330 is discussed above, it is also possible that the fluid within the first and second exit flow paths may follow a different flow pattern. This flow pattern may depend on the position of the interface associated with one or more fluid components and the rate at which one or more fluid components are collected from the channel 310 as well as other factors. By way of example, and not limitation, if the interface between the plasma and red blood cells is moved radially inward to force an over spill condition, then the fluid in the second exit flow path 330 may flow radially outward through the opening 329 at the junction 352.

In FIG. 20A, the third exit flow path 332 is defined between the interior radial walls 334 and 324 and includes an opening 333. Such opening 333 is preferably located downstream of the barrier 336 and downstream of the first and second exit flow paths 328 and 330. Fluid may enter the opening 333 into the third exit flow path 332 for removal from the channel 310.

As shown in FIGS. 20, 20A and 22, the barrier 336 includes an upstream side 338 and a downstream side 340 each of which are generally perpendicular to the outer side wall portion 308. The barrier 336 extends radially across the channel 310 generally between the radial locations which correspond to the inner and outer side wall portion 306 and 308. In FIG. 20A, the barrier preferably is disposed radially inward of the inner (low-g) side wall portion 306 and tapers along an angled wall 342 to the junction 352. The barrier 340 also includes a taper or curve near to or adjacent the outer side wall portion 308. Although the barrier is shown having a shape which tapers near the inner and outer side wall portions 306 and 308, this shape is shown by way of example and not limitation and it is realized that other shapes are also possible.

As shown in FIG. 22, the upstream side 338 of the barrier 336 extends axially from the end wall portion 302 at the top of the channel 310 along a substantial portion of the axial length of the channel 310. At the upstream side 338, the axial location of the barrier 336 terminates at a location which is preferably spaced from the end wall portion 314. At such axial location, a first flow path 344 allows communication between the upstream and downstream sides 338 and 340 of the barrier 336. The first flow path 344 is preferably located at an intermediate axial location between the opposed end wall portions 302 and 314. In FIG. 22, the first flow path 344 is shown closer to the end portion 314 and, more particularly, is shown at an axial location which is approximately located at the bottom half or third of the chamber 300. In FIG. 22, fluid entering through the inlet 326 and traveling to the first flow path 344 must traverse a substantial axial extent of the channel 310. Other intermediate axial locations of the first flow path 344 are also possible, such as intermediate locations along the barrier 336. It is also possible that the first flow path 344 may be located at an axial location which is near to or adjacent the bottom end wall portion 314 of the channel 310.

In FIGS. 20 and 20A, the first flow path 344 is defined along its outer radial surface by one or more of first and second radially outward sections 309 and 311 of the outer side wall portion 308. The first section 309 tapers radially outwardly from a radial location of a more upstream section of the outer side wall portion 308. The first section 309 is generally located upstream of the barrier 336 and joins a second section 311 downstream of the barrier 336. Such second section 311 is also radially outward as compared to the radial location of the outer side wall portion 308 at a more upstream location of the channel 310—i.e. upstream of the section 309. The second section 311 is preferably disposed at the same radial location as the first section 311. An opposed inner radial surface of the first flow path 344 is preferably disposed at a radial location which is approximate to the radial location of the more upstream section of the outer side wall portion 308.

In FIGS. 20 and 20A, a collection region, generally defined at 346, is disposed downstream of the barrier 336 (shown in broken lines). A top surface of the collection region 346 is defined by the end wall portion 302 at the top of the channel 310. The collection region 346 also includes an intermediate end wall portion 348 (FIG. 22) which defines at least a portion of the bottom surface of the collection region 346. The intermediate end wall portion 348 is axially spaced from the end wall portions 302 and 314 at the top and bottom of the channel 310. Although the intermediate end wall portion 348 is shown generally parallel to the end wall portion 314 of the channel 310, other orientations are also possible.

In FIG. 20A, the collection region 346 is also defined, in part, by the downstream side 340 of the barrier 336 and the interior wall 324 of the channel 310. Also, in FIG. 20A, the collection region 346 is generally disposed between the radial locations corresponding to the inner and outer side wall portions 306 and 308 and preferably is defined between the radial locations of the inner side wall portion 306 and the section 311 of the outer side wall portion 308.

As best seen in FIG. 22, the collection region 346 includes an axially directed opening 347 formed in the intermediate end wall portion 348. Fluid travels axially upwards from the first flow path 344 along the downstream side 340 of the barrier 336 to enter the bottom of the collection region 346 through the opening 347. As previously described, the openings 331 and 333 (as best seen in FIG. 20A) may also allow fluid communication of one or more fluid components into or out of the collection region 346. In FIG. 20A, the collection region 346 includes a radially outward edge 350 of the interior radial wall 334 which is positioned between the openings 331 and 333 to the second and third exit flow paths 330 and 332. Such edge 350 is disposed at an intermediate radial location between the inner side wall portions 306 and the radially outward section 311 of the outer (high-g) wall portion 308. The radial location of the edge 350 is preferably positioned closer to the radial location of the section 311. Such edge 350 is preferably positioned so that during normal conditions the higher density fluid such as red blood cells may exit the third exit flow path 332 and so that the lower density fluid does not exit therethrough.

During use, a fluid, such as whole blood, enters the inlet 326 and flows into the channel 310. As the fluid first enters the channel 310, the fluid is generally located at the top of the channel 310. The axial extent of fluid flow at the opening 325 of the inlet passageway 326 may be initially confined at its lower axial extent at the inlet by a bottom floor 354 (as seen in FIG. 22). The axial location of the floor 354 may be disposed at an axial location which is approximate to that of the intermediate end wall portion 348 of the collection region 346 although other axial locations are also possible. After the fluid enters the channel 310, the channel is preferably no longer constrained at its lower axial extent, although it is still constrained at its upper axial extent by the opposed end wall portion 302.

In the channel 310, the fluid may essentially follow a spiral pattern (shown in broken lines in FIG. 22) as it travels downstream so that the fluid generally increases in its axial extent although other patterns are also possible. Upstream of the barrier 336, the axial extent of the fluid is preferably disposed from the top end wall portion 302 at the top of the channel 310 to at least the approximate axial location of the first flow path 344 or lower. By utilizing as much volume within the channel, it is believed that more efficient separation of the fluid components is obtained.

As the blood flows downstream, centrifugal force allows the components of the blood to separate radially according to density within the channel 310. Further details of this separation are set forth in Brown, "The Physics of Continuous Flow Centrifugal Sell Separation," Artificial Organ, 13(1):4-20 (1989).

FIG. 11 shows one example of the relative radial locations of the blood components upstream of the barrier 336 during normal conditions of the channel 310. Plasma is primarily disposed towards the inner or low-g side wall portion 306, and the red blood cells are primarily disposed towards the outer or high-g side wall portion 308. Platelets and leukocytes, also known as the "buffy coat", are primarily disposed at an interface between the plasma and red blood cells and are located at intermediate radial location. For a platelet collection procedure, further processing steps are preferably performed, as described in further detail below, to suspend at least a portion of the platelets in the plasma so as to form platelet rich plasma on one side of the interface between platelet rich plasma and red blood cells.

Upstream of the barrier 336, at least one fluid component may be collected through the first exit flow path 328. Such component may include platelet poor plasma PPP or platelet rich plasma PRP. Such component also may flow into the second exit flow path 330 at the junction 352. Another fluid component, preferably, red blood cells, may flow into the first flow path 344 for removal through the third exit flow path 332. If the platelets are primarily located in the buffy coat, at least a substantial portion of the buffy coat is sequestered at the upstream side 338 of the barrier 336. In this regard, the barrier 336 may allow accumulation of platelets upstream of the barrier 336 at a certain point during the procedure, for example, where platelet poor plasma PPP is being removed from the channel 310. Such procedures will be discussed in further detail below. Thus, the portion of the interface between the plasma and red blood cells downstream of the barrier 336 preferably contains substantially less or virtually no platelets as compared to the interface located between these components upstream of the barrier 336.

Downstream of the barrier 336, the interface is allowed to form between the red blood cells and plasma which may also be either platelet rich or platelet poor plasma. Under normal conditions, the interface between the plasma and red blood cells is located at an intermediate radial location—i.e. between the inner and outer wall portions 306 and 308—. Such interface is preferably located radially inward of the first flow path 344 so that primarily red blood cells flow through the first flow path 344 during normal conditions. More preferably, the interface between the red blood cells and plasma is disposed at a radial location which is approximate to the edge 350. Such radial location allows the red blood cells to be collected from one side of the interface into the third exit flow path 332 but allows substantially little or no flow of plasma from the other side of the interface into the third exit flow path 332. Plasma and red blood cells primarily flow through the first and third exit flow paths 328 and 332, respectively. The second flow path 330 preferably contains plasma or platelet rich plasma radially inward of the interface and red blood cells radially outward of the interface. Some flow of plasma or red blood cells may occur in the second exit flow path 330, depending on the radial location of the interface, but such flow preferably does not change such location of the interface.

Other flow patterns are possible and may depend on other radial positions of the interface. For example, during an over spill condition, —i.e., where red blood cells flow out of the channel through the first exit flow path 328 with the plasma or platelets—, the interface moves radially inward and the second exit flow path 330 may allow red blood cells to flow from the collection region 346 out of the channel 310. During an under spill condition, —i.e., where plasma or platelets flow out of the channel through the third exit flow path 332 with red blood cells—the interface moves radially outward and the second exit flow path 330 may allow some plasma or platelets from the first exit flow path 328 to flow into the third exit flow path 332.

D. Fourth Embodiment of the Blood Processing Chamber

FIGS. 23 and 24 illustrate a chamber generally indicated at 360 which is identical to the chamber 300 of FIGS. 19-22 (with all identical parts being identified with identical numbers and shall not be described further) except for certain modifications which will be described further below. As compared to the embodiment of FIGS. 19-22, FIGS. 23-24 show that the opening 325 of the inlet 326 is disposed at a radial location which is approximate to the outer side wall portion 308. The blood thus is allowed to enter the channel 310 at a location which is tangential to the outer (high-g) wall portion 308. Such location may aid in the separation of the blood component and/or may avoid back flow of blood components if the flow rate through the inlet 326 is slowed or stopped.

The inlet 326 is defined by a radially outward portion 309C of the outer side wall portion 308. The edge 323 of the interior wall 322 is radially spaced from the portion 309C and is disposed at a radial location which is approximate to the radial location of the outer side wall portion 308 at a more downstream section of the wall portion 308. Fluid flowing through the inlet 326 follows a path along the interior wall 322 to a location which is radially outward of the edge 323 and then enters the channel 310 through the opening 325.

E. Fifth Embodiment of the Blood Processing Chamber

Figure 23A:
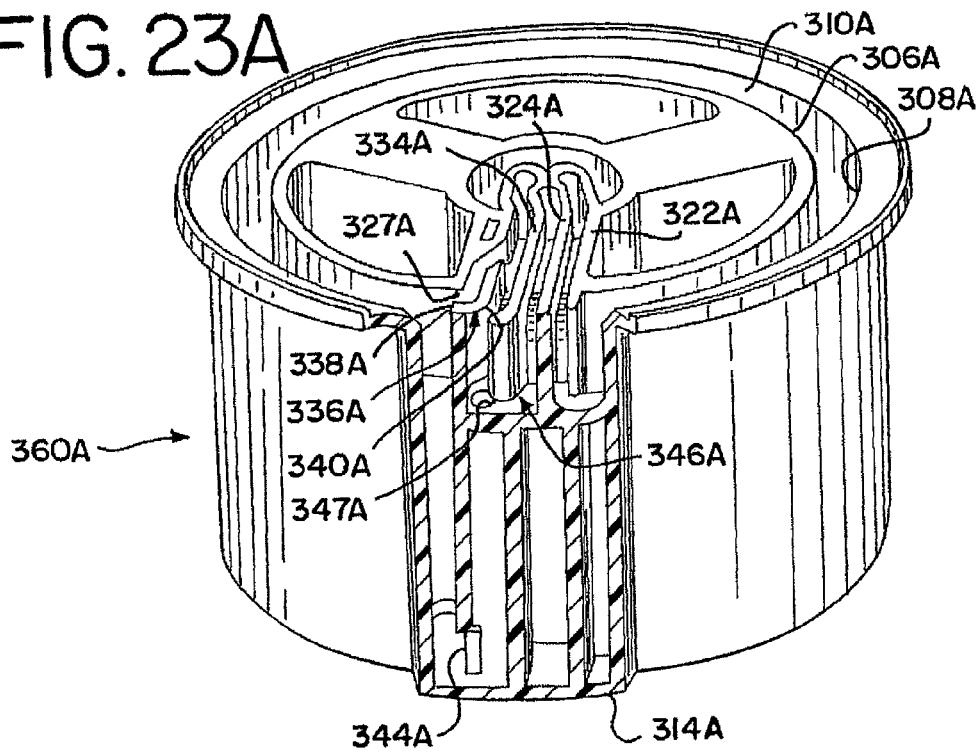
FIG. 23A is a perspective view of a fifth embodiment of the chamber which is similar to the chamber of FIG. 23 except that the chamber of FIG. 23A lacks any exits paths from the channel upstream of the barrier.
Figure 24A:
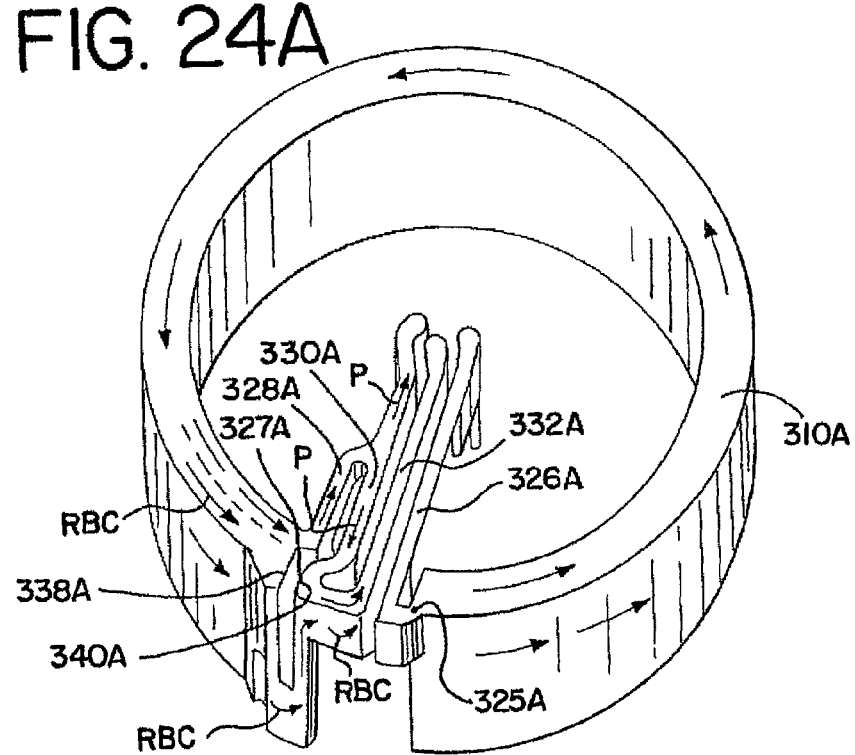
FIG. 24A is a perspective view of the fluid flow of the chamber shown in FIG. 23A, with the chamber removed, so as to show the path of the fluid inside the chamber.

FIGS. 23A and 24A show a chamber 360A, or the fluid flow within such chamber, which chamber is similar to the chamber 360 of FIGS. 23 and 24, and, as such, identical numerals will be used to describe identical parts, followed by the letter 'A' and will not be described further.

As compared to the embodiment of FIGS. 23 and 24, the first flow path 344A of FIGS. 23A and 24A is disposed at an axial location which is adjacent the end wall portion 314A at the bottom of the chamber 360A. The first flow path 344A may be defined by a surface of the end wall portion 314A. In this regard, fluid flowing into the first flow path 344A must increase in its axial extent essentially to the bottom of the channel 310A. At the downstream side of the barrier 336A, the fluid travels from the bottom of the channel 310A in an axial direction towards the top of the channel to enter the collection region 346A through the opening 347A. As shown in FIG. 24A, the fluid occupies a substantial portion of the volume of the channel 310A between the first end wall portion 314A at the bottom of the channel 310A and the second end wall portion (not shown) at the top of the channel.

Also as compared to the embodiment of FIGS. 23 and 24, the channel 310A of FIGS. 23A and 24A lacks an opening to an exit flow path 328A at a location which is upstream of the barrier. In FIGS. 23A and 24A, an opening 327A into the first exit flow path 328A is located in the channel 310A at a location which is either at or slightly downstream of the upstream side 338A of the barrier 336A. As previously described, plasma, either rich or poor in platelets, enters the opening 327A and may flow radially inward of the junction 352 to exit the channel 310A or, alternatively, flow into the second exit flow path 330A. A first flow path 344A allows fluid communication between the upstream and downstream sides 338A and 340A of the barrier 336A but does not form an exit flow path to the outside of the channel 310A. Red blood cells flowing through the first flow path 344A preferably exit the channel 310A through a third exit flow path 332A downstream of the barrier 336A.

F. Sixth Embodiment of the Blood Processing Chamber

Figure 25:
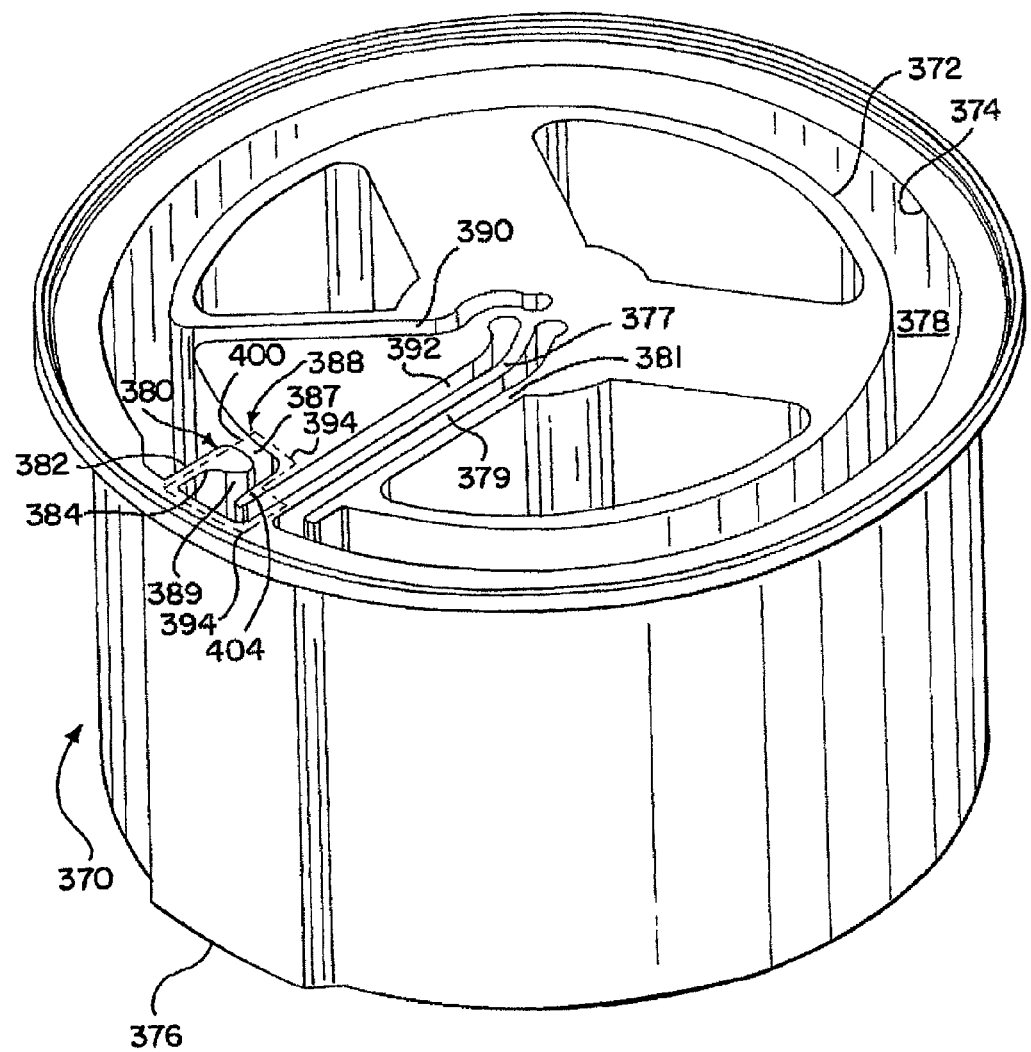
FIG. 25 is a sixth embodiment of the chamber of the type shown in FIG. 7, the interior of the chamber being configured to perform a platelet separation and collection procedure using the device shown in FIGS. 5 and 6.
Figure 26:
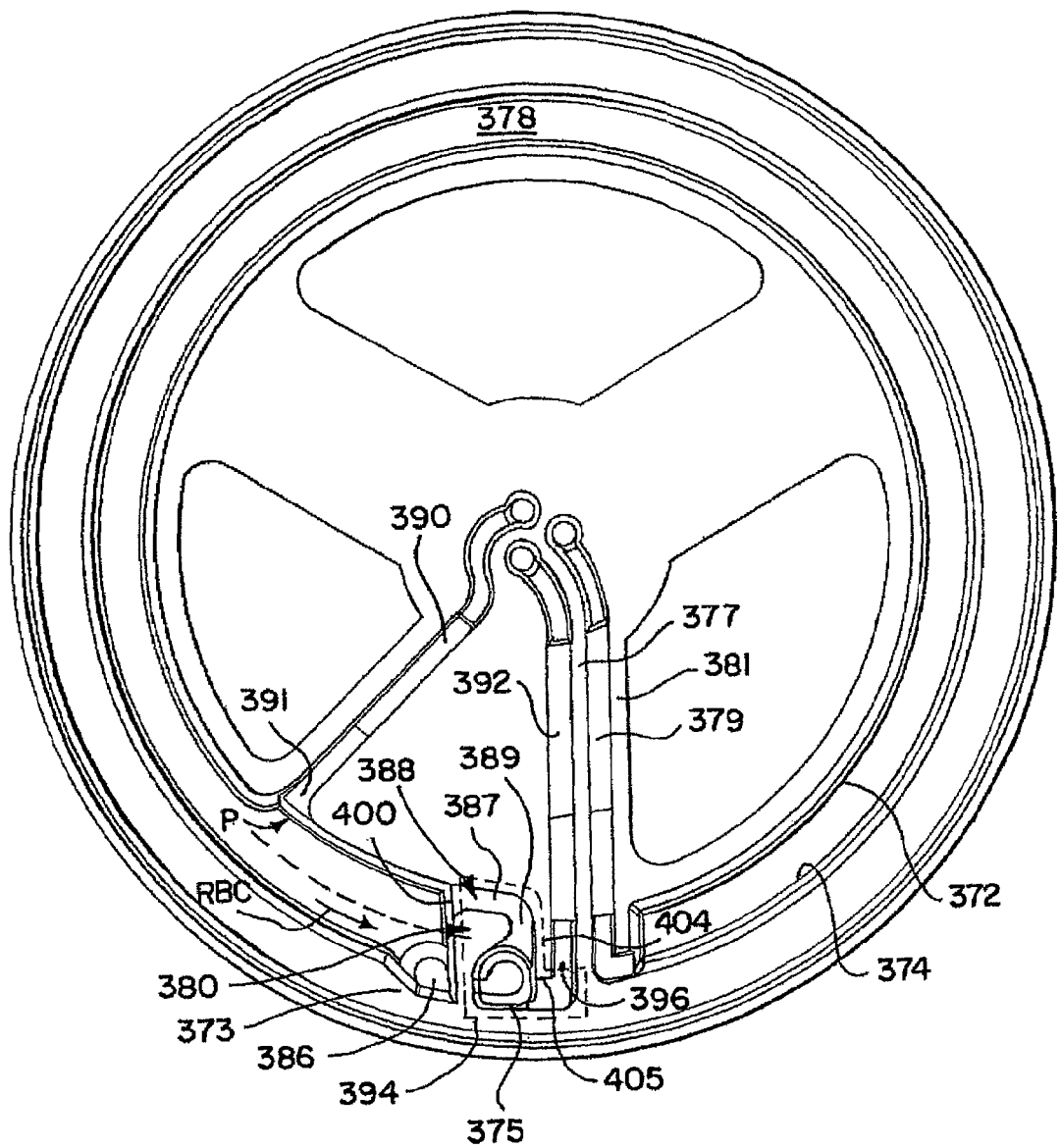
FIG. 26 is a top view of the interior of the chamber shown in FIG. 25.
Figure 27:
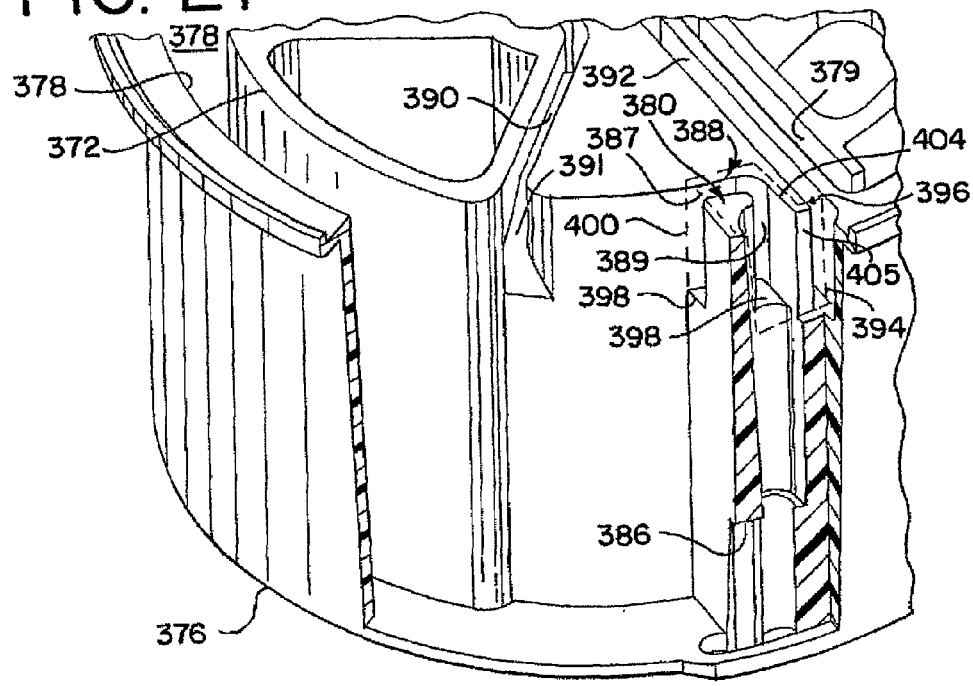
FIG. 27 is a partial perspective view of the chamber of FIG. 25 with portions of the chamber shown in section.

FIGS. 25-27 illustrate a further embodiment of a chamber, which is generally indicated at 370 having radially spaced apart inner (low-g) and outer (high-g) side wall portions 372 and 374, respectively, and a first and second end walls (only a first end wall portion 376 being shown). The wall portions 372, 374 and 376 together define a channel 378.

An inlet 379 is defined between opposing interior radial walls 377 and 381. One of the interior walls 377 joins the outer (high-g) wall portion and separates the upstream and downstream ends of the channel 378. Similar to the embodiment of FIG. 19-22, the interior walls define the inlet passageway 379 of the chamber 370 which allow fluid to enter the upstream end of the channel 378 at a location which is adjacent the outer or high-g side wall portion 374. A dam or barrier 380 is formed at a downstream end of the channel 378 and has upstream and downstream sides 382 and 384 and extends from the outer side wall portion 374 radially inward to a location which is spaced from the inner side wall portion 372. The barrier 380 will be described in further detail below.

In FIGS. 26-27, a first flow path 386 (FIG. 26) communicates between the upstream and the downstream sides 382 and 384 of the barrier 380. In FIG. 27, the first flow path 386 is located at an intermediate axial position spaced above the bottom end wall 376 and spaced below the top end wall (not shown). Similar to the embodiments of FIGS. 18-24, sections 373 and 375 (FIG. 26) of the outer side wall portion 374 just upstream and downstream of the barrier 382 extend radially outward from a more upstream section of the outer side wall portion 374. An outer radial surface of the first flow path 386 is preferably formed in part by one or more of these radially outward sections 373 and 375 of the outer side wall portion 374 (which sections 373 and 375 are shown removed in FIG. 27). An opposed inner radial surface of the first flow path 386 is preferably formed at a radial location which is approximate to that of the outer or high-G wall portion 374.

A second flow path, generally indicated at 388, also communicates between the upstream and downstream sides 382 and 384 of the barrier 380. As shown in FIG. 27, an opening 400 of the second flow path 388 preferably allows fluid to flow into the second flow path from a more upstream location of the channel 378. The second flow path 388 is preferably defined by a surface of the second end wall portion (not shown) which is generally placed over the top of the chamber shown in FIGS. 25-27. An intermediate end wall portion 398 defines the lower axial surface of the second flow path 388 and will be described in further detail below. As shown in FIGS. 26 and 27, the second flow path 388 includes both non-radial and radial portions 387 and 381, respectively. The non-radial portion 387 is preferably defined by the space between the inner side wall portion 372 and a radially inward surface of the barrier 380. The radial portion 389 is defined by the downstream side 384 of the barrier 380 and an interior radial wall extension 404. The interior radial wall extension 404 terminates at an outer edge 405 which is located at an intermediate radial location between the inner and outer side wall portions 372 and 374.

The chamber 370 further includes first and second exit flow paths 390 and 392, respectively, which are defined by opposing surfaces of interior radial walls. The first exit flow path 390 is located upstream of the barrier 380. The second exit flow path 392 is located downstream of the barrier 380. Both first and second exit flow paths 390 and 392 extend radially inward from the channel 378. The first exit flow path 390 extends radially inward from an opening 391 which is preferably located at the inner side wall portion 372. The second exit flow path 392 extends radially inward from an opening 396. Such opening 396 communicates with a collection region 394, which region is located downstream of the barrier 380 and extends to the interior radial wall 377. Preferably, the first exit flow path 390 is disposed at approximately a 45 degree angle from the second exit flow path 392, although other angles and orientations are also possible.

In FIGS. 26 and 27, the collection region 394 is defined at least in part, at its lower boundary by the end wall portion 398 which is spaced above the first end wall portion 376 of the channel 378. The top of the collection region 394 is preferably defined by the end wall portion (not shown) at the top of the channel 378. The collection region 394 is also generally defined between the section 375 of the outer side wall portion 374 and the inner side wall portion 372. Fluid may enter the collection region 394 through the first flow path 386 and may also enter through the second flow path 388, depending on the location of the interface between the plasma and red blood cells. The fluid from the collection region 394 may exit through the outlet 396 into the second exit path 392 for removal from the channel 378.

FIG. 26 shows the relative positions of plasma P and red blood cells RBC during normal conditions where the interface is located radially intermediate the inner (low-g) and outer (high-g) wall portions 372 and 374. Plasma or platelet rich plasma is preferably collected through the opening 391 in first exit flow path 390 upstream of the barrier 380. Further downstream, a portion of the plasma is also permitted to flow into the opening 400 and through at least a portion of the second flow path 388. The extent of such plasma flow into the second flow path 388 will depend on the location of the interface between the plasma and red blood cells. For example, the interface between the plasma and red blood cells is preferably located at or near the edge 405 of the interior radial wall extension 404 during normal conditions. During such conditions, plasma flowing into the second flow path 388 will preferably remain radially inward of the edge 405 until further processing steps are performed to move the interface and allow collection thereof. Red blood cells RBC are permitted to flow through the first flow path 386 into the collection region 394, and exit the channel 378 through the outlet 396 of the second exit flow path 392.

G. Seventh Embodiment of the Blood Processing Chamber

Figure 28:
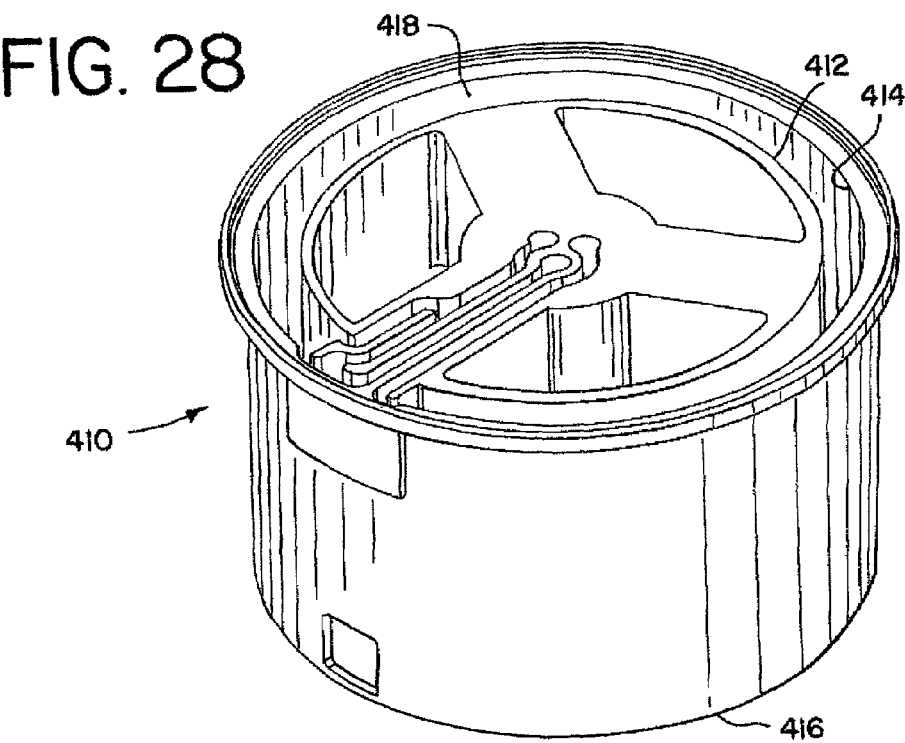
FIG. 28 is a perspective view of the interior of a seventh embodiment of the chamber of the type shown in FIG. 7, the interior of the chamber being configured to perform a fluid separation in a collection procedure using the device shown in FIGS. 5 and 6

FIGS. 28-30 illustrate a further embodiment of the blood processing chamber, generally indicated at 410. Similar to previous embodiments, the chamber 410 has radially spaced apart inner and outer side wall portions 412 and 414, respectively, and an end wall portion 416 at the bottom of the chamber 410 opposite an end wall portion (not shown) at the top of the chamber 410. Together the inner and outer side wall portions 412 and 414 and the end wall portions define a channel 418.

In FIG. 29, radially directed interior walls 420 and 422 define an inlet 424 which communicates with the channel 418. The interior wall 422 extends fully to the outer side wall portion 414 to separate the upstream and downstream ends of the channel 418. Similar to the embodiments of FIGS. 23-24, an opening 425 of the inlet passageway 424 is disposed at a radial location which is tangential to the radial location of the outer side wall portion 414. Preferably, the interior wall 420 terminates at an edge 443 which is radially spaced from a radially outward wall section 413 of the outer side wall portion 414 so as to direct fluid into the channel 418. Such edge 443 may be located at a radial location approximate to that of the outer (or high-G) wall portion 414.

In FIG. 29, a barrier 426 is generally located at the downstream end of the channel 418 and includes upstream and downstream sides 428 and 430, respectively, and radially inner and outer edges 432 and 434, respectively. In FIGS. 29 and 30, the barrier 426 joins the inner and outer side wall portions 412 and 414 along a substantial axial extent of the channel. As shown in FIG. 30, the barrier 426 preferably joins the inner and outer side wall portions 412 and 414 along an axial extent from an intermediate end wall portion 460 to the end wall portion 416 at the bottom of the channel 418.

Above the intermediate end wall portion 460, the inner and outer radial edges of the barrier 426 are not joined so as to allow flow around the barrier 426. As shown in FIG. 30, the radially inner edge 432 is spaced from the inner side wall portion 412 along an axial extent from the top of the channel 418 to the intermediate end wall portion 460. The inner edge 432, in part, defines an exit opening 448 from the channel 418 through a first exit flow path 446. The outer radial edge 434 of the barrier 426 is spaced from a pocket or section 415 of the outer side wall portion 414. Such section 415 is positioned radially outward of the outer side wall portion 414 which is upstream of such section. A first flow path 440 is defined between such edge 434 and such section 415 and extends from the top end wall portion (not shown) to the intermediate end wall portion 460. The radial location of the outer radial edge 434 of the barrier 426 is preferably approximate to the radial location of the outer side wall portion 414 at such upstream location. Below the intermediate end wall portion 460, the inner and outer edges 432 and 434 of the barrier 426 extend fully between the side wall portions 412 and 414 and/or the section 415 without any spacing therebetween, as best seen in FIG. 30. Therefore, as shown in FIG. 30, the barrier 426 joins the inner and outer side wall portions 412 and 414 along a substantial portion of the length of the channel 418.

As shown in FIG. 29, the barrier 426 also includes a radially inward or tail portion 436. The tail portion 436 extends radially inward of the inner side wall portion 412 and terminates at a junction 438. The tail portion 436 and interior radial walls 442, 444, and 422 define a plurality of exit paths 446, 450 and 454 as shown. In FIG. 29, first and second exit flow paths 446 and 450 fluidly communicate with each other at the junction 438. Preferably, none of the openings to the exit paths 446, 450 and 454 shown in FIGS. 28-30 are located at a position which is upstream of the barrier 426.

The opening 448 to the first exit flow path 446 as previously described, is defined between the inner edge 432 of the barrier 426 and the inner side wall portion 412. Such opening 448 is defined in part by the barrier 426 and thus, is not located upstream of the barrier. A second exit flow path 450 is located further downstream of the first exit flow path 446 and also lacks any openings upstream of the barrier 426. Openings 451 and 453 of the second exit flow path 450 generally allow communication between the first and third exit flow paths 446 and 454 and such openings 451 and 453 are located downstream of the barrier 426. As previously discussed, plasma may flow from the first exit flow path 446 into the second exit flow path 450 depending on the radial location of the interface. A third exit flow path 454 is located downstream of the first and second flow paths 450 and 452 and includes opening 456 which preferably allows removal of red blood cells from the channel 418. The first flow path 440 allows communication between the upstream and downstream sides of the barrier 426 but also does not allow fluid to exit the channel 418 upstream of the barrier 426. Thus, the channel 418 lacks any opening to remove fluid from the channel upstream of the barrier 418.

The channel 418 further includes a collection region 458 (shown in broken lines in FIGS. 29 and 30) downstream of the barrier 426. The collection region 458 is generally defined between the top of the channel 418 and the intermediate end wall portion 460. The collection region 458 also is generally defined between radial locations corresponding to the inner wall portion 412 and the section 415 of the outer wall portion 414. As is contemplated by the various embodiments discussed herein, the size and location of the collection region 458 may vary depending on the particular chamber design. Similar to embodiments discussed above, the first flow path 440 and the second and third exit flow paths 450 and 454— through openings 453 and 456—allow communication with the collection region 458.

Plasma or platelet rich plasma is collected radially inward of the interface between plasma and red blood cells. Such plasma is preferably is permitted to flow through the opening 448 into the first exit flow path 446 and out of the channel 418. Radially outward of the interface, red blood cells are permitted to flow through the first flow path 440 into the collection region 458 and exit through the third exit flow path 454. The second exit flow path 450 may contain either plasma or red blood cells, or both, depending on the location of the interface between the plasma and red blood cells. During normal conditions, the interface is preferably maintained between the radial locations of the outer edge 443 and the inner edge 432 of the barrier 426. For such condition, the second exit flow path 450 may primarily allow flow of plasma above such location of the interface although other flow patterns are possible.

H. Eighth Embodiment of the Blood Processing Chamber

FIGS. 31-34 illustrate a yet further embodiment of the blood processing chamber, generally indicated at 410A. The chamber 410A is similar to the chamber 410 discussed in FIGS. 28-30 and as such, similar parts will be shown with the same number followed by the designation of letter 'A'. As compared to the embodiment of FIGS. 28-30, the chamber 410A of FIGS. 31-34 includes a barrier 426A, which barrier is not formed with a tail portion, as in FIGS. 28-30. Instead, a separate intermediate radially extending wall 436A is spaced downstream of the barrier 426A and forms a portion of one or more exit flow paths.

Figure 33:
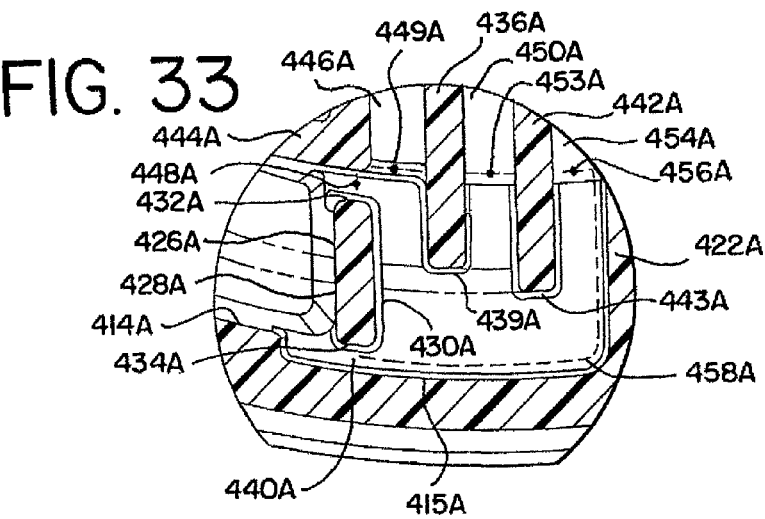
FIG. 33 is an enlarged partial top view of the encircled portion of the chamber of FIG. 31.
Figure 34:
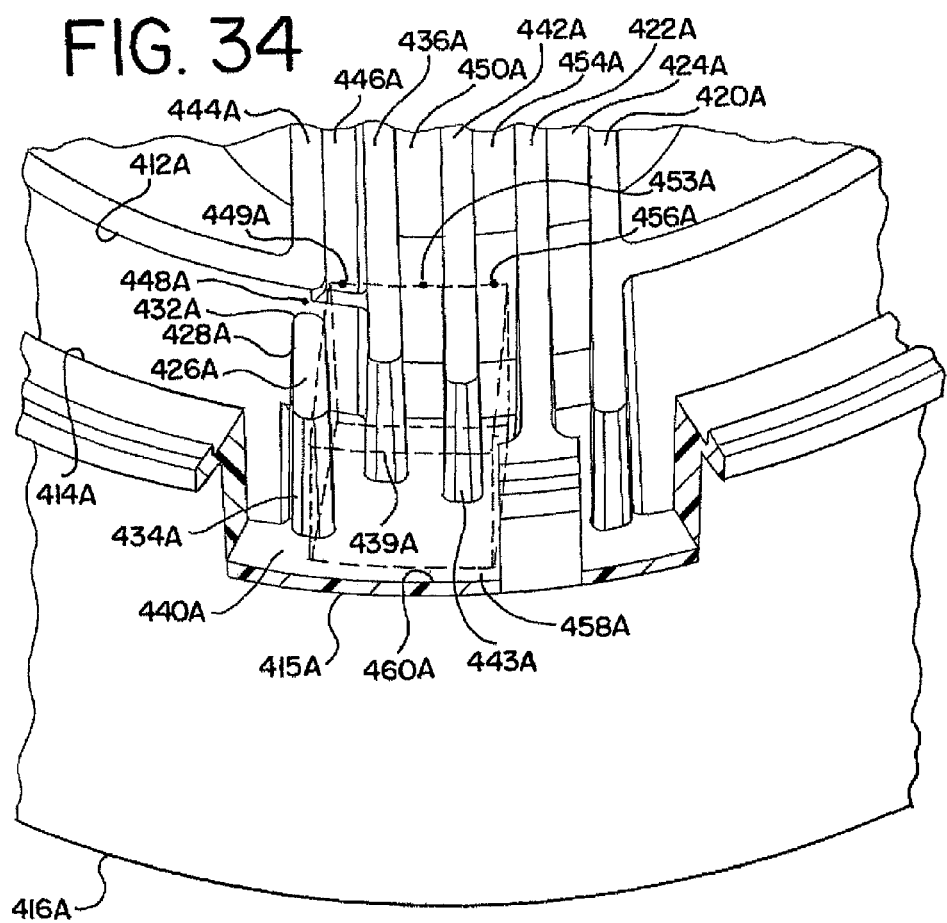
FIG. 34 is an enlarged partial top perspective view of the chamber of FIG. 31 with portions of the chamber shown in section.

As with the embodiment of FIGS. 28-30, the chamber 410A of FIGS. 31-34 includes radially spaced inner and outer side wall portions 412A and 414A and opposed end wall portions, a first end wall portion 426A being shown in FIG. 34. These wall portions 412A, 414A and 416A together define a channel 418A. Opposed interior walls 420A and 422A define an inlet 424A.

Similar to the embodiment of FIGS. 28-30, an opening or passageway 448A in FIGS. 33 and 34 is defined between the inner edge 432A of the barrier 426A and the inner side wall portion 412A. As compared to the embodiment of FIGS. 28-30, such opening 448A in FIGS. 31-34 communicates with a first exit flow path 446A but does not form the opening to the first exit flow path 446A. Instead, the first exit flow path 446A is disposed downstream of the barrier 426A and extends radially inward from an opening 449A which is formed in the inner side wall portion 412A at a location which is downstream of the barrier 426A. A portion of the first exit flow path 446A is defined between the intermediate radially extending wall 436A and an interior radial wall 444A.

At a radially inward location shown in FIG. 32, the intermediate wall 436A terminates at a junction 438A. Radially inward of the junction 438A, the first exit flow path 446A is defined between the interior walls 442A and 444A. At the junction 438A, fluid from the first exit flow path 446A may flow radially outward into the second exit flow path 450A or radially inwardly through the first exit flow path for removal from the channel 418A.

In FIGS. 32-34, the second exit flow path 450A is defined downstream of the barrier 426A between an interior radial wall 442A and the intermediate radially extending wall 436A, and includes openings 451A (FIG. 32) and 453A (FIG. 34). As previously described, the second exit flow path 450A generally allows fluid communication between, the first and third exit flow paths 446A and 454A although the actual flow will depend on the radial location of the interface. The third exit flow path 454A is defined downstream of the barrier 426A between the interior radial walls 442A and 422A and includes an opening 456A. Thus, as shown in FIGS. 32-34, each of the exit flow paths 446A, 450A and 454A and its corresponding openings are located in the channel downstream of the barrier 426A.

In FIGS. 32-34, a collection region 458A is generally defined downstream of the barrier 426A between an intermediate end wall portion 460A and the top end wall (not shown) of the channel 418A, and is further generally defined between the inner side wall portion 412A and a radially outer portion 415A of the outer side wall portion 414A. A first flow path 440A communicates between the upstream and the downstream sides 428A and 430A of the barrier 426A and is in fluid communication with the collection region 456A. Downstream of the barrier 426A, one or more of the openings 449A, 453A and 456A may communicate with the collection region 458A depending on the radial location of the interface.

As best seen in FIGS. 33 and 34, the intermediate radially extending wall 436A terminates at a radially outward edge 439A. The radially outward edge 439A is located in the collection region 458A at a radial location which is radially intermediate the inner and outer side walls portions 412A and 414A. A radially outward edge 443A of the adjacent interior wall 442A also extends into the collection region 458A and is located an intermediate radial location, which location is preferably radially outward of the radial location of the other edge 439A. During normal conditions, the interface is preferably located between the radial locations of the edges 439A and 443A. Plasma or platelet rich plasma radially above the interface preferably is allowed to flow into the first exit flow path 446A—and may flow in either a radially inward or radially outward direction at the junction 438A. Red blood cells radially outward the interface are preferably allowed to flow into the third exit flow path 454A and exit the channel 418A.

I. Ninth Embodiment of the Blood Processing Chamber

Turning to FIGS. 35-38, an additional embodiment of the chamber, generally indicated at 410B, is shown. The chamber 410B is similar to the previous chambers 410 and 410A as described in FIGS. 31-34 and as such, corresponding alpha numeric references which include the letter 'B' will be used to describe the chamber 410B. As compared to the embodiments of FIGS. 31-34, the outer side wall portion 414B of the chamber 410B of FIGS. 35-38 does not include a radially outward section or pocket.

As previously described, a first flow path 440B and a passageway 448A allow communication between the upstream and downstream sides of the barrier 426B. A first flow path 440B is defined in an axial direction between an outer radial edge 434B of a barrier 426B and the outer side wall portion 414B and extends in a radial direction from the top end wall (not shown) of the channel 418B to an intermediate end wall portion 460B. An opening or passageway 448B is defined in a radial direction between the inner side wall portion 412B and the inner radial edge 432B of the barrier 426B and is defined in an axial direction between the top of the channel to the intermediate end wall portion 460B. Below the intermediate end wall portion 460B, the barrier 426B extends fully across the radial extent of the channel 418B to join the inner and outer side wall portions 412B and 414B all the way to the bottom of the channel.

As shown in FIGS. 36 and 37, a collection region 458B communicates with two exit flow paths 446B and 454B through corresponding openings 449B and 456B to preferably allow removal of plasma and red blood cells, respectively, from the channel 418B. The collection region 458B further includes an intermediate radially extending wall portion 436B spaced downstream of the barrier 426B and spaced upstream of the exit flow paths 446B and 454B. As compared to the embodiment of FIGS. 31-34, the intermediate radially extending wall portion 436B in FIGS. 35-38 does not extend radially inward of the inner side wall portion 412B. As best seen in FIG. 36, the intermediate wall portion 436B has inner and outer edges 438B and 439B, respectively, which edges are preferably spaced from the corresponding inner and outer side wall portions 412B and 414B. In FIGS. 37 and 38 the radially extending wall portion 436B preferably is located closer to the inner side wall portion 412B which may allow for priming portions of the chamber 410B although other locations of the radially extending wall portion 436B are possible depending on the flow requirements of the procedure.

In FIG. 37, the interface between the plasma and red blood cells is preferably located approximately between the edges 439B and 443B during normal conditions—i.e. not under spill or over spill conditions. Plasma radially inward of the interface is preferably allowed to flow from the collection region 458B into the opening 449B and the exit flow path 446B for removal of plasma from the channel 418B. Red blood cells radially outward of the interface are preferably allowed to flow into the opening 456B and through the exit flow path 454B for removal of red blood cells from the channel 418B.

J. Tenth Embodiment of the Blood Processing Chamber

Figure 39:
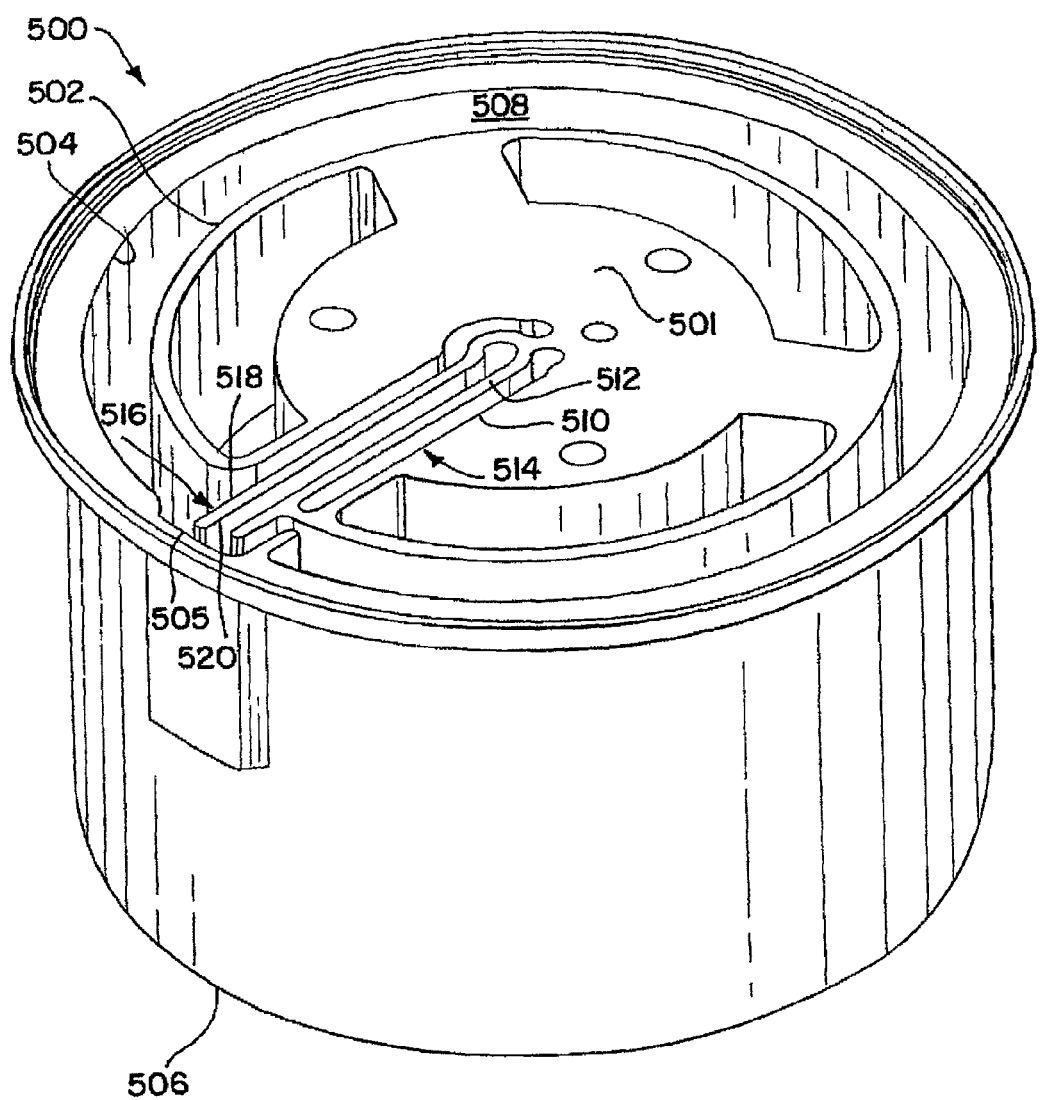
FIG. 39 is a perspective view of the interior of a tenth embodiment of the chamber of the type shown in FIG. 7, which is configured to perform a fluid separation and collection procedure using the device shown in FIGS. 5 and 6.
Figure 40:
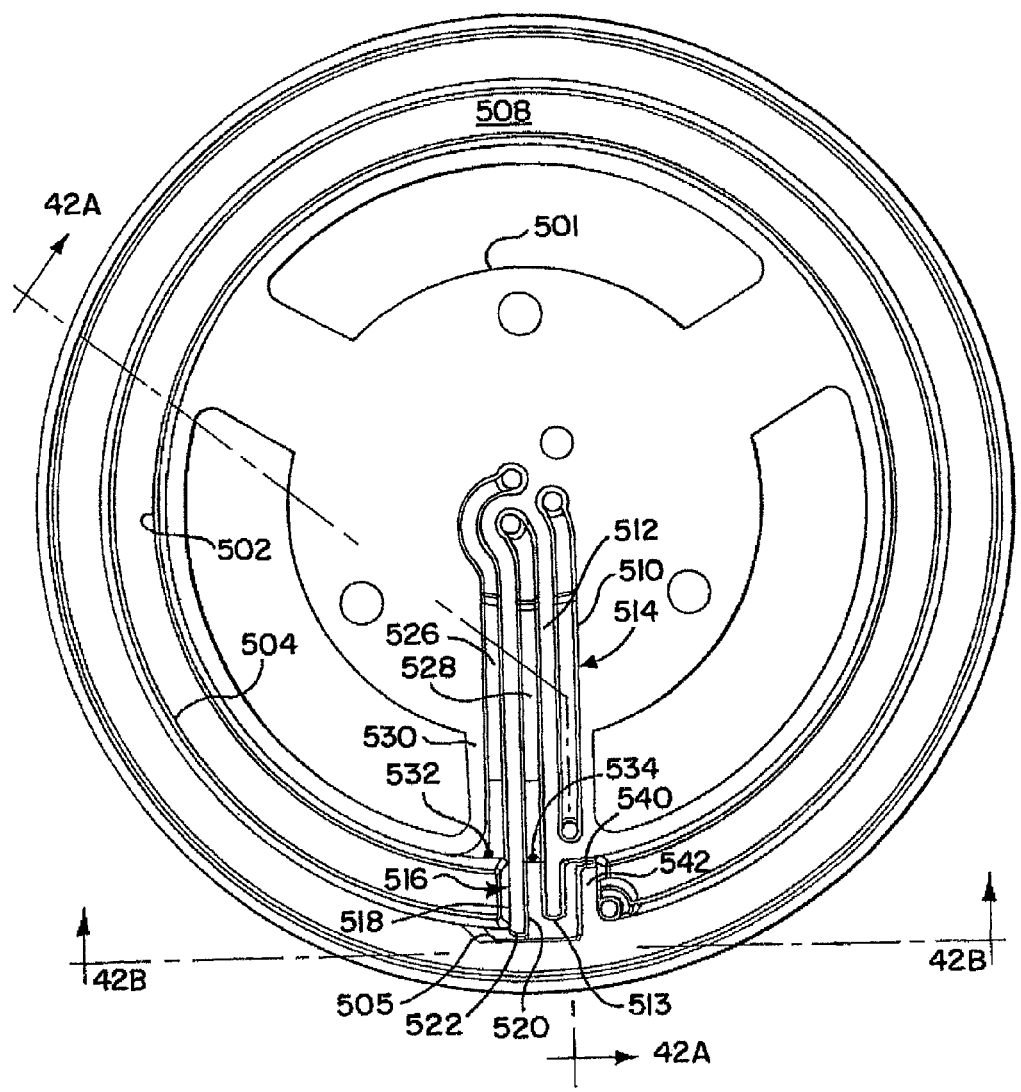
FIG. 40 is a top view of the chamber of FIG. 39.
Figure 40A:
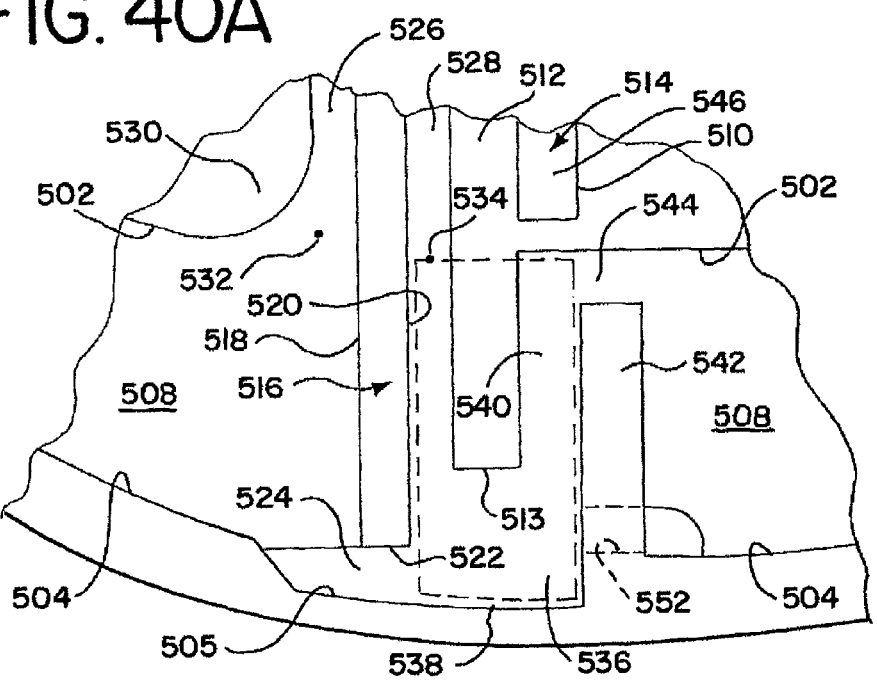
FIG. 40A is an enlarged top view of the chamber of FIG. 39.
Figure 41:
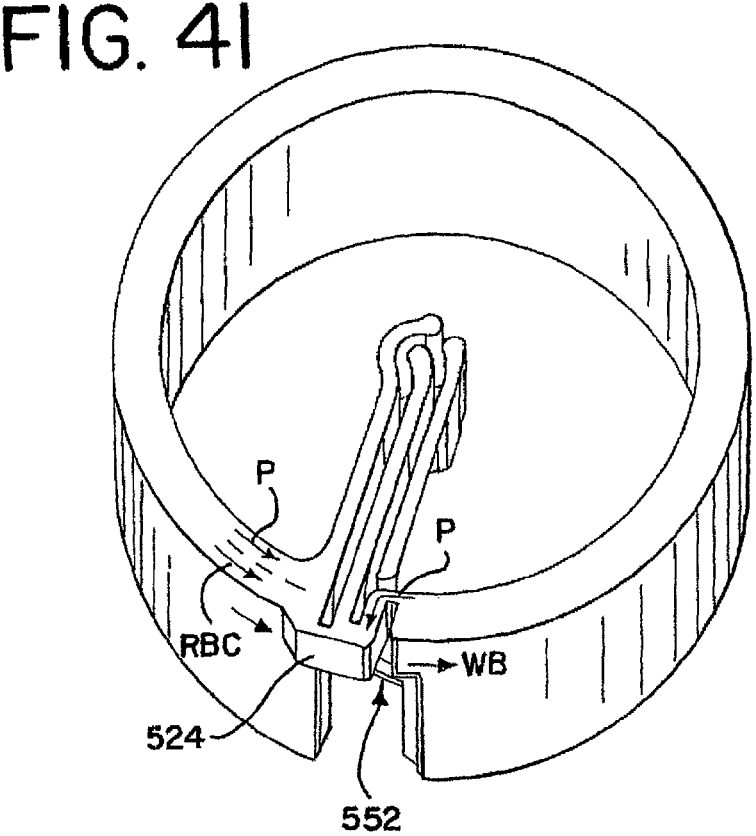
FIG. 41 is a perspective view of the fluid flow within the chamber shown in FIG. 39, with the chamber removed, so as to show the path of the fluid inside the chamber.

FIGS. 39-42B illustrate another embodiment of a blood separation chamber, generally indicated at 500, with FIG. 41 illustrating the path traveled the blood within the chamber 500. As with previous embodiments already discussed, chamber 500 includes inner and outer side wall portions 502 and 504 respectively and opposed end wall portions (one end wall portion 506 being shown in FIG. 39) which together define a channel 508. The outer side wall portion 504 includes a radially outward section 505 (FIGS. 39 and 40A) which is positioned radially outward of the outer side wall portion 504 of a more upstream location.

Figure 42B:
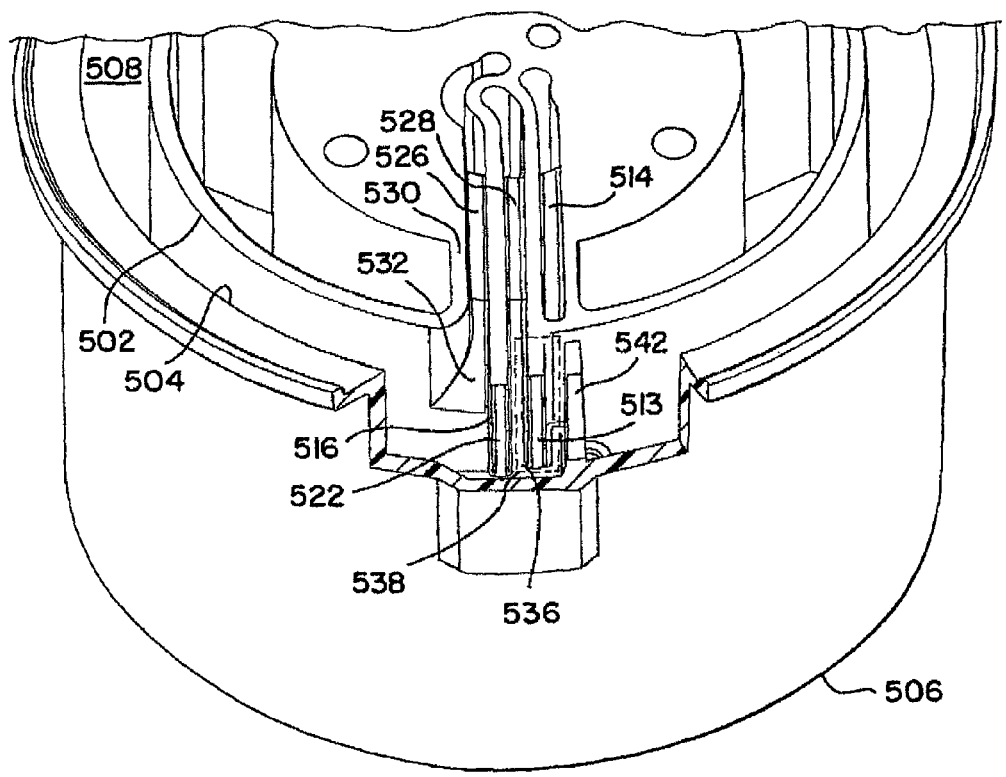
FIG. 42B is a partial sectional view along the line 42B-42B of FIG. 40.
Figure 42A:
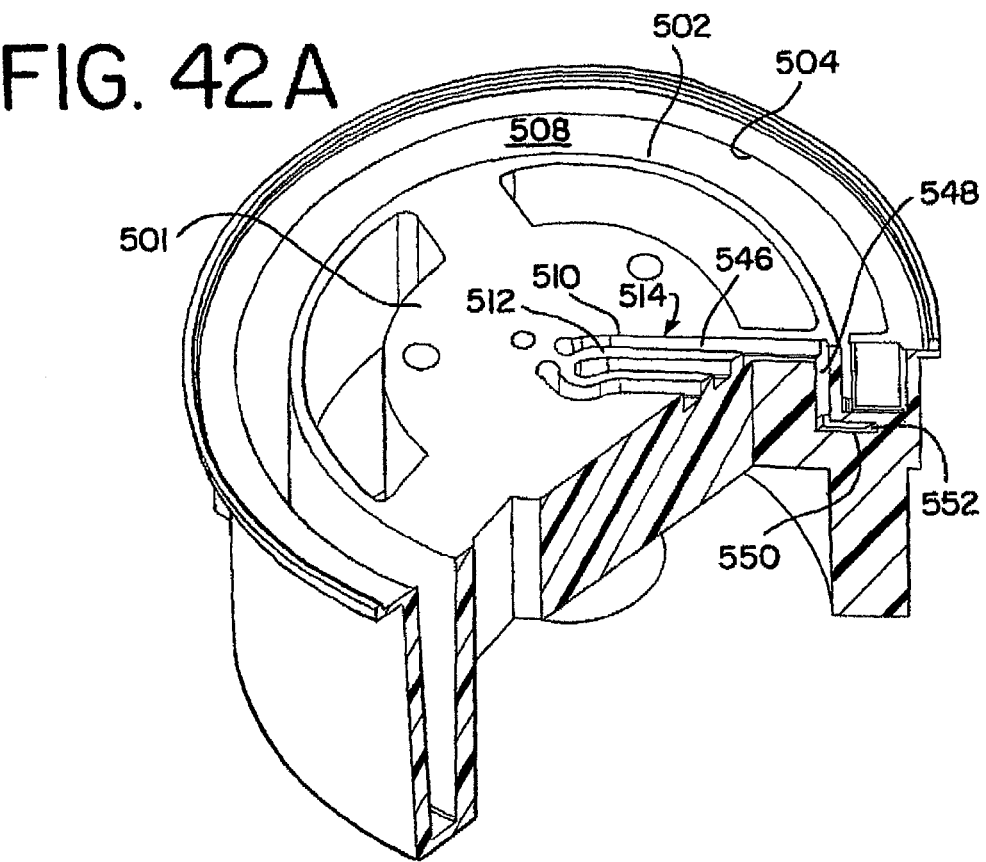
FIG. 42A is a partial sectional view along the line 42A-42A of FIG. 40.

Two radially directed interior radial walls 510 and 512 define an inlet, generally at 514, which extends outward from a hub 501. As best shown in FIG. 42A, the inlet 514 includes several portion 546, 548, 550 and 552 which are generally disposed in different directions. A first portion 546 extends radially outward of the hub 501 between the interior radial walls 510 and 512 and is defined in part by the top end wall portion (not shown). A second portion 548 is axially directed from one end of the first portion 546 and is defined between the top end wall portion and an intermediate axial location of the chamber 500. A third portion 550 is radially directed from one end of the second portion 548 and is axially offset from the first portion 546 of the inlet 514. Another end of the third portion 550 is defined at a radially outward location which is approximate to the outer side wall portion 504. A fourth portion 552 is disposed generally orthogonal to the third portion 550 and is directed towards an upstream end of the channel 508 so as to allow fluid to enter the channel 508. In FIG. 41, the fluid path defined by the fourth portion 552 is generally parallel to the fluid path defined by the channel 508. As shown in FIG. 41, fluid enters the channel 508 at a location which is axially spaced from the top end wall portion at the top of the channel 508.

As with previous embodiments, the channel 508 in FIG. 39 includes a barrier, generally indicated at 516, having upstream and downstream sides 518 and 520. The barrier 516 extends generally perpendicular to the outer side wall portion 504. In FIGS. 40A and 42B, an outer edge 522 of the barrier 516 is spaced from the radially outward section 505 above an intermediate end wall portion 536 and thus defines a first flow path 524 (as best seen in FIGS. 40A and 41). Above the intermediate end wall portion 536, the first flow path 524 permits flow around the outer radial edge 522 of the barrier 516. The edge 522 has a radial location approximate to that of the outer wall portion 504. The first flow path 524 is preferably defined axially between the top end wall portion (not shown) of the channel 508 and the intermediate end wall 536, which intermediate end wall is spaced from the bottom end wall portion 506 of the channel. Below the intermediate end wall 536, the outer radial edge 522 joins the outer side wall portion 504 or section 505 thereof so that flow around the barrier 516 is generally not permitted.

In FIGS. 40, 40A and 42B, the barrier 516 preferably extends radially inward to a radial location which is radially inward of the inner side wall portion 502. The barrier 516 forms a partition between first and second exit flow paths 526 and 528. As shown in FIGS. 40 and 40A, the first exit flow path 526 is defined between the upstream side 518 of the barrier 516 and an interior radial wall 530. An opening or outlet 532 to such path is disposed at the inner side wall portion 502 to allow flow out of the channel upstream of the barrier 516. The second exit flow path 528 is disposed downstream of the barrier 516 and includes an opening 534. The second exit flow path 528 is defined between the barrier 516 and the interior radial wall 512. A radially outward edge 513 of the interior radial wall 512 is disposed at a radial location which is intermediate the inner and outer side wall portions 502 and 504. Such edge 513 is preferably radially inward of the outer edge 522 of the barrier 516.

As best seen in FIG. 40A, a collection region 538 is disposed downstream of the barrier. The collection region preferably is defined in an axial direction between the top end wall portion (not shown) and the intermediate end wall portion 536 (see also FIG. 42B) which is spaced from the bottom end wall portion 506. The collection region 538 is in fluid communication with the first flow path 524. In FIG. 40A, the collection region 538 is preferably defined in its radial extent between the inner side wall portion 502 and the radially outward section 505 of the outer side wall portion 504. The opening 534 communicates with the collection region 538 to allow flow of one or more fluid components, preferably red blood cells, to exit through the exit flow path 528 and for removal from the channel 508.

In FIG. 40A, the collection region 538 further includes a radial passageway 540 located to the right of the interior radial wall 512. The passageway 540 is defined between the interior radial wall 512 and an extension portion 542 which portion extends radially inward from the outer side wall portion 504. The passageway 540 extends to the inner side wall portion 502 where it communicates through a non-radial passageway 544 with the portion of the channel 508 located to the right in FIG. 40A. The extension portion 542 terminates at a radial location which is intermediate the inner and outer side wall portions 502 and 504 and, preferably, terminates at a radial location which is radially inward of the edge 513. The extension portion 542 thus locates the non-radial passageway 544 at a location adjacent the inner side wall portion 502. Preferably, both radial and non-radial passageways 540 and 544 are axially defined between the top end wall portion (not shown) and the intermediate end wall portion 536.

As shown in FIG. 40A, the passageways 540 and 544 generally allow communication between the upstream and downstream ends of the channel 508. In this regard, the passageway 544 preferably allows plasma to flow into the collection region 538 from the portion of the channel 508 to the right of the passageway 544. As shown in FIG. 41, plasma flows to the left of the extension portion 542. Plasma preferably flows into the collection region 538 when the interface is located at an approximate radial location between the edges 513 and 522. As previously described, FIG. 42A shows the inlet 514 and its portions 546, 548, 550 and 552 which are disposed so as to circumvent a path around the passageways 540 and 544 into the channel 508. The positioning of the inlet portion 552 at the inner side wall portion 502 may help to avoid the flow of whole blood or other fluids into the collection region 538 before the components have the opportunity to undergo sufficient separation.

In FIG. 40A, plasma preferably exits the channel 508 through the opening 532 of the first exit flow path 526 to the left of the barrier 516 in FIG. 40A. Plasma is also allowed to flow through the passageway 544 into the collection region 538 to the right of the barrier 516 in FIG. 40A so as to maintain a volume of plasma above the radial location of the interface. Red blood cells preferably exit through second exit flow path 528. During normal conditions, the interface in the collection region 538 is preferably located between the outer edge 522 of the barrier 516 and the edge 513 formed on the interior wall 512. Plasma is supplied through the passageway 544 to fill at least a portion of the volume of the collection region 538 radially inward of the interface. The radial location of such edge 513 preferably does not allow plasma to flow into the second exit flow path 528.

III. Use of the System to Perform a Concentrated Platelet Collection Procedure

Any of the above described embodiments may be utilized to perform various biological fluid collection procedures such as a plasma collection procedure, a double-red cell collection procedure, and a platelet collection procedure as well as other collection procedures. Such procedure may be conducted with the blood flow set 12 together with the device 14 and controller 16 previously described. The blood separation chamber in FIGS. 43-48 will generally be referred to by reference number 18 which may include the structure of any of the previously described embodiments.

Although several platelet collection procedures will be described below, it is understood that the above described embodiments may be used for other collection procedures and may employ more than one collection procedure. By way of example and not limitation, typical plasma and double-red collection procedures have been described in at least one of the above-identified patents or applications which have been incorporated by reference herein. In addition, any of the embodiments described herein may be employed to collect more than one blood component in quantities permitted by the relevant country. Although collection of platelet rich concentrate will be discussed in detail below, it is contemplated that any of these methods in its broadest interpretation may include other biological fluid components as well as other blood components.

A. Recirculating for Platelet Collection

Figure 43:
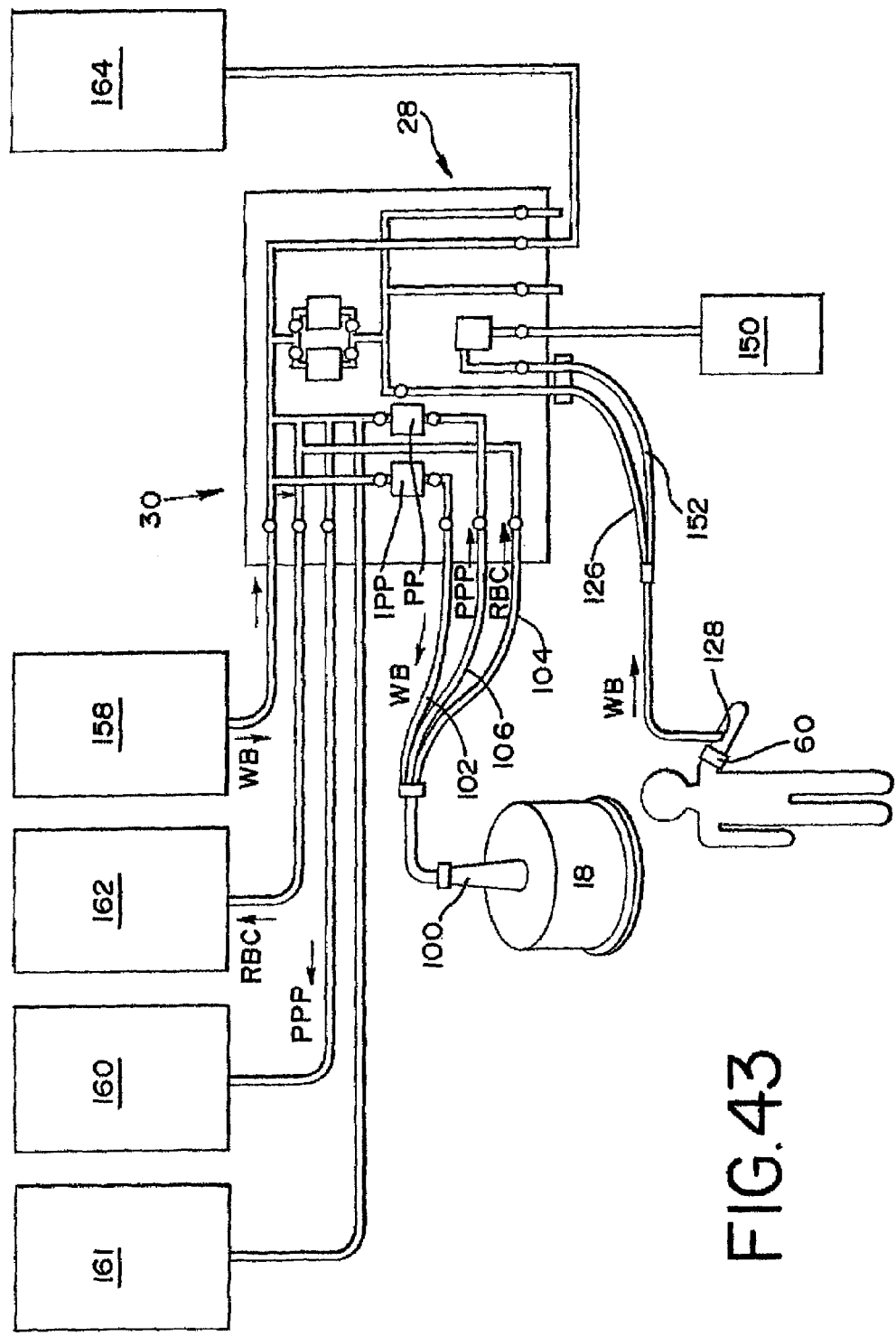
FIGS. 43-45 are schematic views of a fluid circuit that can be implemented in accordance with one of the fluid collection methods described herein.
Figure 44:
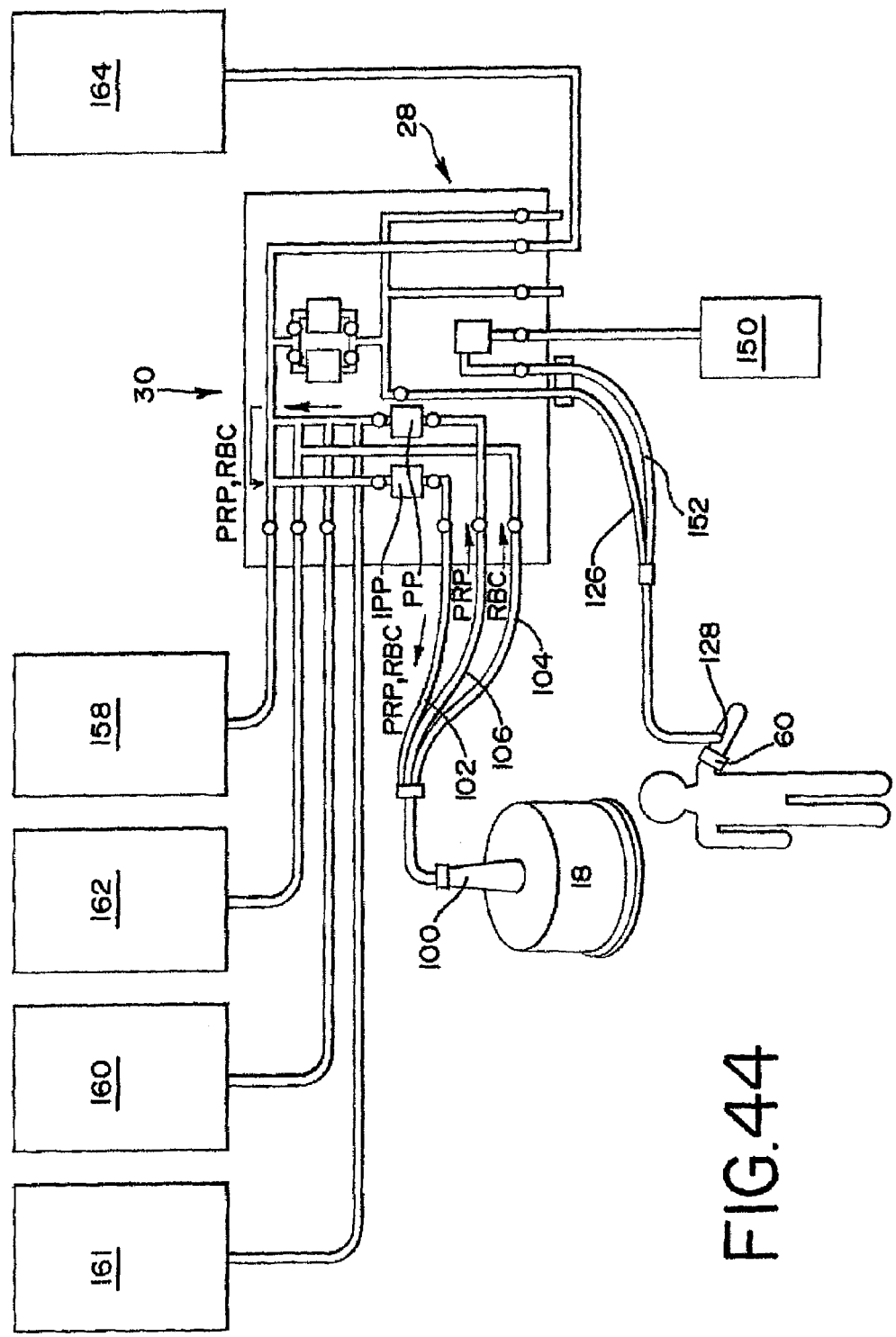
Figure 45:
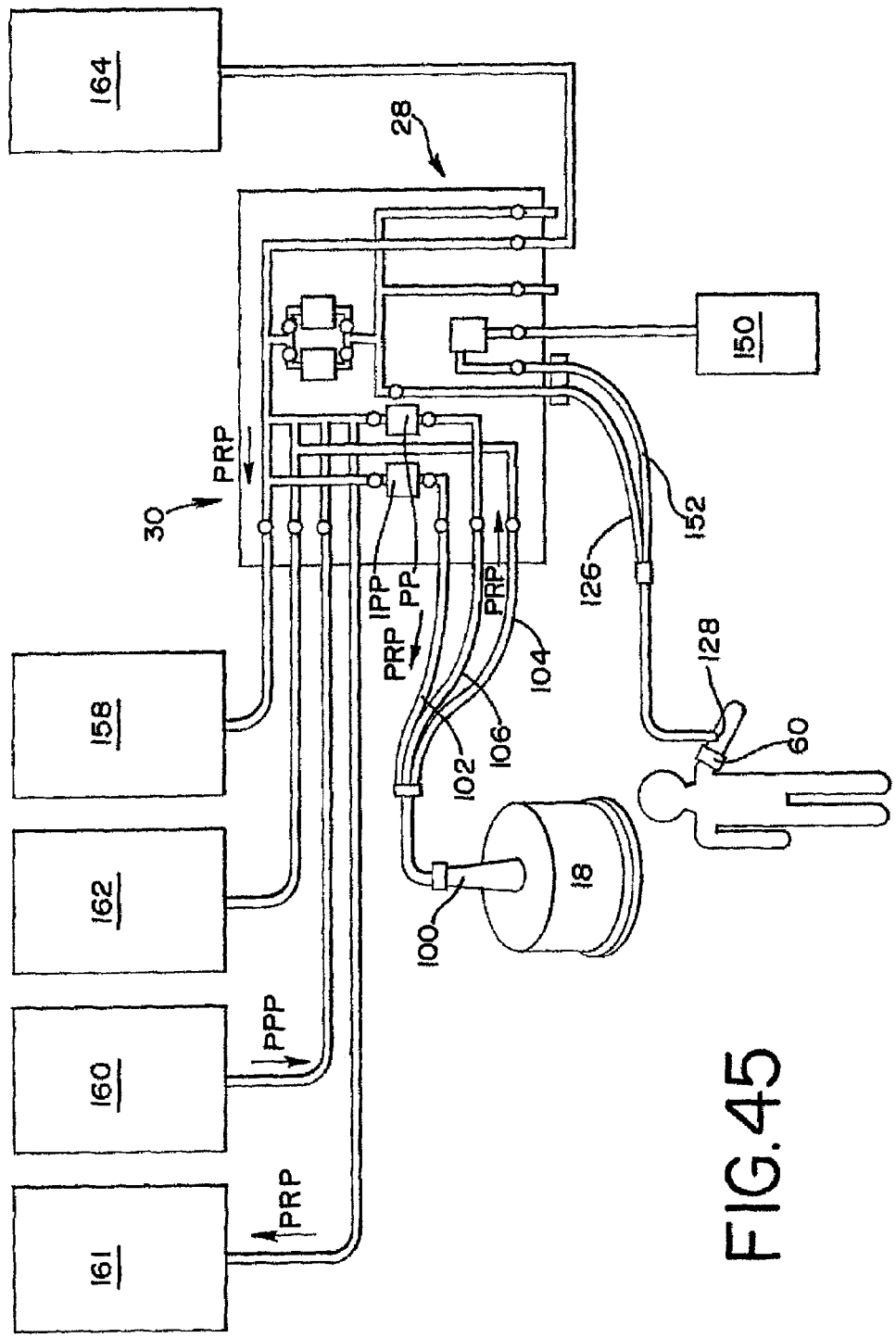

FIGS. 43-45 schematically show a method for platelet collection. In FIG. 43, a fluid component, preferably whole blood, is pumped into the chamber 18. The blood may flows into the chamber 18 either from a blood source, preferably a donor, or may flow from the in-process container 158 where the blood from the blood source is temporarily stored for subsequent processing by the chamber 18. The whole blood WB is allowed to flow, such as by pumping of an in-process pump IPP, through an inlet flow line 102 into the chamber 18.

Within the chamber 18, separation of the fluid components occurs based on density as in FIG. 11. As mentioned above, further detail of this separation is set forth in Brown, "The Physics of Continuous Flow Centrifugal Sell Separation," Artificial Organ, 13(1):4-20 (1989). A higher density component such as red blood cells RBC is forced towards the outer or high-side wall portion and a lower density component such as platelet poor plasma is forced towards an inner or low-g side wall portion. In FIG. 11, the interface between the red blood cells and the plasma contains a buffy coat layer which includes at least a portion of platelets and white blood cells, although the components of the interface will vary based on the particular procedure employed.

After sufficient time has passed to allow the interface to form, fluid may be collected separately from either side of the interface—or both sides thereof—through the respective outlet tube 104 or 106 depending on the requirements of the procedure. For example, some platelet poor plasma PPP may be collected radially inward of the interface through the outlet tube 106 and into the plasma collection container 160. Some red blood cells RBC may be collected radially outward of the interface through the outlet tube 104 and flow into the red blood cell collection container 162. The afore-described barriers in the above chambers preferably allow accumulation of platelets which are contained in the buffy coat during such plasma or red cell collection, but platelet collection is not yet initiated.

Figure 13:
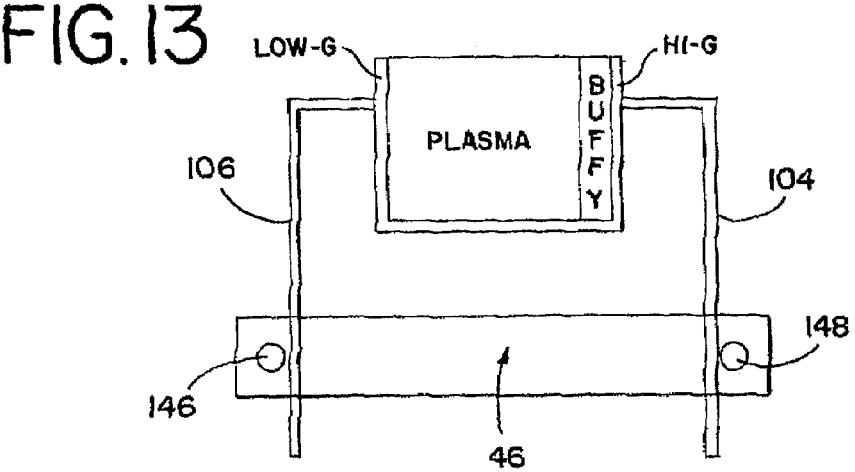
FIG. 13 is a diagrammatic view of the interior of the blood processing chamber of a type shown in FIG. 7, with the buffy coat layer having moved very close to the high-G wall, creating an under spill condition that leads to a reduction of the hematocrit of red blood being collected.

Prior to collecting the platelets, it is preferred that an under spill condition is imposed upon the fluid components. The under spill condition is shown in FIG. 13. The optical sensor 148 detects that a portion of the plasma is exiting the tube 104 which usually has red blood cells exiting therethrough. The under spill condition is empirically determined based on the optical transmissivity of light through the components in the outlet tube 104. The optical sensor data is converted to a hematocrit. A decrease in hematocrit of the outlet tube 104 detects an under spill condition. Forcing an under spill condition allows the interface to be forced radially outward (FIG. 13) as compared to the radial location of the interface during normal collection operation (FIG. 11). The under spill condition allows removal of red blood cells into the red blood cell collection container 162 until the resulting fluid in the chamber has a hematocrit of approximately in the range of 20 to 40 percent.

Once a desired hematocrit level is achieved, the fluid in the chamber 18 is preferably kept within the desired hematocrit range. For example, the flow of plasma may be stopped to prevent flow to plasma collection container 160 and the flow of red blood cells from the chamber 18 may also be stopped. Such flow may be stopped by operation of the valve station 30 and/or stopping one or more pumps such as the plasma pump PP. The in-process pump IPP may continue to operate although it is preferably operated at a lower flow rate.

The method further includes the recombination of the separated fluid components within the chamber 18. Recombination is preferably performed by rotation of the chamber in both clockwise and counterclockwise directions. Preferably, the chamber 18 is rotated alternately in clockwise and counterclockwise directions one or more times. The step of recombining preferably results in a uniform blood mixture which includes plasma, red blood cells, platelets and white blood cells having an approximate chamber hematocrit as previously described. The step of recombining preferably lasts approximately one to three minutes, although this time period may vary. The rotation of the chamber in either direction is preferably at a rate preferably greatly reduced than the rate of rotation during initial separation of the components and may be, for example, in the range of approximately 300 to 600 RPM, although other rates of rotation are possible. It is noted that the angular velocities used herein conventionally are two omega although one omega may also be used as well as some combination thereof.

After a sufficient recombination period, the rotor is then restarted to rotate the chamber in a uniform direction so that the flow within the chamber is generally directed from the inlet tube 102 to the outlet tubes 104 and 106. Although the specific speed of the rotor may vary, such speed may be 2500 RPM. The interface between the plasma and red blood cells is allowed to reform. Preferably, collection of the plasma and red blood cells from the chamber 18 is not initiated until the interface is allowed sufficient time to reform.

After the interface has reformed, the plasma and in-process pumps are operated to draw off plasma from the radially inward side of the interface through the outlet tube 106 and red blood cells are drawn from the radially outward side of the interface through flow line 104. As shown in FIG. 44, both components are diverted back through the inlet tube 102 for recirculation through the chamber 18. During recirculation, no plasma or red blood cells are collected into their containers 160 and 162. The platelet concentration in the plasma generally increases during recirculation with platelets from the interface becoming suspended in the plasma. Recirculation of both components continues until the optical sensor 146 detects platelet rich plasma which has a desired concentration of platelets and which is visually low in red blood cells. As discussed above, the hematocrit of the recirculated mixture is approximately between 20-40 percent. Recirculation may also be modified so as to recirculate only one of the components, either plasma or red blood cells, as desired.

Figure 45A:
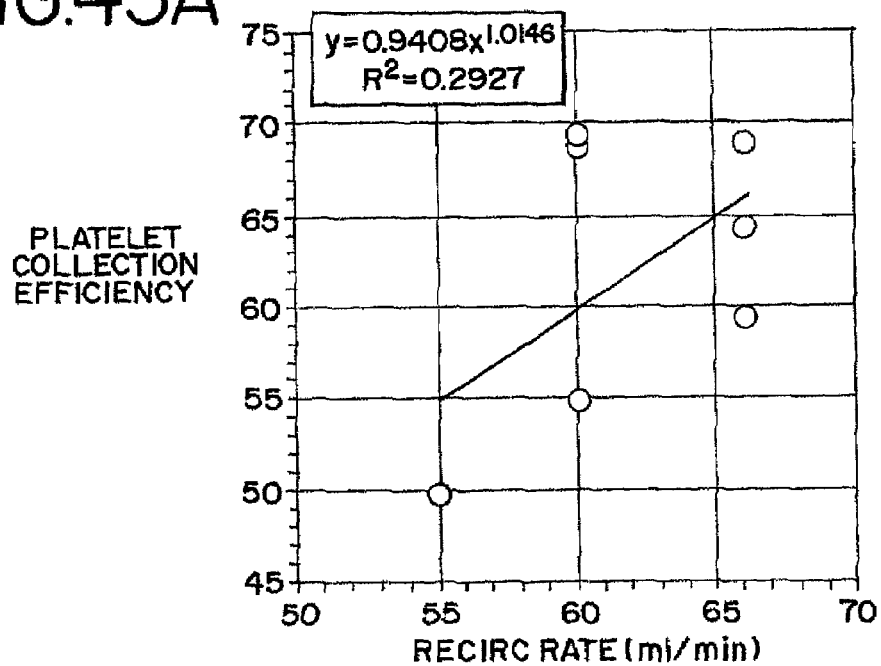
FIG. 45A is a graphical representation of the recirculation rate (in ml/min) versus the platelet concentration in a sample collected radially inward of the red blood cell and plasma interface which has been collected after a predetermined period of recirculation.
Figure 45B:
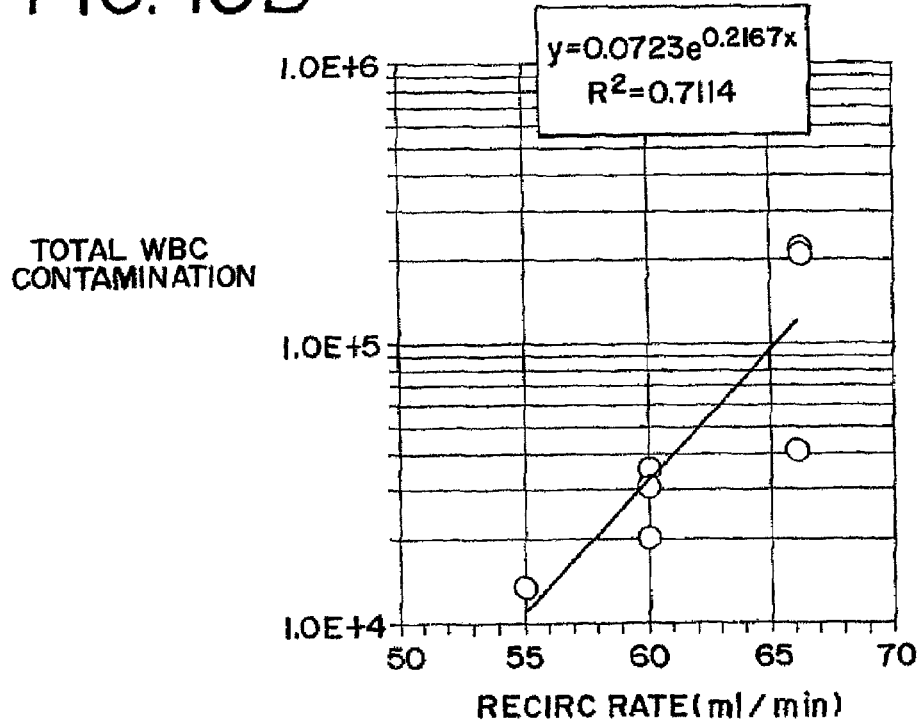
FIG. 45B is a graphical representation of the recirculation rate (in ml/min) versus the white blood cell count a sample collected radially inward of the red blood cell and plasma interface which has been collected after a predetermined period of recirculation.

During recirculation, the preferred pump flow rate ratio of the in-process pump IPP and plasma pump PP is 60/40, although other pump rates may be used depending on the particular conditions of the system. Recirculation may also allow an increasing concentration of white blood cells to settle to the interface between the platelet rich plasma and the red blood cells. Such pump ratio has also been found to have a direct influence on the number of white blood cells WBC that contaminate the platelet rich plasma PRP and the overall platelet concentration collection efficiency. By way of example and not limitation, FIGS. 45A and 45B show a collected fluid having a higher concentration of platelets (FIG. 45A) and a lower concentration of white blood cells WBC (FIG. 45B). In FIGS. 45A and 45B, such fluid was collected from a chamber having approximately 120 $cm^2$ surface area, which was operated at a one omega speed of approximately 1250 RPM with a chamber hematocrit of approximately 25%. Other collection efficiencies may be developed for different chamber surface areas, centrifugal speeds and chamber hematocrits.

Recirculation of the platelet rich plasma PRP may continue for several minutes, preferably approximately two to four minutes although this range may very depending upon the particular procedure. After a sufficient recirculation period, the platelet rich plasma PRP is collected through the outlet tube 106 into the platelet concentrate PC container 161 as shown in FIG. 45. Also, in FIG. 45, platelet poor plasma PPP replaces the fluid volume lost within the chamber 18 due to collection of the platelet rich plasma PRP. Although the collection of platelet rich plasma PRP has been described above, this method may also employ collection of platelet poor plasma and/or red blood cells.

Various modifications to the above-described method are possible. One modification includes operating the in-process pump IPP between at least two different pumping rates to effect recombination of the blood components. For example, fluid may be pumped into the chamber 18 by the in-process pump IPP at a first flow rate while being rotated in a clockwise or counterclockwise direction, and then the rotation in either direction is repeated at a second flow rate. The centrifugal force may be decreased, such as by decreasing the rotor speed, where more than one flow rate is used.

Another modification to includes operating the plasma pump PP during recombination. Plasma is collected through the outlet tube 106 and flows into the in-process container 158. Simultaneously, the flow at the inlet tube 102 is reversed using the in-process pump IPP so that fluid from the chamber 18 also flows into the in-process container 158 through the inlet tube 102. The fluid in the in-process container 158 is then allowed to flow back into the chamber 18 through the inlet tube 102. Therefore, the fluid components are mixed together outside of the chamber 18 and then re-enter the chamber.

It is further possible to modify the pump ratio between the in-process IPP and plasma pumps PP during the collection phase to different ratios at different times during the procedure. Another further modification to the method discussed above includes using a platelet additive solution to replace volume within the chamber 18 after the platelet rich plasma PRP has been collected.

Figure 45C:
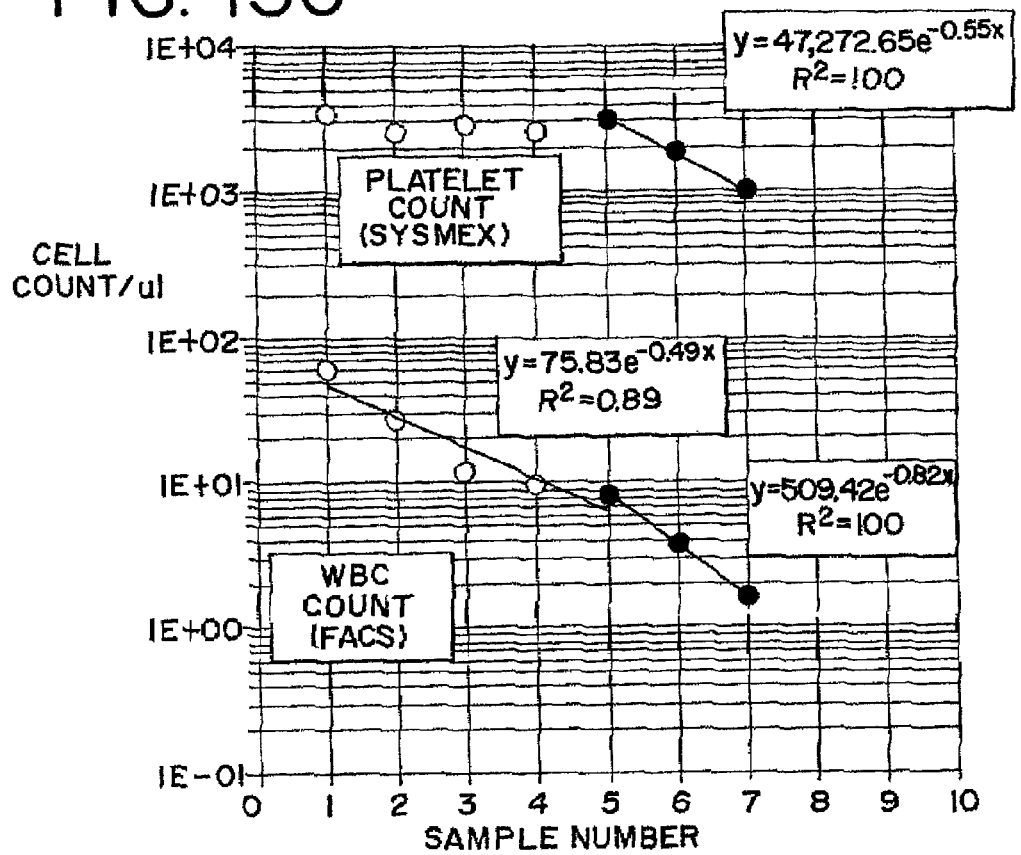
FIG. 45C shows a graphical representation of both platelet and white blood cell concentrations observed during various times during recirculation.

In addition, the length of time of recirculation into and out of the chamber 18 may be modified. For example, lengthening the recirculation period may allow more white blood cells to be forced radially outward to the interface so that the collected platelet rich plasma PRP has a lower white blood cell count. By way of example and not limitation, FIG. 45C shows platelet and white blood cell counts during recirculation of platelet rich plasma PRP. In FIG. 45C, the first sample occurred 15 seconds after the plasma pump was restarted for recirculation with samples taken approximately every minute thereafter. Sample #5 occurred 15 seconds after beginning collection of platelet rich plasma PRP into the platelet concentrate container 161. The white blood cells concentration drops during recirculation, approximately halving with every sample during the first few minutes. As a result, the lengthening of the recirculation period allows more white blood cells to sediment out of the platelet rich plasma and thus produces a leuko-reduced platelet concentrate which has substantially less white blood cells than at the start of recirculation. Other modifications are also possible.

B. Decreasing the Centrifugal Force for Platelet Collection

Another method of platelet collection includes decreasing the centrifugal force in order to separate and collect a desired fluid from the chamber. Such fluid is preferably platelet rich plasma PRP which provides a combination of platelets and plasma having a high platelet concentration.

Similar to the previously described method of FIGS. 43-45, this method includes introducing a fluid, preferably whole blood, into any one of the previously described chambers. Centrifugal force is preferably applied by the rotation of the chamber about its axis which causes the separation shown in FIG. 11. Platelets and white blood cells generally settle into the interface or buffy coat layer between the plasma and the red blood cells. Within the interface, at least some separation may occur between the platelets and white blood cells based on density. In this regard, a thin layer of platelets may lie adjacent the plasma. By way of example and not limitation, a rotational speed in the range of approximately 4,500 to 5,000 RPM preferably results a platelet layer within the interface, of approximately 1 to 3 mm thick, although other speeds are also possible.

Figure 46:
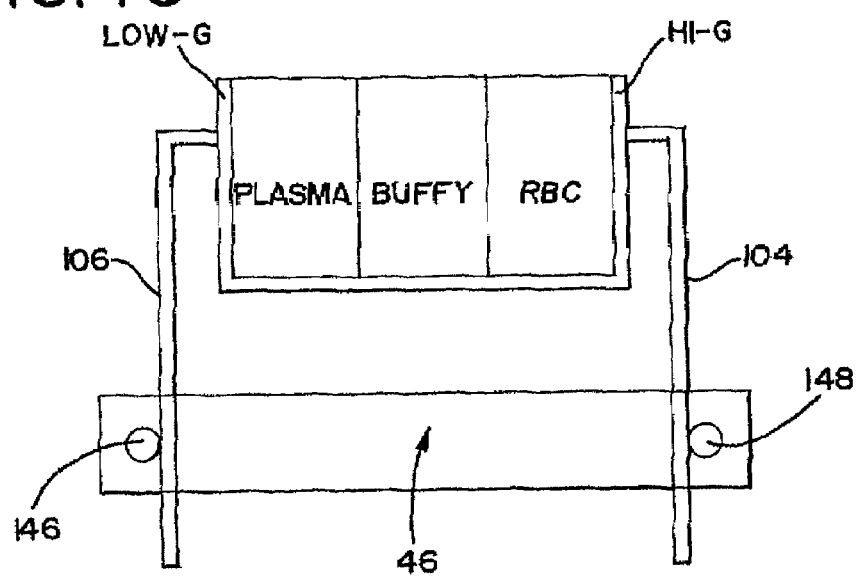
FIG. 46 is a diagrammatic view of the interior of the chamber of the type shown in FIG. 7, showing separation of whole blood in accordance with another method which includes the step of decreasing the centrifugal force to expand at least one of the separation layers.

After initial separation, the centrifugal force is decreased. Such decrease in force is preferably performed by decreasing the rotational speed of the chamber. The decrease in centrifugal force is preferably sufficient to cause expansion of the platelet layer which resides in the interface, thereby also causing expansion of the interface, as shown in FIG. 46. By way of example and not limitation, a rotation speed of preferably approximately 2,500 RPM provides a platelet layer which is approximately 4 to 6 mm thick.

Upon thickening of the interface, it is desired to collect as many platelets as possible from the interface or buffy coat, as platelet rich plasma PRP. By way of example and not limitation, collection may be performed by moving the expanded interface radially inward toward the inner side wall portion or low-G wall to create an over spill condition, similar to that shown in FIG. 12. In this respect, the optical sensor 146 optically monitors the presence of platelets in the outlet tube 106. At such point, when a sufficient concentration of platelets are detected within the outlet tube 106, the fluid flow from the chamber 18 is allowed to flow into the platelet collection PC container 161. Prior to such point, the fluid flow from the chamber 18 may flow into the plasma collection container 160.

Modifications to this method are also possible and such modifications are not limited by the specific structures shown and described herein. In addition, this method may be combined with any of the other methods described herein. Removal of platelets may be performed two or more times during the collection procedure. It is also possible to perform other collection procedures in combination with this method such as separate collection of platelet poor plasma and/or red blood cells.

C. Repeatedly Forming the Interface for Platelet Collection

This method provides for collection of a fluid from one side of the interface and then allows the interface to reform preferably to perform another collection of such fluid. Similar to previous methods discussed above, this method preferably introduces whole blood into the chamber and separates the blood into components based on density, as shown in FIG. 11. The interface or buffy coat layer is located at an intermediate radial location between the plasma and red blood cells and contains platelets.

Collection of the platelets within the interface is performed by forcing an over spill condition whereby the interface is forced radially upward to the inner side wall portion or low-G wall, as shown in FIG. 12. As previously described, platelets are optically monitored in the outlet tube 106 by the optical sensor 146 and platelet rich plasma PRP is diverted to the platelet collection container 161 when the optical sensor 146 detects the presence of a sufficient concentration of platelets within the plasma.

After a predetermined collection time period, collection is stopped and the interface is allowed to return to its previous intermediate radial location, as shown in FIG. 11. At such location, the interface is allowed time to reform so that platelets which may have moved or diverged from the interface may settle back into the interface. After sufficient time has been allowed for reforming the interface, another over spill over condition is employed so as to allow the interface to move radially inward and to allow more platelet rich plasma PRP to be collected through the outlet tube 106.

In one modification, the step of removing platelet rich plasma may be repeated at least two times and the interface may be allowed to reform between each successive removal event. In a further modification, this method may be combined with any of the other methods discussed herein. By way of example and not limitation this method may be combined with decreasing the centrifugal force as described above. This method may also be combined with separate platelet poor plasma and/or red blood cell collection.

IV. Use of the System to Perform a Combined RBC/Plasma Collection Procedure

Any of the previously described chambers may be further utilized to perform a combined red blood cell and plasma collection procedure—which collects red blood cells and plasma separately—instead or in addition to the collection of platelet concentrate collection procedures described above. As such, the system and its components may be modified, as necessary, to perform the steps of this procedure, as described in more detail below.

A. First Draw Cycle

Figure 47:
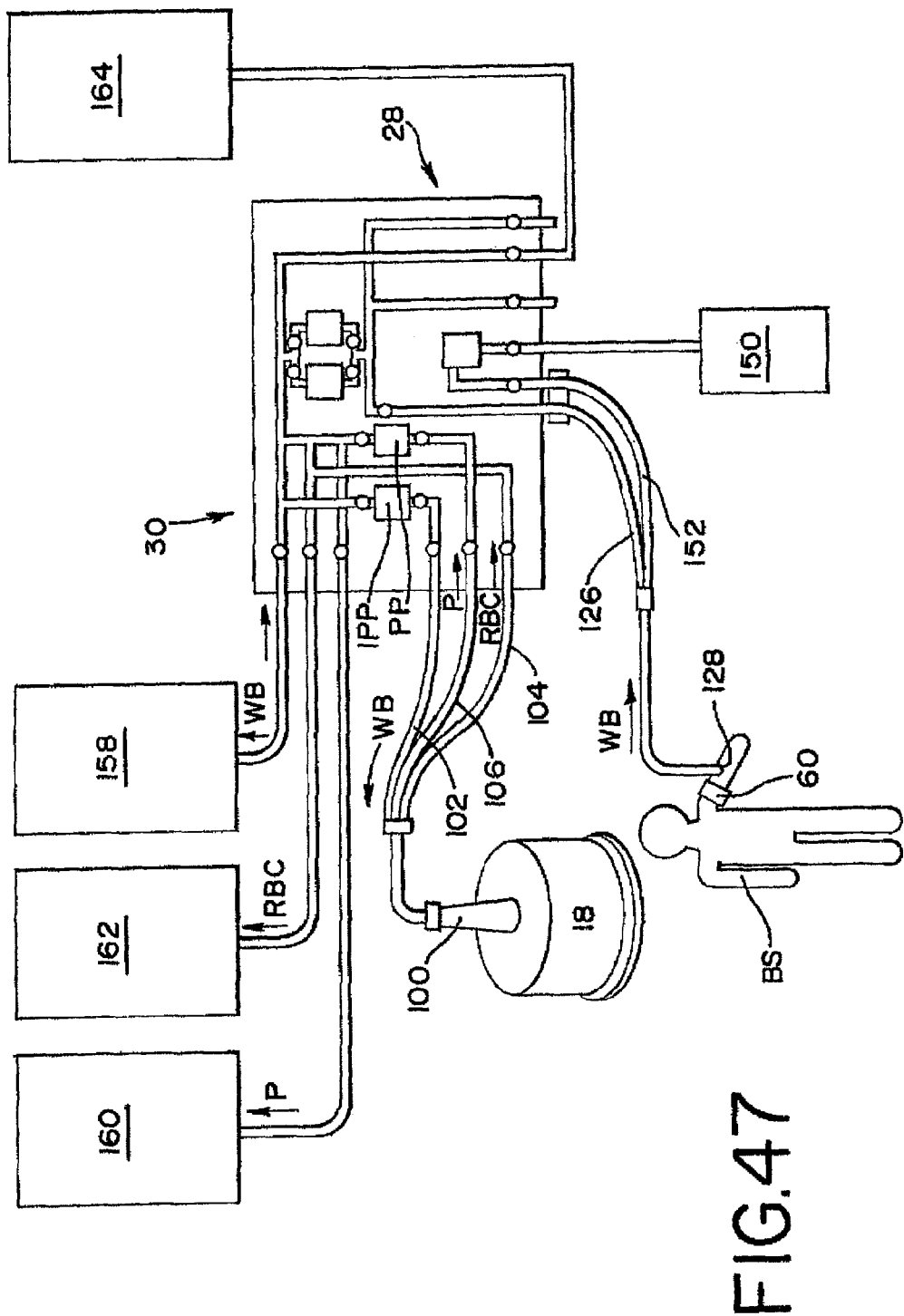
FIGS. 47 and 48 are schematic views of a fluid circuit that can be implemented in accordance with another method described herein.

As shown in FIG. 47, a blood source BS is fluidly connected so as to allow the blood to be processed by the blood separation device 10 (FIG. 1) and its flow set 12 (FIGS. 4-6). Fluid entry of the blood into the flow set is schematically shown in FIG. 47. The blood source BS may be a donor or other human subject, as shown, or another blood source connected to the device. Such donor may be connected to the blood separation device, for example by insertion of the phlebotomy needle 128 into an arm of the donor. Whole blood may flow into the flow line 126 (see also FIGS. 5 and 6) where it may be mixed anticoagulant through a respective flow line 152 from an anticoagulant reservoir 150, as generally shown in FIG. 47.

After the blood source BS is connected to the device, whole blood WB preferably travels through the appropriate flow tubes as directed by the system to fill the chamber 18. The chamber 18 presumably has been prepared for blood processing through one or more pre-collection procedures such as purging the chamber of air and priming the chamber with saline and/or other procedures as appropriate. The whole blood enters the chamber 18 through inlet flow line 102 until the chamber 18 is full. Whole blood is also drawn from the blood source BS and is temporarily stored in the in-process container 158 for subsequent processing by the chamber 18. The volume of whole blood which is drawn from the blood source BS is measured such as by the weigh scales 62 (FIGS. 3-6) of the system. Collection of whole blood from the blood source BS continues either until a certain predetermined volume of whole blood is reached or to allow a partial or full return cycle, as discussed below. By way of example and not limitation, the procedure may collect approximately 2 units or 800 ml of whole blood during a combined red cell and plasma collection procedure. Other whole blood collection volumes are possible and will depend on the targeted volume and type of components which are being collected.

Similar to previous methods discussed above, the whole blood within the chamber 18 is processed to allow separation into its components based on density, as shown in FIG. 11. After sufficient processing time, a fluid is removed from each side of the interface. Plasma P is removed from one side of the interface. Red blood cells are removed from the other side of the interface. In FIG. 47, plasma P exits the chamber 18 through the outlet tube 106 and red blood cell concentrate RBC exits the outlet tube 104.

The first and second fluid components, preferably plasma and red blood cells, are removed from the chamber into their respective collection containers 160 and 162. The volume of each fluid component collected within the containers 160 and 162 is also measured throughout the collection cycle. Processing and collection of the components from the chamber 18 preferably continues until the volume within at least one of the fluid collection containers 160 and 162 reaches a predetermined minimum threshold, but before a targeted total volume of at least one fluid component is collected. When one of the volumes of the containers 160 and 162 reaches the predetermined minimum threshold, the device is configured to allow a full or partial return of at least one of the blood components.

B. Return Cycle

Figure 48:
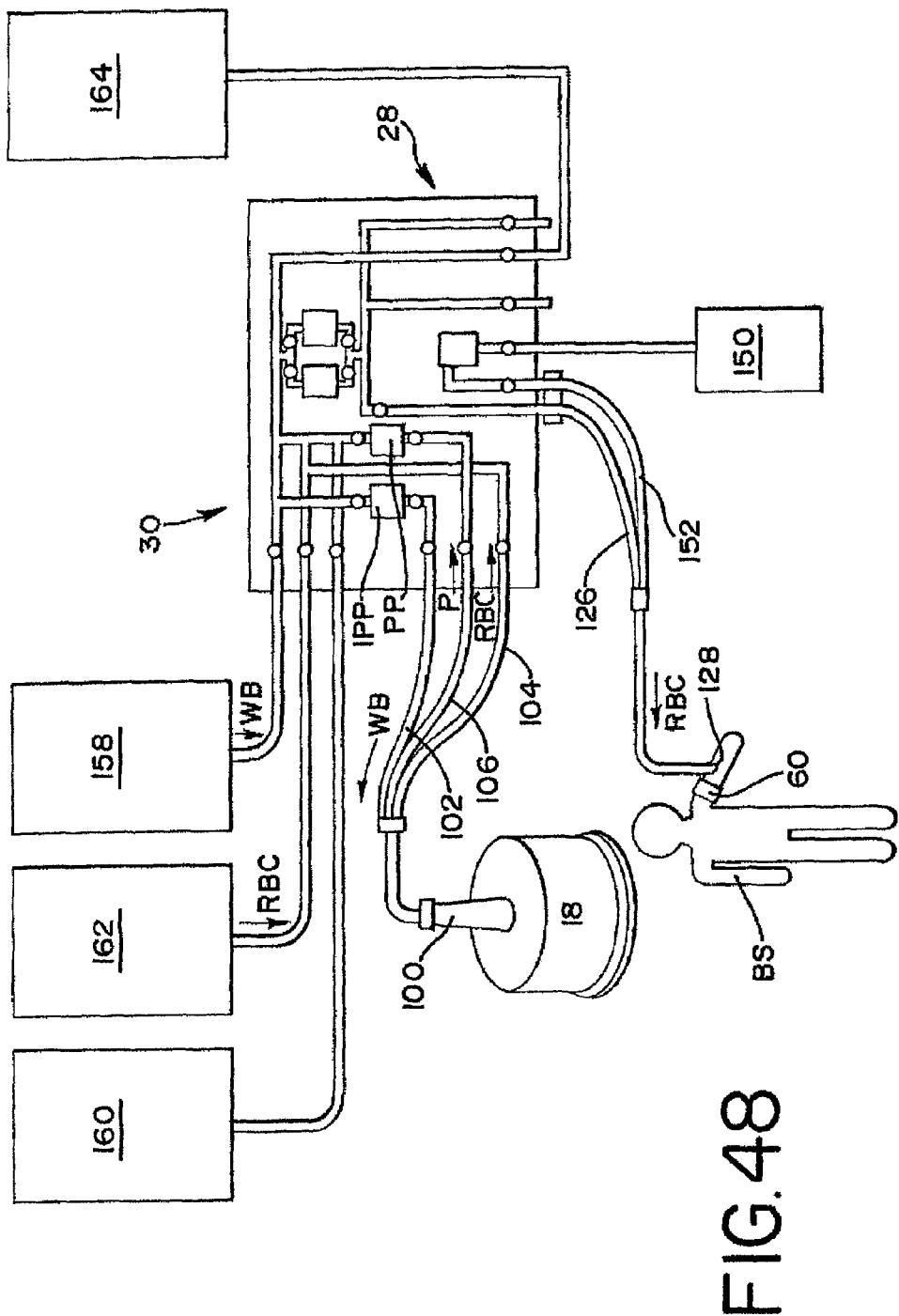

In FIG. 48, a portion of at least one of the fluid components, preferably red blood cells RBC, is returned to the donor. During the return cycle, whole blood from the in-process container 158 flows into the chamber 18 and also is processed. Separation and collection of the components in the chamber 18 preferably continues although at least one of the components may be returned to the blood source, if desired. In FIG. 48, red blood cells RBC exiting the chamber 18 are returned to the donor. All or a portion of the red blood cells which are collected up to this point in the procedure may be returned to the donor, and the amount returned may depend on the specific procedure employed.

Figure 49:
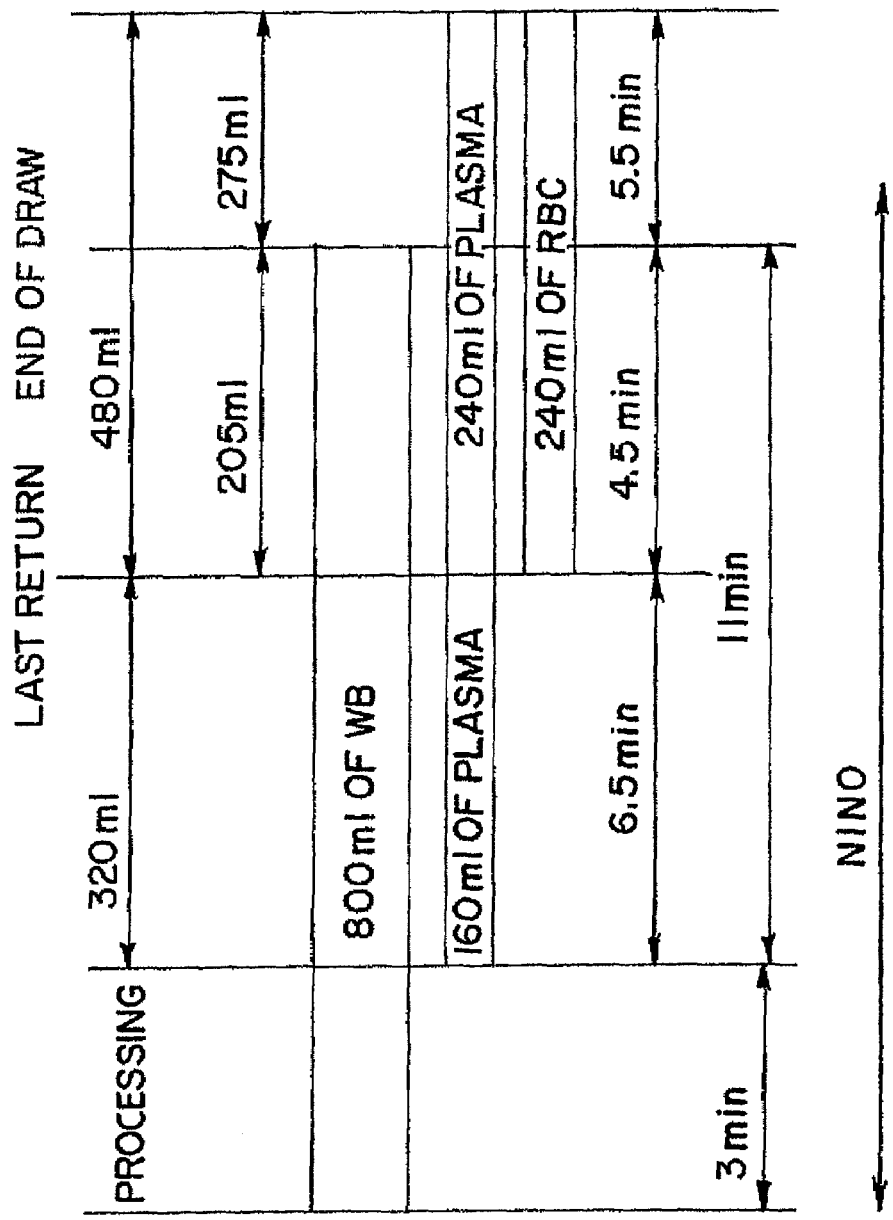
FIG. 49 is a chart illustrating the collection and return cycles of at least a portion of a fluid component relative to a blood source in accordance with one of the methods described herein.

FIG. 49 shows a more detailed account of a combined red blood cell and plasma procedure where all the red blood cells are return to the donor at a "Last Return" and all the plasma is stored within the system. While the volume of plasma within the plasma collection container 160 may be retained within the system, it is also possible that a portion of the plasma may be returned to the donor, depending on the requirements of the procedure.

After the desired volume of at least one of the fluid components has been returned to the blood source, the return cycle terminates. Additional return cycles are preferably not commenced, as these would increase the time during which the blood source must be connected to the separation device.

C. Second Draw Cycle

After the return cycle, additional whole blood is withdrawn from the blood source and processed, as previously described and shown in FIG. 47. The amount of whole blood which is withdrawn from the blood source BS during the second draw cycle is based on a predicted value. Such value preferably depends on the volumes of plasma and red blood cells which are collected during the first collection cycle and the hematocrit of the red blood cells leaving the chamber 18. The volumetric data of plasma in the container 160 and the volume of red blood cells in the container 162 are preferably monitored throughout the first draw cycle, such as by the weighing sensors, and are also measured at the end of the first draw cycle, prior to any return of such components to the blood source BS. The hematocrit of the chamber 18 is determined optically through the sensor 148 (FIG. 11) in the outlet tube 104. The system uses the volumetric and hemacrit values to empirically calculate how much whole blood must be withdrawn from the blood source BS to achieve a targeted final volume of at least one of or both fluid components. In its calculation, the system also takes into account whether the volume of plasma or red blood cells which have already been collected will be retained or returned to the blood source BS.

In the example of FIG. 49, the volume of plasma retained after the first collection cycle is approximately 160 ml. The volume of red blood cells retained is 0 ml or approximately zero. The targeted volume of plasma and red blood cells are approximately 400 ml and 240 ml, respectively. The additional whole blood to be drawn from the donor to achieve these targeted volumes is determined by the system as approximately 480 ml. Therefore, this is the volume of whole blood which must be drawn during the second collection cycle. Other volumes will be apparent with different volumetric and hemacrit values.

D. Processing Cycle after Disconnection

The blood source BS or donor may be disconnected from the device after the predicted volume of whole blood has been withdrawn. Processing of the whole blood is repeated as described above in FIG. 47 for the First Draw Cycle except with the blood source BS being disconnected from the device. Processing of the whole blood continues after disconnection of the donor, thus reducing the actual time that the donor needs to be connected to the device. The total amount of time elapsed during which the blood source BS is connected to the device is thus less than the total amount of time during which the whole blood undergoes collection and processing by the device.

By way of example and not limitation, FIG. 49 shows collection procedure for approximately 800 ml of whole blood which has a total processing time of approximately 21 minutes. This procedure collects approximately 400 ml of plasma and approximately 240 ml (or 1 unit) of red blood cells—with the remaining red blood cells having been returned to the donor during the return cycle. The total time that the donor is connected to the device is less than the total processing time, —i.e., less than 21 minutes—since the donor may be disconnected after the last return. In FIG. 49, the total time that the donor is connected to the device may be approximately 14 minutes. Other total processing times and donor connection times are possible and may depend on the procedure objectives.

Preferably, at least two components such as plasma and red blood cells are removed and stored in their respective collection containers 160 and 162, either until the total targeted volume of at least one blood component is reached or until all the blood has been processed. Further processing or separation may be employed in accordance with any of the above described methods or other collection procedures. For example, any one or more of the above methods may be employed to collect platelet concentrate. Platelet poor plasma may be used to resuspend platelets from the interface in accordance with any of the previously described methods. Alternatively, a platelet additive solution or PAS may be used for collecting platelet concentrate methods. Thus, this method may also be combined with any of the above-described to collect at least two blood components, plasma and red blood cells, as well as platelet concentrate. The amount of collection will vary depending on collection limitations set by the particular country.

As can be seen from the above description, the present invention has several different aspects and features, which are not limited to the specific chamber shown in the attached drawings or to the specific procedures discussed. Variations of these features may be embodied in other structures for carrying out other procedures for blood separation, processing or collection.

The invention claimed is:

1. A separation channel for rotation about an axis to separate a biological fluid including:
   radially spaced apart inner and outer side wall portions and an end wall portion, the channel having an axial length, an inlet to convey fluid into the channel;
   a barrier located in the channel intermediate the side wall portions and having upstream and downstream sides and an axial end within the channel, the barrier extending to the outer wall portion and joining the outer wall portion along a substantial portion of the axial length of the channel; and
   a first flow path communicating between the upstream and downstream sides of the barrier around the axial end of the barrier.

2. The separation channel of claim 1 further comprising a second end wall portion being opposed to the first named end wall portion, and at least a portion of the first flow path being located at an intermediate location between the first and second end wall portions.

3. The separation channel of claim 1 wherein at least a portion of the first flow path is defined by an axially disposed surface of the barrier, which surface forces at least one blood component in an axial direction of the channel.

4. The separation channel of claim 1 further comprising a second end wall portion being opposed to the first named end wall portion, and wherein the first flow path is defined by a surface of the second end wall portion.

5. The separation channel of claim 1 wherein a surface of the first flow path includes the outer wall portion.

6. The separation channel of claim 1 wherein the barrier extends to a radial position inward of the inner wall portion.

7. The separation channel of claim 1 further comprising a collection region downstream of the barrier in fluid communication with the first flow path.

8. The separation channel of claim 7 further comprising first and second openings communicating with the collection region for allowing flow of one or more fluid components from the collection region.

9. The separation channel of claim 1 further comprising a second flow path communicating between the upstream and downstream sides of the barrier.

10. The separation channel of claim 9 wherein the second flow path is adjacent the inner side wall portion.

11. The separation channel of claim 9 wherein the first and second flow paths are in communication in the separation channel downstream of the barrier.

12. The separation channel of claim 9 further comprising a third flow path communicating with the separation channel upstream of the barrier.

13. The separation channel of claim 1 further comprising a second flow path that is isolated from the first flow path.

14. The separation channel of claim 9 wherein a first component of a biological fluid is conveyed in the first flow path and a second component of a biological fluid is conveyed in the second flow path.

15. The separation channel of claim 14 wherein the first component includes red blood cells and the second component includes plasma.

16. The separation channel of claim 14 wherein the first and second components may be combined downstream of the barrier.

17. The separation channel of claim 1 wherein the outer side wall portion includes a section in the vicinity of the barrier located radially outward of the outer side wall portion.

* * * * *